United States Patent
Schoenherr et al.

(10) Patent No.: US 10,626,402 B2
(45) Date of Patent: *Apr. 21, 2020

(54) NUCLEASE-MEDIATED DNA ASSEMBLY

(71) Applicant: Regeneron Pharmaceuticals, Inc., Tarrytown, NY (US)

(72) Inventors: Chris Schoenherr, Piermont, NY (US); John McWhirter, Hastings-on-Hudson, NY (US); Corey Momont, White Plains, NY (US); Caitlin L. Goshert, Boston, MA (US); Lynn MacDonald, Harrison, NY (US); Gregg S. Warshaw, Bayside, NY (US); Jose F. Rojas, Newburgh, NY (US); Ka-Man Venus Lai, San Francisco, CA (US); David M. Valenzuela, Yorktown Heights, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/296,003

(22) Filed: Mar. 7, 2019

(65) Prior Publication Data
US 2019/0194668 A1   Jun. 27, 2019

Related U.S. Application Data

(63) Continuation of application No. 15/638,832, filed on Jun. 30, 2017, now Pat. No. 10,273,488, which is a continuation of application No. 14/747,461, filed on Jun. 23, 2015, now Pat. No. 9,738,897.

(60) Provisional application No. 62/015,809, filed on Jun. 23, 2014, provisional application No. 62/016,400, filed on Jun. 24, 2014, provisional application No. 62/036,983, filed on Aug. 13, 2014.

(51) Int. Cl.
| C12N 15/66 | (2006.01) |
| C12N 15/10 | (2006.01) |
| C12N 15/64 | (2006.01) |

(52) U.S. Cl.
CPC ......... *C12N 15/66* (2013.01); *C12N 15/1031* (2013.01); *C12N 15/64* (2013.01)

(58) Field of Classification Search
None
See application file for complete search history.

(56) References Cited

U.S. PATENT DOCUMENTS

| 9,580,715 B2 | 2/2017 | Schoenherr et al. |
| 9,738,897 B2 | 8/2017 | Schoenherr et al. |
| 10,237,488 B2 | 3/2019 | Yokoya |
| 10,421,957 B2 | 9/2019 | Lindstrom |
| 2010/0035768 A1 | 2/2010 | Gibson et al. |
| 2013/0298265 A1 | 11/2013 | Cunnac et al. |
| 2015/0079680 A1 | 3/2015 | Bradley et al. |
| 2015/0184199 A1 | 7/2015 | Horwitz et al. |
| 2015/0211058 A1 | 7/2015 | Carstens |
| 2015/0376628 A1 | 12/2015 | Schoenherr et al. |
| 2016/0053272 A1 | 2/2016 | Wurtzel et al. |
| 2016/0060671 A1 | 3/2016 | Hsieh et al. |
| 2016/0115486 A1 | 4/2016 | Schoenherr et al. |
| 2016/0186147 A1 | 6/2016 | Cady et al. |
| 2017/0198268 A1 | 7/2017 | Jacobson et al. |
| 2018/0002706 A1 | 1/2018 | Wang et al. |
| 2018/0002708 A1 | 1/2018 | Schoenherr et al. |
| 2018/0105806 A1 | 4/2018 | Voigt et al. |
| 2018/0362989 A1 | 12/2018 | Wang et al. |

FOREIGN PATENT DOCUMENTS

| EP | 3155099 B2 | 3/2018 |
| EP | 3450558 A2 | 3/2019 |
| WO | WO 2009/103027 A2 | 8/2009 |
| WO | WO 2011/154927 | 12/2011 |
| WO | WO 2013/142578 A1 | 9/2013 |
| WO | WO 2014/089290 A1 | 6/2014 |
| WO | WO 2014/093622 A2 | 6/2014 |
| WO | WO 2014/143381 | 9/2014 |
| WO | WO 2015/095804 | 6/2015 |
| WO | WO 2015/200334 A1 | 12/2015 |
| WO | WO 2016/007604 A1 | 1/2016 |

(Continued)

OTHER PUBLICATIONS

Koonin et al., "Diversity, classification and evolution of CRISPR-Cas systems" 37 Current Opinion in Microbiology 67-78 (2017).*
Sorek et al., "CRISPR-Mediated Adaptive Immune Systems in Bacteria and Archaea" 82 Annual Review of Biochemistry 237-266 (2013).*
"CRISPR in the lab: A practical guide," retrieved from <http://www.addgene.org/CRISPR/guide> on May 29, 2014.
Gibson et al., "Enzymatic assembly of DNA molecules up to several hundred kilobases," Nature Methods, 6(5): 343-347, May 2009.
Jinek et al., "A programmable dual-RNA-guided DNA endonuclease in adaptive bacterial immunity," Science, 337: 816-821, Aug. 7, 2012.

(Continued)

*Primary Examiner* — Nancy J Leith
(74) *Attorney, Agent, or Firm* — Yongjin Choi; Alston & Bird, LLP

(57) ABSTRACT

Methods are provided herein for assembling at least two nucleic acids using a sequence specific nuclease agent (e.g., a gRNA-Cas complex) to create end sequences having complementarity and subsequently assembling the overlapping complementary sequences. The nuclease agent (e.g., a gRNA-Cas complex) can create double strand breaks in dsDNA in order to create overlapping end sequences or can create nicks on each strand to produce complementary overhanging end sequences. Assembly using the method described herein can assemble any nucleic acids having overlapping sequences or can use a joiner oligo to assemble sequences without complementary ends.

52 Claims, 19 Drawing Sheets
Specification includes a Sequence Listing.

(56) References Cited

FOREIGN PATENT DOCUMENTS

| WO | WO 2016/025759 A1 | 2/2016 |
|---|---|---|
| WO | WO 2016/0333115 A2 | 3/2016 |
| WO | WO 2016/100389 A1 | 6/2016 |
| WO | WO 2016/109255 A1 | 7/2016 |
| WO | WO 2016/130697 A1 | 8/2016 |
| WO | WO 2018/013990 A1 | 1/2018 |
| WO | WO 2018/048827 A1 | 3/2018 |

OTHER PUBLICATIONS

Cong et al., "Multiplex genome engineering using CRISPR/Cas Systems," Science, 339: 819-823, Feb. 15, 2013.
Mali, et al., "RNA-guided human genome engineering via Cas9," Science, 339: 823, Feb. 15, 2013.
Gibson, D.G., "Enzymatic Assembly Of Overlapping DNA Fragments," Methods in Enzymology, 498: 349-361, 2011.
Li, M.Z., et al., "Harnessing homologous recombination in vitro to generate recombinant DNA via SLIC," Nature Methods, 4(3): 251-256, Mar. 1, 2007.
Zhao, G., et al., "Realizing directional cloning using sticky ends produced by 3'-5' exonuclease of Klenow fragment," Journal of Biosciences, 38(5): 857-866, Nov. 26, 2013.
Merryman, C., et al., "Methods and applications for assembling large DNA constructs," Metabolic Engineering, 14(3): 196-204, Mar. 13, 2012.
Wang, J-W, et al., "CRISPR/Cas9 nuclease cleavage combined with Gibson assembly for seamless cloning," BioTechniques, pp. 161-170 including Supplemental Material, Apr. 1, 2015, retrieved from http://www.ncbi.nlm.nih.gov/pubmed/25861928.
Lee, N.C.O., et al., "Highly efficient CRISPR/Cas9-mediated TAR cloning of genes and chromosomal loci from complex genomes in yeast," Nucleic Acids Research, 43(8): e55, Feb. 17, 2015.
Casini, A., et al., "Bricks and blueprints: methods and standards for DNA assembly," Nature Reviews, pp. 568-576, Jun. 17, 2015, retrieved from http://www.ncbi.nlm.nih.gov/pubmed/26081612.
Ran, F.A., et al., "Double nicking by RNA-guided CRISPR Cas9 for enhanced genome editing specificity," Cell, 154(6): 1380-1389, Sep. 12, 2013.
Holowachuk, E.W., et al., "Efficient gene synthesis by Klenow assembly/extension-Pfu polymerase amplification (KAPPA) of overlapping oligonucleotides," Genome Research, 4(5): 299-302, Apr. 1, 1995.
Orlando, S.J., et al., "Zinc-finger nuclease-driven targeted integration into mammalian genomes using donors with limited chromosomal homology," Nucleic Acids Research, 38(15): e152, Jun. 8, 2010.
Maresca, M., et al., "Obligate ligation-gated recombination (ObLiGaRe): Custom-designed nuclease-mediated targeted integration through nonhomologous end joining," Genome Research, 23(3): 539-546, Nov. 14, 2012.
Wang, R-Y, et al., "CRISPR/Cas9 nuclease Cleavage combined with Gibson assembly for seamless Cloning," BioTechniques, pp. 161-170, Apr. 1, 2015, retrieved from http://www.ncbi.nlm.nih.gov/pubmed/25861928.
Ramon, A., et al., "Single-step linker-based combinatorial assembly of promoter and gene cassettes for pathway engineering," Biotechnology Letters, 33(3): 549-555, Nov. 4, 2010.
Lee, B-R., et al., "Emerging tools for synthetic genome design," Molecules and Cells, 35(5): 359-370, May 2, 2013.
Vroom, J.A., et al., "Modular construction of plasmids through ligation-free assembly of vector components with oligonucleotide linkers," Biotechniques, 44(7): 924-926, Jun. 1, 2008.
Stevenson, J., et al., "A practical comparison of ligation-independent cloning techniques," PLOS One, 8(12): e83888, Dec. 23, 2013.
Casini, A., et al., (Sep. 23, 2014) "Advanced DNA assembly strategies and standards for synthetic biology," (PhD Thesis), retrieved from https://spiral.imperial.ac.uk/bitstream/10044/1/25291/1/Casini-A-2015-PhD-Thesis.pdf.
PCT International Search Report and Written Opinion of the International Searching Authority for PCT/US2015/037199, dated Nov. 25, 2015.
Invitation to Pay Additional Fees for PCT/US2015/037199, dated Sep. 25, 2015.
Gibson, et al., "Enzymatic assembly of DNA molecules up to several hundred kilobases," Nature Methods, 6(5): 343-347 including Supplemental Material, May 2009.
De Kok, et al., "Rapid and Reliable DNA Assembly via Ligase Cycling Reaction," ACS Synth. Biol., 3, 97-106, Jan. 9, 2014.
U.S. Appl. No. 14/926,720, Non-Final Office Action dated Mar. 2, 2016.
Roth, et al., "A rapid and simple method for DNA engineering using cycled ligation assembly," PLoS One, 9(9), p. e107329, Sep. 16, 2014.
Anderson, et al., "BglBricks: A flexible standard for biological part assembly," J. Biol. Eng., 4(1), p. 1, 2010.
Trubitsyna, et al., "PaperClip: rapid multi-part DNA assembly from existing libraries," Nucleic Acids Res., 42(20), e154, Sep. 8, 2014.
Wang, R-Y, et al., "DNA fragments assembly based on nicking enzyme system," PLoS One, vol. 8(3), p. e57943, Mar. 6, 2013.
Chao, et al., "Recent advances in DNA assembly technologies," FEMS Yeast Res., vol. 15, pp. 1-9, Jan. 14, 2015.
U.S. Appl. No. 14/926,720, Final Office Action dated Jul. 26, 2016.
Tsvetanova et al., "Genetic Assembly Tools for Synthetic Biology," Methods in Enzymology, vol. 498, pp. 327-348, 2011.
U.S. Appl. No. 14/747,461, Non-Final Office Action dated Aug. 9, 2016.
U.S. Appl. No. 14/926,720, Notice of Allowance dated Oct. 17, 2016.
"Frequencies of Restriction Sites," New England BioLabs [Retrieved from the Internet Oct. 23, 2016: <https://www.neb.com/tools-and-resources/selection-charts/frequencies-of-restriction-sites?device=pdf>].
Wu et al., "Custom-designed zinc finger nucleases: What is next?," Cell. Mol. Life. Sci., vol. 64(22), pp. 2933-2944, 2007.
U.S. Appl. No. 14/747,461, Final Office Action dated Dec. 9, 2016.
PCT International Preliminary Report on Patentability for PCT/US2015/037199, dated Dec. 27, 2016.
U.S. Appl. No. 14/747,461, Advisory Action dated Feb. 22, 2017.
U.S. Appl. No. 14/747,461, Examiner Initiated Interview Summary dated Feb. 22, 2017.
U.S. Appl. No. 14/747,461, Notice of Allowance dated May 4, 2017.
U.S. Appl. No. 14/747,461, Examiner Initiated Interview Summary dated May 4, 2017.
Karvelis, et al., "Programmable DNA cleavage in vitro by Cas9," Biochem. Soc. Trans., vol. 41, pp. 1401-1406, 2013.
EP 18162656.5 Extended European Search Report dated Apr. 18, 2018.
U.S. Appl. No. 15/638,832 Non-Final Office Action dated May 15, 2018.
U.S. Appl. No. 15/638,832 Notice of Allowance dated Dec. 10, 2018.
EP 15735807.8 Decision to Grant a European Patent dated Feb. 22, 2018.
EP 15735807.8 Examination Report dated May 10, 2017.
EP 15735807.8 Intention to Grant dated Oct. 25, 2017.

* cited by examiner

Cloning efficiencies for Cas9/Gibson Assembly method

| Construct | Cas9 used | Method for removing Cas9 | total # colonies | # (%) correct clones |
|---|---|---|---|---|
| 6177(BDLC) + HYG | Cas9-6xHis | Proteinase K | 3 | 3 (100) |
| HLA-DQ + HLA-DR | 6xHis-MBP-Cas9 | Proteinase K, phenol:chloroform | 1 | 1 (100) |
| | | SDS, heat inact, phenol:chloroform | 1 | 1 (100) |
| | | Heat inact, phenol:chloroform | 16 | 16 (100) |

Time required for BAC cloning steps §

| Method | Time |
|---|---|
| BHR | ~1 week |
| BHR + BAC Ligation | >2 weeks |
| 2 BHRs + BAC ligation | ~5 weeks |
| Cas9/Gibson Assembly | 2 days |

§ starting from BAC maxiprep DNA ending with E. coli colonies
BHR: bacterial homologous recombination

*FIG. 4*

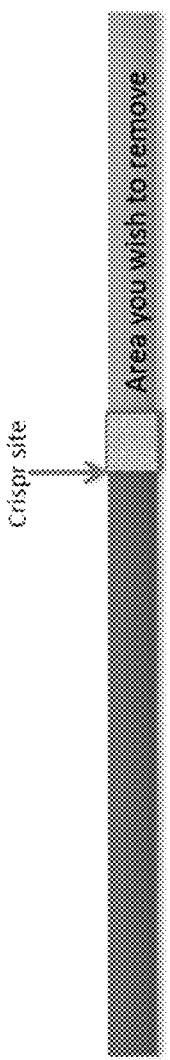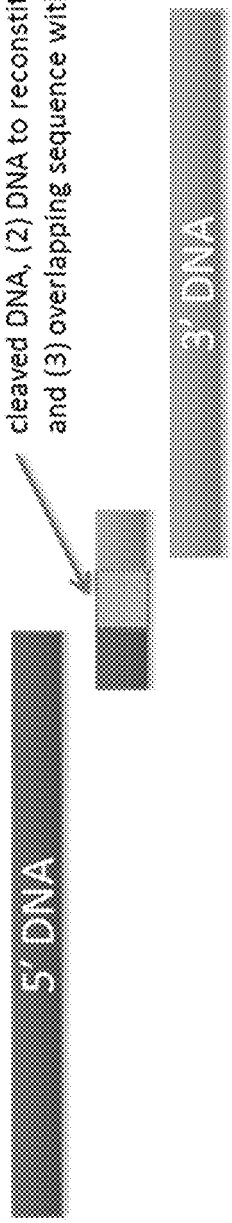
FIG. 6

Linker 1 (SEQ ID NO: 12)

Linker 2 (SEQ ID NO: 13)

SEQUENCE LISTING

```
<160> NUMBER OF SEQ ID NOS: 25

<210> SEQ ID NO 1
<211> LENGTH: 80
<212> TYPE: RNA
<213> ORGANISM: Artificial Sequence
<220> FEATURE:
<223> OTHER INFORMATION: Synthetic chimeric gRNA

<400> SEQUENCE: 1
guuuuagagc uagaaauagc aaguuaaaau aaggcuaguc cguuaucaac uugaaaagu      60 ggcaccgagu cggugcuuuu                                                 80

<210> SEQ ID NO 2
<211> LENGTH: 42
<212> TYPE: RNA
<213> ORGANISM: Artificial Sequence
<220> FEATURE:
<223> OTHER INFORMATION: Synthetic chimeric gRNA

<400> SEQUENCE: 2
guuuuagagc uagaaauagc aaguuaaaau aaggcuaguc cg                        42

<210> SEQ ID NO 3
<211> LENGTH: 30
<212> TYPE: RNA
<213> ORGANISM: Artificial Sequence
<220> FEATURE:
<223> OTHER INFORMATION: Synthetic crRNA

<400> SEQUENCE: 3
guuuuagagc uagaaauagc aaguuaaaau                                      30
```

```
<210> SEQ ID NO 4
<211> LENGTH: 33
<212> TYPE: RNA
<213> ORGANISM: Artificial Sequence
<220> FEATURE:
<223> OTHER INFORMATION: Synthetic crRNA

<400> SEQUENCE: 4
guuuuagagc uagaaauagc aaguuaaaau aag                            33

<210> SEQ ID NO 5
<211> LENGTH: 26
<212> TYPE: RNA
<213> ORGANISM: Artificial Sequence
<220> FEATURE:
<223> OTHER INFORMATION: Synthetic crRNA

<400> SEQUENCE: 5
gaguccgagc agaagaagaa guuuua                                    26

<210> SEQ ID NO 6
<211> LENGTH: 12
<212> TYPE: RNA
<213> ORGANISM: Artificial Sequence
<220> FEATURE:
<223> OTHER INFORMATION: Synthetic tracrRNA

<400> SEQUENCE: 6
aaggcuaguc cg                                                   12

<210> SEQ ID NO 7
<211> LENGTH: 50
<212> TYPE: RNA
<213> ORGANISM: Artificial Sequence
<220> FEATURE:
<223> OTHER INFORMATION: Synthetic tracrRNA

<400> SEQUENCE: 7
aaggcuaguc cguuaucaac uugaaaaagu ggcaccgagu cggugcuuuu          50

<210> SEQ ID NO 8
<211> LENGTH: 23
<212> TYPE: DNA
<213> ORGANISM: Artificial Sequence
<220> FEATURE:
<223> OTHER INFORMATION: a target locus that is linked to a guide RNA
      (gRNA)
<220> FEATURE:
<221> NAME/KEY: misc_feature
<222> LOCATION: 2, 3, 4, 5, 6, 7, 8, 9, 10, 11, 12, 13, 14, 15, 16, 17,
      18, 19, 20, 21
<223> OTHER INFORMATION: n = A,T,C or G

<400> SEQUENCE: 8
gnnnnnnnnn nnnnnnnnnn ngg                                       23

<210> SEQ ID NO 9
<211> LENGTH: 41
<212> TYPE: RNA
<213> ORGANISM: Artificial Sequence
<220> FEATURE:
<223> OTHER INFORMATION: Synthetic tracrRNA

<400> SEQUENCE: 9
caaaacagca uagcaaguua aaauaaggcu aguccguuau c                   41
```

```
<210> SEQ ID NO 10
<211> LENGTH: 22
<212> TYPE: RNA
<213> ORGANISM: Artificial Sequence
<220> FEATURE:
<223> OTHER INFORMATION: Synthetic crRNA region complementary to
      tracrRNA

<400> SEQUENCE: 10
guuuuagagc uaugcuguuu ug                                          22

<210> SEQ ID NO 11
<211> LENGTH: 89
<212> TYPE: RNA
<213> ORGANISM: Artificial Sequence
<220> FEATURE:
<223> OTHER INFORMATION: Synthetic tracrRNA

<400> SEQUENCE: 11
guuggaacca ucaaaacag cauagcaagu uaaaauaagg cuaguccguu aucaacuuga   60
aaaaguggca ccgagucggu gcuuuuuuu                                   89

<210> SEQ ID NO 12
<211> LENGTH: 145
<212> TYPE: DNA
<213> ORGANISM: Artificial Sequence
<220> FEATURE:
<223> OTHER INFORMATION: Synthetic -Confirmation of seamless assembly
      from mBAC to cassette

<400> SEQUENCE: 12
ttgtgtgaat ataataatat cagtgcttct ttacttccaa aactggacag cgcatcaaac   60
atcagaaaca acagtatcag ctcctgtccc aactaccatg ggtaccgatt taaatgatcc   120
agtggtcctg cagaggagag attgg                                        145

<210> SEQ ID NO 13
<211> LENGTH: 205
<212> TYPE: DNA
<213> ORGANISM: Artificial Sequence
<220> FEATURE:
<223> OTHER INFORMATION: Synthetic -confirmation of seamless assembly
      from cassette to mBAC

<400> SEQUENCE: 13
cagcccctag ataacttcgt ataatgtatg ctatacgaag ttatgctagc tcggtcacac    60
tgtcagcttc ctgtgtttcc taggccatga taagatgcag caaagtttct gcaatgcaca   120
atgaggcagc cgtcggaata gatttgagaa agtcatgatg atgcaatgtg cacactcttc   180
ctttgtattt atctctatcc accat                                        205

<210> SEQ ID NO 14
<211> LENGTH: 138
<212> TYPE: DNA
<213> ORGANISM: Artificial Sequence
<220> FEATURE:
<223> OTHER INFORMATION: Synthetic -confirmation of seamless assembly
      from mBAC to cassette

<400> SEQUENCE: 14
actttagggt ttggttggtt tttaaagccc tatttccagt atgtggaaat gagccaaccc    60
aggacagctt ccgctggatc gtggacagct tctatggccg tcgacgtgta cactcgagat   120
aacttcgtat aatgtatg                                                138
```

<210> SEQ ID NO 15
<211> LENGTH: 147
<212> TYPE: DNA
<213> ORGANISM: Artificial Sequence
<220> FEATURE:
<223> OTHER INFORMATION: Synthetic

<400> SEQUENCE: 15

```
tccaaacgac agcagaacta actgagagga gagcacagta gcggccgcaa attgctttga    60
gaggctctat aaaaccttag aggctattta aatttaaatg ccggcccga cggccaggcg    120 gccgccaggc ctacccacta gtcaatt                                        147
```

<210> SEQ ID NO 16
<211> LENGTH: 9
<212> TYPE: PRT
<213> ORGANISM: Unknown
<220> FEATURE:
<223> OTHER INFORMATION: Synthetic

<400> SEQUENCE: 16

```
Leu Ala Gly Leu Ile Asp Ala Asp Gly
1               5
```

<210> SEQ ID NO 17
<211> LENGTH: 49631
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22396)...(22533)
<223> OTHER INFORMATION: Linker 1
<220> FEATURE:
<221> NAME/KEY: misc_feature
<222> LOCATION: (22494)...(25426)
<223> OTHER INFORMATION: Cassette Sequence
<220> FEATURE:
<221> NAME/KEY: misc_feature
<222> LOCATION: (25427)...(25595)
<223> OTHER INFORMATION: Human Spacer Sequence
<220> FEATURE:
<221> NAME/KEY: misc_feature
<222> LOCATION: (25596)...(40791)
<223> OTHER INFORMATION: BMQ-208A16 sequence
<220> FEATURE:
<221> NAME/KEY: misc_feature
<222> LOCATION: (25387)...(25672)
<223> OTHER INFORMATION: Linker 2
<220> FEATURE:
<221> NAME/KEY: misc_feature
<222> LOCATION: (40792)...(40858)
<223> OTHER INFORMATION: Unique additional sequence of linker 3
<220> FEATURE:
<221> NAME/KEY: misc_feature
<222> LOCATION: (40752)...(40898)
<223> OTHER INFORMATION: Linker 3
<220> FEATURE:
<221> NAME/KEY: misc_feature
<222> LOCATION: (1)...(22395)
<223> OTHER INFORMATION: bmq-50F19
<220> FEATURE:
<221> NAME/KEY: misc_feature
<222> LOCATION: (40899)...(49631)
<223> OTHER INFORMATION: bmq-50F19

<400> SEQUENCE: 17

```
gctggagtgt ggtcaggcaa catccccaaa gggatggaga tgccgggacg acacctttag    60
ggaggcagtg gctctggtcc gggattccgg tgctggccat ccctcaccag ccacagcggt    120
```

```
tggcgcagga gggatcgccg cgcgcctggg gctaggggge gaactggacc gacttttcct      180
agttcgccta gctgctccga ccgctgccgc gccgagatgt tgaaagcaca ggcgagttct      240
aacttgcgcg ctcattcttt cagcgcgggg gaatcggtcg agggccctgc gtggcgctgg      300
cttccaccct cgcggccagg gggcaggcgc gggaggccgg cttcggctcc gtgcccctgc      360
aaacttccca agaccttcct tctccccccc acctcacccc ccagttcaat aaaatctacc      420
cttaaaggca gacttgcttt caaatccacg gcacccatta tgtgtttggt gtgaaacgct      480
atcaacattt aaaactctat tgtcccaagc gtcccaaatc cctgtaaatc ttccaccagc      540
ctggactcat tttcatctga aaagcctgtt tagtttgaat agaaaagcaa tcaggcgccc      600
ctctcgctct cgttggaatg tcaattaaaa tgcagatttc tcagagctct ttagcgcccc      660
aagaagtggg acaaaacagg atatttcagg ctgacaaatg aaagaaatgc tacaatgaag      720
tggggtggcg atgtgcaccc caaactgctt ggagtaccca ctgaaagagt aggtcaggga      780
ttatggtctt acttacgaca gcttatattt ttgggggttte gttgtgttta ggcccccccc     840
ttggtgtccc ccccccccat gagcccatga cagctccctt ccctattcag ccccgtggag      900
aagtaaggga gccttgaacc agggtagaga ggctacattt agtattaacc tgggagtgtt      960
gacttctccc aggagtaatc cacttgagaa caaaatgcca attgctctgc ccgctgaggt      1020
atcctggaac tacccttta ggtagcagta cccgtcgcac cgcccccctc cccaagggc       1080 ttgccttaaa ttaacctgcc ttcttgcagg acagggaga gtgtgtaaac gtgtataaca      1140
ctgcgcaagc tcaccagccg ggcccttcg gccgggtccc tttgcctgtc tttggaggca      1200
gacttgtgtg gagatgaccc caaggggcgg gtggccgtga agagccatcc gtcagagtga      1260
gggtgaggac tcctccctcg taggctgaga agagagtatc ctttcagggg gaaaaataaa      1320
cacgctgggg cttttctctgg ggttcagcct ccaggaagga ttatggtatt gaaggcagga      1380
agctgggatt gtggccgcca gcagcatgct gggcctgtgt tcccaacacg gagccttggg      1440
acctaattat cctgcctagg aggtcgctca gcactttgt ccactccggt gaggagctgt       1500
gcagacctgc tgccgtcact tctcgcctta cagaggtttg aggaggggggc tcctgtgggg     1560 gctgggactt cgaagaacga acgttcaagt tgagtcagcc tggggcactg gccatcttcc      1620
tcattcagct ggagctgagg tactcctggg tagtggctag tagagacagt gggcccagca      1680
ctctgcttca agacctactg ggacctgaga ttgcaaagtt gctggagagg ggagtttacc      1740
tgcattctga agttcttag gaaatcaacg agaatgtttg tgcactttcc tttgactggt       1800
atgtagaaat agacaaggaa ttatctttg tgactcttgg ctttaagaag aaagaagact       1860
tgggggaaca aaaatccttc cagccaacta aaaacactgg gcacctaact gctcatatac      1920
ccctggcttt tgttgttagc tataccattc tacctgtgct taaaaaaaca accaaacagc      1980
agcttcctat tcccctcttg gagatggtac gtcctctctg ccttagtctc agtgaaggct      2040
gaaaggaaca gattttagga cggaggttct ggcagtgtcg aaatcctgtg tcataattga      2100
aagcatcaaa agcgcacggg attagaattc ttttctctt tctctcttt tcattaaaac       2160 gctcacccat ccccagtctc ataaaatggg catcccagca tccaaagccc atggttttgt      2220
gcgatccttt cctgccattg gtttcagcag attctctaaa gctcgtgcat tctgactcaa      2280
agattagtca ctgaagacac tgaacaaaca taaagttatt tgtactgtgg taagcttttt      2340
tttttgggaa attctctgct ttggatctag taaattgagt gcccccttgt aactgatact      2400
tgggaggttt agccaatagg ttagcgtatt gaaagttccc aggccaatca cataccaggg     2460
```

-continued

```
cagcttgtac gtatcatcac cattactaat aaaatcttga attattcatc aagggttgta    2520
tctttacccc tttgacgtcg gttgcagata tttagttagt atgcctgtac actgccttgt    2580
agtcagtgga agggaattca ggctttgaat cccccggttg gattaaactc actctttgta    2640
agtggctgct tggcggaaga ttgaaataca cgcctgcatt cgaaaatgaa ttctgacaag    2700
tgtaaactgg tgggaatgtt tttgaagcct tcctgagatt ctttgattct gttggtctcc    2760
tttcttctg agaaccgttc tgaagcgagg acgtgccgct cagctcagct gaaatgcggt    2820
tctcagagca gacccttcct ccagtcagcg tcttaaaggc cagctggaat aagagacgtt    2880
aatgaggctg ccatgccaa gcccagcgtt ttaaactcag gttttctgc agttgccctt    2940
gaaaggaatg aaggtcaagt tgcttcagca accttgcagc tttgatagtg gacggaaggg    3000
cacgctgcag agctgggtgg ctgggtccta cagtgatggt ttatcttgcg tctcttaaaa    3060
gtaagcttaa aaaaaaaag attagcctac tgcagcttgt ggactagcct ggaaacacct    3120
gggacgctga ggtgaggatg aaggcttt ccgataatga aaagaatgt gtttgcgaat    3180
gtattgagag gctgagaaat ggttttatcc catctgggtt taagcaagtt ggcactgggg    3240
gaaaaaactg aatctggctg aatctctctc tttcagtggc agccacagca gcagcagcag    3300
cagcagtggg agcaggaaca gcagtaacaa cagcaacagc agcacagccg cctcagagct    3360
ttggctcctg agcccctgt gggctgaagg cattgcaggt agcccatggt ctcagaagaa    3420
gtgtgcagat gggattaccg tccacgtgga gatatgaag aggaccaggg attggcactg    3480
tgaccatggt cagctggggg cgcttcatct gcctggtctt ggtcaccatg caaccttgt    3540
ccctggcccg gcctccttc agtttagttg aggataccac tttagaacca gaaggtaagt    3600
tcatgcgtgc cattttaagg gtaccaagtc gttttgggga tgtgtctggg ggaagtggtc    3660
tttaagtggg aggcctgttt cagccggctg ccatatgagt agtctctctc cgcatcatat    3720
cggagcttag aagggagggt cttgtctccc aggcatgagt ggagtggttt ggtttgctct    3780
gttcttgtg cttgggtgag ggaagcagtg gcagttcttg tttagccagt gccttacagc    3840
actctggagg ggacgtacct tggcagggtg actgtggcct tctgcagttg ctctctagat    3900
tgagggaaaa gccttgaatc acactatctt ttggctaaag gaaataggca gcctctgaaa    3960
gctgactttt tttttctttt tccgcattgt ttaagagaaa agaaggttct gaagttgagc    4020
atggagagcc gtgccatgct ggatcggttt taagctggt gtaagctctt tgtgctttca    4080
cccggcatca cagagtgggc aggtttcatg ttgggaagat tggaaagtga atttgccaag    4140
agtcttcccc catctgggga aaagccagat ttcactagtg tgtttggctt tgcacacttg    4200
gttgcaaatg tgagaagcta gttgtgagga ggacgtggct gaaatccgga gctgggcaaa    4260
gcgctggtcc ttctcccagg tccttcagag acgtggtctg tggccaagcc tctctccttg    4320
gtgccgcacg ggaatctgtc atcaggaggg aatattggta ggcgagttat ttttgagtg     4380
gtaatccgag cgtgacactg cagatcgcag cactcatcgc cacttaatga acgtgtttgc    4440
tgagggccca cctggtgccg gctggctttg gagtccgtca cggtcctgag tgctggcagg    4500
tcagctgagt tgctgtggct atgcacactg aatcagggtc ctgattcatc cagatcatcc    4560
agaggggat tgtaggaggg acaggacccc tcccccaagg gtgacctcaa ggagggctat    4620
gtacccatct gagaggaggg cttgagaaat gggtccccag taagatccac ccagacagac    4680
actctccctg gctttgtgtg tatgtcgggc cacacagatg cctggaaatg ttataaatta    4740
ccaggtatct ttgaaaagga aatgaggtag gagtttgtg catgaggtgt gttcaacata     4800
cagcctcacg tccttttccg gaaccacctc tctgtgactt atcctgtgac gtcagggaga    4860
```

-continued

```
gtgtaatctg caacagtgac atgttttcaa agggcttaat gtgaggggga aaggattggg      4920
tttctgaaag tctggtctgc acttctttaa ttttgttaat aattaaaatg gatgtccccc      4980
taattgccgg ttgtccctgg agtgtgtggc tcagcactaa ctaaggaagc tgagctagga      5040
tttcctacag cgtgggcttc agaaacagcc ccggttagga agaattgtc attttcatt       5100
tggactctcg gggcagtgtt gctgtgagtt gatttcagtt gcagagtata aatggtcct      5160
ggagggtttc ctggactgca tctaattacc tcagaaaggt tacaagatgt ttgtactcgc      5220
aaggaggagg caggtggggg agaggaagga cagtgggctg gagtccccca aatggctctt      5280
tgtgtaagaa ccgatatcca acaatgctca cattgttgaa agcagatccc accacctggg      5340
gacctgtagg tacatgtaag gttagggagg gaggctgaga agtctccgaa gttgtaggtc      5400
acactttgcc aatgcccctg ggtacacttt gctaggctca gagtttgcat gaggttcgaa      5460
tcacatatag agttgggaga cgctaagaaa aagaaaagaa aagaaaaaa ggaaaaaagg       5520
aaaatgtctc aaggtgtgga gtttcaccag agcaagcttg ggaaatgcag agaaaccccca     5580
gagccttgat tggtgggatc tctttatcaa tagtcactga acagtagtac catccccaga     5640
tgccttctga ggaccagctc aagagattta gttttcacca gtgacctgga cagaaagcag     5700
aaagcacagc tcctggcatt gatggtggcc ttggccatcc ccatccccag caagctgggg     5760
acaaggggt gcacagttct cagtgcagca aacacggtac cctgagatga atgttgcttt      5820
tggatggagg aggtggtgat gctggatttc ggcagggtct gtgctcactc tccttgtctg     5880
ttagaccaac attgccactg acatccaggc catcaagcta gaggctaggc tccatgctag     5940
gctctggtgt ctaatgtgtg catatgtgca tctctccagc cgccatattt gatgcagcca     6000
ggacttcagc taacactgag ttcagcttct gtctcctgaa gctttaccat ggaaggcatc     6060
cgtttgctaa tttagaagct cagtttagat aatgtctatt gggccggaca aatatgtaat     6120
caggaagttc ctagaaagag cctgtgcctc actactaagg agcccttttg accctctagg     6180
gagatgttat gttcagtcat gtagttctgt gcagtgtatg tagccatgca atgtatgtcc     6240
tcaccccgaa tcctatcctg tccgtgtgtc tctggacact ttctcaagtg gcagcagcag     6300
gattgggtca agtcagttga cctaagaagg cagtcatctc tgtaagattt tcctcggtat     6360
ttcagaatag aaatgattgt atccagctgg tcatccctgt gacaaaggac aacagtatca     6420
acagttgggg acttcggagg ggtggtcccg attctaagta ctgttctgtt gattcaaatc     6480
ctgaatgttc ccagtgtagt caagcttgat tactgccagt ctcggctctt actttcagat     6540
tcccctgac gttgtcacct gctctggtta attaagtcat tgttgacatt aagggaatct     6600
gtttacccca gcccagtagg agctaaaata aaagggcttt cccaaaccca aacccttaat     6660
tactttccca ccctctgcta agtgcaaagg gacggcctgg gggtggggtg ggggtgggag     6720
tgagggagta atttacatgc cttaaaaaac acccaccatt tcttgggcag tcttctgggt     6780
tgatgctgtt ccggattgaa gtgagccagc gaaaacctcg tgagtgtgag gtctacgtgg     6840
agacctgctg aagggttccc ccccctcac caccaccacc acagggtagt tcaagtcctt      6900
tgtcagagag tatcctacat gctgtggtct cagcccccca catttaattg ccagttagaa     6960
gaagagaaaa gaaatatctg cgtggtgcaa gtggatgatt taacaggagt cttgtgtttc     7020
ctattatctg catttttgt tcctcagtgt gagtgtgaat atttaagagt tgactgtaac      7080
ttgatagttt cgctgaggaa caagggctta ttccttggtca attaaaccaa atgcaggcgc     7140
atgctgttaa acacacaatg aagtacacat tctttattag aatatagtgt atttcacaat     7200
```

```
tcatgggcaa ggaactgtgt ttaatattac ttctagagca aaaatctggc cagcccagaa    7260
aattggcatt tatataactc tttcttgctg gcttccactg atctgaatag agcaagtttg    7320
tgtgtgtgtg tgtgtgtgtg tgtgtgtgtg tgtgtgtacc tgtctgtcta tgttgcctgt    7380
ttatttcaat cagttaaaag actaaataac ttacttaaaa aaaaatagcc acccttctc     7440 agatagcctc taaagacttt atgctgtttt taagccttat ttttaaatta ttttaaattg    7500
gggtctgtgt aggcctgtgc acatgagtgc aggtcccct ggaggccaga ggttttttgat    7560 gctagcccgg gagttggttc tggaagtgaa tgtggatcct ctgcaagaac aatatagact    7620
tacaaaaact gagctatctc ttctgctcca atacagttca acatttttc tttttctttt     7680 ttcttttttt ctgttgaggg tgagaattca acaaccaag cattccaata tgagatgttt     7740
ccaatatctg atttaatgaa taatcacatg ttatgaaat aactgggta gtgtttaaac     7800 aggaagggga tgtttaatgt tcacattctc tgtggagtgc gtgcagtagc cccgtgcctg    7860
cagtagccct gtgccacact tatagacagt ttggctactt acatagttag ggtggtcatg    7920
aaaagacaac taagtcccctt tcatcaggct ccgtcttaac ttttccattt ctgattgaat   7980
ccctgggatc gatccagcag ggtgtcttgt cttggtcagc agctaggagt tattttgggg    8040
gaagggatgc tgcaggctat tttacagata attatgggtt tcctgtgcag aactgtccct    8100 gtagggctg gagcaagtga tgattctgtg attaagagca cttcctcctt ttgcagagga    8160
ccagtgttgg gtccccaaca cccacaggga agtactcctg attgtcttta tctccaggtg    8220 ctgggggca gcgcctctga cctactgttg cctgcaggtg cccttctcat gtgggctgcc    8280
cttgccctta ctgtctttgt ggcttcgtag agaatgatgg gaaaaaattc caagatggta    8340
gtcccactgg tgactaaagg tgtttagtag tagcttttc ttaaaataca gttggtgagc     8400
aagatagtgg tgcacacctt taatcccaac actaggagg cagaagcggg tggttctttg     8460
agattgaggc tagcctggtc tacagagtga gtgccaggac tacacacaca cacacacgca    8520
cacacacacc ccagaaagct tgaagttgta gttttacgaa agtgtattta accgtcagga    8580
ctaactatga tctttctttt gggctggtag ctgatggttt ggtttttttt ttttttagatg   8640 ggcatctccc acagcctggc ttgggatttg ccttgtagct caggtcggtc tagaactttc    8700 aatccccta cctcaacttc cactcctaat tgtccggcat ccttgaagag catgtgtctt     8760
gattttctgt aattttgaaa aacttggcct cggattttat ggcttactta tctttatgtg    8820
tatctttatg tgttttgcct gcatgtatgt atgtgtacca tgtatatgtt tagtgcttgc    8880
agagaccaga agaggacttg cggtcccctg gaaatagagt tatctacgtg gttttgagct    8940
agcacccagt ggtcttcact tccccgtgg ctctccagcc cttggattaa atgtggaatg     9000
tgctgtttgc ttgcttgaag ccaccatagg cagtgacagg ctttgtggac tttctacact    9060
ctgagaataa atgaaagtcc acttgcttgc tcttggctgg gtcaagtcag ggagctaaac    9120
tatcacatac ctcctctta acttcttgtc caactaaaga atcatgaatc ccaagccgtt     9180
tctggacaga gagaattcca ggttatggtg accatgtttt atgaggatgt taaaaatagc    9240
tcctaaggag gatgctgaca gattcaggaa ggagaacccg gcctcatgtt tatttgggtg    9300
ttatttatgt agcatgttcc tgagacatct caatcctgag cactaaggaa gtcaacacat    9360
tgtttcctaa ccctggaact tgttttttcac ttcttatacc tgacagttta caaatactgg   9420
ttcccccccc cccccatgtg tggccaagtg ttttaaaggt atctaacacc gaaaatggcc    9480
aatttggtgt gctgttatag atcaaaagga gatcttgag actagagatc tctgtcaagt     9540
ttattctctt tggaaaccct tcaagttcac attgagagct gacagttggc tagccctaga    9600
```

```
gtcatgtggc ttgcttcaag ccgcctctcc cccattccac ctcaacccct tggactgcca    9660
ctaagactgt tgcttagctg attgtagcag gtaccttgct gaatgtgtaa cctgtataga    9720
ttatgtgttt cagatttaaa accactcagg tctttaaaga ctaagggatc tgatccgaca    9780
tttgacttaa aattttaagt agaaactaag taaagttgtt ttgaatagta tgtgttgtgt    9840
tttctggagg tacagtctca taggaaatcg cccttgggtg ctgagtttga atgtgcctac    9900
tatctacttg accttagtca agtgagataa cctggttgaa attccaagat aatatctgtc    9960
taaattgcac agattgaata cacactggac tgtagttcct ggcccagtgt aggcgcaggg   10020
taagtgctga tttcctccca ccccacacct tgtcaaact aaataaaacc cacatctcaa    10080
agacctaata tgatgcttgc cttgtaatct ataatgataa atgtcagatt ttcagacctt   10140
aggccttcct ttatccaact cttttttttgc cctcgggttt ttgcaagccc cctggtgttt   10200
agacatgtga ccctttatct gcttacagtc taggtgttca aggttgactt tttttttttt    10260
tcttctgtta aggaagtcaa ccgtagccac ccagcacata gtgagaatat gtcatggtca   10320
tgggtatatt ttggcaggag agtcctctgt ttgaggtttt caaataatcg atgtaggcca   10380
gtgaagggtg gtagagaggt tggtgtgagc ttggttgggt gtgttgggtg tgagcttggt   10440
tgggtgtgtt ggatgtgtta tagtgtgctg tgccctgtcc aagccagtga agaacccatc   10500
caccattgca ggtgttgctt gtcttttgcc atcttctcct gtaatgccac catccatttg   10560
cctgccaggg gagctaggtg ctgggcttcc ggtgggctgt atggcaggga gttcacagaa   10620
ctgtgctggg gtccagacta gtggaagagc tggacattca tgtgcatggt tcctctaaga   10680
ggggcttgtg atggcagagg ctcagggtga gatcgtgtcc ttcaactcag tccttgggct   10740
aatgatggtt tccatgaaga caccttagct cctgctcttt gctccgtgcc ttgtgataag   10800
atgctgaagg tgcagatgct gagagcgcca ggcctttatt aagtgcctgt aagcggctca   10860
catgtgctag ggatgttgac aaattgcccc ttcccaacaa acaggcagat cccaggatcc   10920
catttcatga ataaaatttt tgcaattctt agagatgctg tggtttccgg acaccttcac   10980
agtgaccaca cacccaccct ttaggtgaac taattggtgg aagatggatt tcacagctca   11040
ttcctccttc ctcagcaaga ggatagatat ttgatggagt gttaggcacc cctcttgttt   11100
tttttttttt tttcacccct actttggact ttaaacttca gaggacaggc tggttggttc   11160
tgtttctcct tcacctcccc acacccactt ccttaagtcc tttgaagaag agtttcaggc   11220
aataaaaatt ttctagcact tatattctgt agttctggtg cgatgtaggg agttggtcca   11280
taccctctgc taccgtgggg accagtggga cacagcacag agtcctagac gctgacttat   11340
gctgagtcac tggagaaaag ctcagaacaa gaagggccac cttgctcctg cctgactgtt   11400
cctcatcgtt aggtcttcct ttcctcggat cctccagacc ttagcttcat tgagttgctg   11460
ttttgatagc atttcaagct tctcctttca gcatttcttc cttttttgcaa caaggtggga   11520 aatcaaaggc cacctggact ggactacctg gaactcctc aggctgtggt catgaaaagg    11580
acaggtgtgg aggcctttcc gggaactttt ttctccagag attagggact cacctatctt   11640
ctctccatct ctatctcctc ccctctcccc caggaggaaa aagaaaagaa aaaaattcca   11700
agaacgagaa gtgtggccct aggggcaaaa gaagccagga aatgaagccg tttttaaagc   11760
cagcaaagct cactttggtg actttaaaaa aaaaaaaagt gacctctggt cgcagctggg   11820
tatggaggtg acagtgactg actaggatac tgatctttgt agaggtcatt tgtgaaatgg   11880
gtggggatgc tcagagacag caggtatgaa gtaaggcaag gtcactgctg aagggaaaga   11940
```

```
cccacccaca tcagcttccc tcagagctgt acagcctttg catataacga ccacttccca    12000
ggctggtaga gagaagatgg catctctaga tgtgcttttc tagtctcagg gtaattagtt    12060 cccctttgagt cagtttccca acttattggc tgattggttg acctagagtc tcatgtagcc   12120
cttgaacgtc caattcttct gtctctacct cctgagtgct ggaattacag gcaggcacca    12180
ctttagccag ttcccatctc atctttgttg tagaaaagtg ttcacccttg aagggdtggc    12240
cagtctgagg aagctgcacc gcgctgtagc ttccccttga cgtctctttc ctggcacttc    12300
actctgatgg ctttcttgcc tagccatcat ggaggcaagg aaatggccag ggctgagagg    12360
ccagaaaacc cctgcttctc ttgggcagag taatgatgac ttccctgcct ggcacagtga    12420
cacaccttgt cctcgggaag ccacaatgtt tgggcacctc gcctggatct tcctagactc    12480
agtggctgag tctgaaggga gccactttc agatttgctt gctttctgaa agccttccct     12540
ccaggcaaag ctgaggtctg tggggcagga gaggaaggtt aaccatggtg ctgccatctt    12600
aatttggaac ttccaagcag atgtggcttt cagtcctcct ggatggcatc ccaggcaga    12660 ggcagagagt cctgtgtcca tccgtccgtc cgtccccccc aacgcaaaac actacagaaa   12720
agtgatcctt ctggctctgg cctaccttc taggtcctgt ggtgttaacc agctgggatg    12780
gtgtggcccc ccgctccaga acgatccctg ccctctcctg aaagcagctt tctgtgaggt    12840
cattgctgtc cagcaacttg cggaccattc ctccagcaga gattcccttc cagcttccat    12900
gcaggcctga gctaactgag ccccagcaac aggatcaaac ccattccaag aggaaggcca    12960
tctgttcctc agcctccagc tgctggccct tcatttgcaa ttggctggga agctttggag    13020
gggtcaggtc ctggggacac atctgcagtc tctgaatggt gttataactg gggtcctgct    13080
gagcagagaa aggccaagcc ctttaaataa acttgctgaa caatacccc ccaaaggtgt     13140 agagtcagag aagcaggagg cagctttgcc ctttagctaa ctcttaacct tggttttgta    13200
gccagggcac ttgaaaacta tttctttatt cagaaagtac ttaccaagcg gagaagggag    13260
gggctgctct gaacaaggaa aatgtcatat aggatttggg catcgatctg ccccttaagg    13320
gaattagagg gcaaatatct ccacttgagt gtatgccatt tattgaatat ttacctcagt    13380
gtcaaagagg tgagcttgtt ccagatgcag cttgtaaaga gccacaggca gcatgaagtc    13440
ctctcgaact tgcctctgga atgcagttca gccttgggaa caccagccaa tctccctagt    13500
tcattgcaag caggtcccca agctgtagct gcttaggtc ctgtggttct tgggcctgtc     13560
tgtagtttgg tgttagggcc cttatttcct gcatccgggg gcctatgata acttagccta    13620
atgctctagg gactttctat agggaccagg ctgtaatcgg gcgtgtgact tcattgagtg    13680
gatgaatggc agttatgcag gtgttgtcca ccttggtttt attgacaggg tctctccctg    13740
actgggaact taccacatag gttaagctgg ctggtgagca ggctccctgg agatgtctct    13800
gtctcattca ctacatctag gtttttttgt ttgtttgttt ttgttttttt ggttttttt     13860 gttttttgttt tttgttttt tttttttttt ggtgggttct gaggaattaa agtgatgctt    13920
gcaaggcaag aactttatgg actgagctat ctgtcagcta tctgtcagcc cagccccag    13980 aggtacaata acctgtgggc cctttggctc actggtttct tgaagcaggt attaggcctg    14040
gtctgtatga gacggagcct tcaggacctg cagatgttta gttccacttg agaactttgc    14100
aggaatcctc gctcagggaa ggcgtgtata taagatgtga cagatttatt cacttgaaag    14160
aaagccctgg tttggagtca gaggcatgca agtggatatt tcatggggc catcttaacc     14220 ctctgctgac tcatctactg acctgttaga atcaggctgt gacccataaa accaagcccc    14280
aggtggctcc cggctgggtg aatatgtctg cagagcttca ggtagagcat ttgccctact    14340
```

```
gtgcacagag tgtttcctct cagtgtgctc ctcacatcag ggtcagtgag ggacttaaca   14400
gaaagccttg ggttccctct ttgtgccacc gtttgccagt agctggcctt tctggtgtct   14460
cagggacaga gggggccgtt cagtacgacc acgttcattt tggacagcag caagccttaa   14520
gctttggtct ttggacaaag ggtttctgag ctggcggtgc catcctcagc tgggagccca   14580
ggagcaccca gccagagcac tcaggccatt caggaggctg accctgggtg gaggtcctta   14640
tgcacgataa acctcggtca ttgcgttcat tttccttcct cccaccttct cagaatgtct   14700
ccacgagaca gttgggtgag aatgaatatg tctgcgtgtt ctacgtggat aaaacatagg   14760
ctgtgacatc atggggatgg ggtgacggca tgtgtcataa tgggaaactg gaaatcttat   14820
agaagagaca tttaggtttt gaaaactgca caggagcctc tcaggtagag aaacagttta   14880
ggtacaggga acaggacag gggacagagg acagacatac cgtctggcta ggcaagccac   14940
catgtgaatg aacgggggga agaggggaaa ctgggggaat gtggtactcg gtaatgatgt   15000
aaagatttcc tagagagaca ctcattatag gttgggtaca ttccattcag gcctttgcct   15060
ctttaggagc ccctatagca ttccttgatg ttgtagctac gaggagcagc aacctggccc   15120
caaaagagat tcaacagact ttcccagtgg cttttgtctg cctgtggatc cagccctaga   15180
tggcaaggtt tgggactagt gtgtcctaag gagtcctgca gaccttgggg agcctgtgct   15240
ttctcttgca agtgcgcctt caggacgcag gaggcctggg cctggctggc cagacctcgg   15300
atacagacgc ctctttgtgc ctctgagcca cgagtgctgg gtactttgac ataacttgta   15360
atgccagttt ctacttcctg ggtgctatgg aatctaatgg ctgagttctc tgggacatgc   15420
tctctcagaa caaaaggttc cattttccag ttcttgctca agcaaagcat caacagctag   15480
gggatttgtg tagctgcgca gatttgatct ctcctcgcgt cttggtggcc cagtgggaat   15540
ttcagtcttg ggagtgtatg aattgagtgc gtatgttgtg accaggcgcc tctgtcattt   15600
ggacactatc gtcgcatgac aggattgggg gggagagagg tgcgggtggg taaggagcta   15660
agctgccgcc gctttgagtc taggtaccgg gtgacacaat gattcttagg ccctttttgcc   15720 ttttctgcat ttttatttc tcctgggctc aggcataatt tgtttcaaac tggagggctg   15780
tccaccctgt ttctcaaagc caaacctaaa ttacgagggg tgtgcctaaa tatgaaatat   15840
gtaatggttc ccatattgaa acatttgcta ccttctagtc ctctccgatg ggcggcttga   15900
gccagcccag agtttctggg gctgtccgac tactgcagct gaggtagcta ttggtgggg   15960 tgatgctaac aggaacgtgt ctgaagagat gctccagcta ttggttgtaa acaaagagcc   16020
tgggcagcct gctcacctct ctcctctccc tagcctcacc atcctgccct cccccacccc   16080 cttttttat gcagccgtat ttcttgaggt tgaaaacttc catctttgtc ctgtatgggt   16140
gttggccccc tcctctcttt caggatgagt tgtacagagg ccttataagg atgctatcag   16200
gatgtgcaag ttggcacact ggtaaagggg aaactttgaa agagtaggag ctgcagcagc   16260
cagctctgga tgtcgtcttt tgtgtctggg acaaggctag ctaggccgc tcttcttcct   16320 gactccacca aaggacccca ttgtccttaa tatctttat actgaactct ggtgccagct   16380
ccatgctgac agtgccatgc aaaaatatgt acaggagagg ctcttccaag gtcccagtct   16440
tgccaggtgt caccggtttc taaaagccta ggtggacatt ccagtaccat gtgccctgca   16500
ttctgggtgt ccttgatttg aagttacaaa gaacctttca agttctgtac cctgttctat   16560
ggccagtgac cacagctcac caggcccatg gagtggcagg gcatctttat ggctcggagg   16620
gcagagtggg tcaacccttt gccactcacc tgttatgaac ccagtgtcct gtgactttgc   16680
```

```
agtgacattt ggcagctcga tccccattct ccgtcaagac ttttggcagt cctgtggctt    16740
tgctgtttat ttgtcttgta ttagatggca ctgtctggga gaacgccggg ccatggtatt    16800
gtcctcgtcc cagggttcct gtgcagtcct actgggctag aggagtgctg ggaggtgggg    16860
acagcttagc tgggcagccc cgtcccttga caggacatgc ctgctgaagc tgtgccttct    16920
cctccaccct cctcctcccc tttccctcct gcctcctctc tcctcttctc tcctcatcgt    16980
cccctttctt ccttgtacgt ccctcttctg ggtgaatcta ctctgattct gctttgtcct    17040
ttccagaaga atgtgttttg ggatctgatt gtgccctgtg gggagccccc ctaagtgggg    17100
ctgtttgagg taccccactg tatctttaac tcagatcctt tagacgctga ctaaagaagt    17160
cattctgggg acaccctaga agtggcttgg tgtggtgcga ggtgatttgt tgccccagag    17220
gtggttggca gaagtggctc cttctccctg cgatggtggg aagctgccat gtgatctgtg    17280
ggagacgatt ggccagggca ggacttggac gcccatctgt tctctgtttg cagttgggcg    17340
ccatttcaga aaccacaggg gaaaagttta taggcaaaca tgataaaaag tgacagtctg    17400
aagtgctgct atcgctggct tggcaactta aagcattacc tgaagcagct tctaacttcc    17460
agacgctcta gctgcaacgg gaaccccaag atggccatcc tgtgggcgct ggggaagatt    17520
tcgtttgtgc gcagtgaggt gtcttagtct cggccccatc tacttcttga aggctccctt    17580
tctagggtga cttcacgaat agcaaggtgt catacccctc cccctagct tacaggaagg    17640 taaatacaag ctgtcactag tgacatcagg tgaggtccca cccagaggtt gtgacctact    17700
tggatctgta gaaggacttg gagaagggtc aggaagattc tgcctcagtt tccctttcgc    17760
ctgggtctga agcccctctc atttctaaat cccctattacc tcccagggaa tagtggcttg    17820
aggaatcttt gggaagaaag agggctcatg gcagggtaac agtcagccac gtgtgcggaa    17880
ttttaaagac agaatctcac tacatagccc aggctggctt tgactgccct cactcagtag    17940
cttagtaggc ggtaaactct gaagccgatg caggctttga acttatgatc ttcctaaccc    18000
accatgtgcc accatacccc accactgttg atgttttcat tattggattt gatgctgtga    18060
aggaacccct ttatcttttg gtttgtttgt tttctgagta tcagagtagt cagctcactg    18120
aaaatatgac cagtatatag gaaactgctg gcatgtctca agggtttgta acctgtgggt    18180
agaaacacag ctaagcctcc acacaggaga gcctctggcc actgttgtgt tgtcgcagg    18240 tagaaacagc tgagcagagc cttcccagaa agtaaacatg tcgccttgtt tgttcagaga    18300
gtttaggtaa caatgacagt gtatggccca gctcccatgc atctttccaa gtttccattt    18360
aattatgaaa aatgtatgag aacagacttt ctgtctgcgg aaaccctga aagagcattt    18420 ggtgcctctg ctcgtagctt ctggaacttt ctccccactg tgctgtgcag agtgcagagg    18480
gtggaacttg gaagcgtgtg ctccggtaag ccacggcatc agaaatgtta aatccaggaa    18540
atgttgatat tgctataaaa gagactgttt ggatttccca gggagttcct tgtcctgtgt    18600
caattgtcac gtgttacaca gagcagcttg gcagagtcgg gcaaggagtg gcctgtgtgg    18660
agaggccatc tgagtgggag agacaggtgg ggtgtggcga gcacagtcct tggtgccttg    18720
gccccttata ggacactatg aggtggttac aatatggagt tgtaacacca caggactctt    18780
aagagcaggc agtgattggg aggagccagt cccgaagcct ggtgaaggat ttaggcacag    18840
aagagaagcc tttagctctc aagtctccag ggctaggcgg gagcaggatg gcatctttc    18900 agcatgccac ttgggttcca tgttcttagt gccctggtcc gtgatgtatc tcatgtgtga    18960
tccatttgca gggagctacc aactgcatct gtgtcctggg atgctgttgg gttggcttt    19020 tcttctcacc cccttattat aatcctgctc tctcctgttt cttccccctc tacggtattt    19080
```

```
gaccttctcc tttctttctg ccctttcttt tcctgtattc acccaatctc cctactccct    19140
aggatcacca aggaggaggt aacattgctt tctgctgacg ctgctgaccc ctaagtgggg    19200
cctcttgaga aaggtcact agggagttgt gcattctgcc tatccaaggc agataccttg    19260
gaggaggcct tggcgttagg atggcttgat ttcatagata cttatctttc tgacgtgctt    19320
gcagatgata ctctatactg tccccaaagc cagtcgtctt cctgggaaac tagagagttt    19380
cccattttgc ccatgccaac ctggcctcac cattgactga gtgagatggg agcccatcag    19440
tgaaagtctt gagattaaaa atccagttgt ttctgaagac agtggagcac cacagttata    19500
gcttgagaac aacggcggat gactgacatt ggttgtggct ggaagatcaa gtatacagcc    19560
ggtggctccc aggcacctcc cgtataatgc cttcttgtat gttggtggtt ggggatcttg    19620
tggctgagag gctatgcagg gcagagagga aatgagccca gtgtccctgt acccagggca    19680
gtgtcccttt accaaacatc cagtgtcctg tcctacctga gacccctctt cttctgtgtt    19740
cctcacagca tggtgataca gtatggtaga attggtccag catggtccag tagtgcagct    19800
aaatttcaat gagtcttggt cctttgttga tgttgggtgg aggaagggtt tctccgtgga    19860
tggtgtagac tttaaggctc catcattctt aacattgtac gaatctttgg tttaaagatg    19920
ttaagaccag actggcagat ggtatgagac ttaggttcaa atggaacccc cctttcccct    19980
ccttatttct cttcctcatc cttaaaaata tgaacccttt gttttacttg ttgttgctgt    20040
tgttcattat tctcagtgtt agtgtgtgtg tgtgtgtgtg tgtgtgtgtg tgtgtgatgt    20100
gtgagtgcat gtagacaaat cagccatgct gtgtaaaggt cagagtgcag tctggtagag    20160
tcaattcctt cttcctcttc taccttttta agggtttctg ggaaccaaac ttggctttag    20220
gcaagcatgc cttcctcctc ggagccatca ttccagaact gcctctccct cattcactta    20280
gccactcagg tcagctgcct cttggtttaa atgggcaggg aaaggcctga gctgagaccc    20340
ttccaactga attctcaatg tctttcaaac ttggttctgt gtagtgccac agggtgtctg    20400
ctacttcttg gaggagactc ctatcccctc ctgcaacaga agctgaaaca ccttcggtga    20460
ggggccacgc tatcagtgtt tggggcttgt agaccatgag attttttttt ttttttcaat    20520
gactctggtc tgcccgtata acacaaaagc agccctagac aatacatacc caagtatgta    20580
ttgagtatgg cactgctcca agaagtcttt gtttacaaaa gcaagtggct gacttgtccc    20640
tcaggccatg ctttgctggc tcctgctgcc cacggggcct tcgcccaccg tttccacatg    20700
aacggctacc tacctgcctc acccttaaga ctcccttaca cacttcctat tttctctgag    20760
gtttttcttc actttcattt gccccactgc aatggagggt ccaccagggc agggatatgg    20820
ctaccctcct gttgcttcct gagtgtacag aacaaagctt ggcctgtggt aggtatgcaa    20880
taaacagagg gcacatgaga taaacaagcc cttgaaacct tacctggctg tcagttgggt    20940
ttgctttctg cccctgcttt gtgtgtgtgt gtgtgtgtgt gtgtgtgtgt gtgtgtgtgt    21000
gtgtggttgt ggtggggttt tgtgttccatc aacttctgtt ttcttcccta tgtgggtttt    21060
actttttgtgt tcctgtactg ttaacatctg tgcccctctt ggctgtgtgc atttgaagtg    21120
ggggtcccct gtgagaagcc tcaggcccct tgtgttggct gctgctgcgc ttcttggacc    21180
agatgtttat taaatagcag gactgaaaca tgaattgact gtattctagt cgtgagagaa    21240
tttgttcttt ggagtgggct ctgggcagaa taatcgcctt gtgatgctgc tgcccagatc    21300
tggaacctgc ccagtgtggg gaaggaagca ttgtgttttc caggcttggg actctgggta    21360
ccattcacag ctctcactgt gggatgaaag cttatttcat gagccctcgt ggccacctct    21420
```

```
ggccctgagc aaggtcagga gcttccttcc tctcactttt tttgggagaa gctgggaggt    21480
tggatcatag ttggtttcat tctgccctgt ctttagagga aggcaatgtc tgccttctct    21540
gtgtacagca aagatatcca gtgtagggat gggcgtgggc acaatgacct atcagaactg    21600
agctttctga tgtgaaggtt tcctctggaa gtcaggacac ccataggcaa tgtgtctatt    21660
tcagtgtttg gaggtatagg gtaggcagat ggactttaga gtgggagaga ccccttttagt   21720 ttccagccag gtgactgatg cagagtgatg gatcatggag ggccatggtt gacctgggca    21780
tcagaggagg aactgggcta acgggagtg agagggagga ccttgtgttc ataaagaaga     21840
gcaggatgct tgacggagat cagggactct ggggtagtgg tgggttggtg ggcaggatgg    21900
atctggctcc accagtggaa tgctgggtag tagtacatgc tacttatcca gtacatgtag    21960
tctatgtgta tacatggctg gtttatggta tagggccatt aagtgccagt aattccttac    22020
ttttctttct ttggacgtta aaggacccccc agcatctgtc attttgagga agatggaatg   22080
tcccagctcg cccagaacag atctagctca gtcctgatcg ggccccaaga gcacataaaa    22140
acaatcaagc caatagctgc ctcttcccaa gtggtgaaga gtaattttgt agatgggtct    22200
gtttgcccct tgaatttgag acattttatt tatattgaaa agcttggttc tgtgagaaca    22260
ggcaaagtga aatatgaata agtagctaag tcagtgtgag aacgtgtatg tacgtgtgca    22320
tgtatcacat atacagtcat gctggatggc tagcttggaa atcaacttta cagttttctt    22380
gtggattttt cttccacttt agggtttggt tggttttttaa agcccttattt ccagtatgtg  22440 gaaatgagcc aacccaggac agcttccgct ggatcgtgga cagcttctat ggccgtcgac    22500
gtgtacactc gagataactt cgtataatgt atgctatacg aagttatatg catggcctcc    22560
gcgccgggtt ttggcgcctc ccgcgggcgc ccccctcctc acggcgagcg ctgccacgtc    22620
agacgaaggg cgcagcgagc gtcctgatcc ttccgcccgg acgctcagga cagcggcccg    22680
ctgctcataa gactcggcct tagaaccccca gtatcagcag aaggacattt taggacggga   22740
cttgggtgac tctagggcac tggttttctt tccagagagc ggaacaggcg aggaaaagta    22800
gtcccttctc ggcgattctg cggagggatc tccgtggggc ggtgaacgcc gatgattata    22860
taaggacgcg ccgggtgtgg cacagctagt tccgtcgcag ccgggatttg ggtcgcggtt    22920
cttgtttgtg gatcgctgtg atcgtcactt ggtgagtagc gggctgctgg gctggccggg    22980
gctttcgtgg ccgccgggcc gctcggtggg acggaagcgt gtggagagac cgccaagggc    23040
tgtagtctgg gtccgcgagc aaggttgccc tgaactgggg gttgggggga gcgcagcaaa    23100
atggcggctg ttcccgagtc ttgaatggaa gacgcttgtg aggcgggctg tgaggtcgtt    23160
gaaacaaggt gggggggcatg gtgggcggca agaacccaag gtcttgaggc cttcgctaat    23220
gcgggaaagc tcttattcgg gtgagatggg ctggggcacc atctggggac cctgacgtga    23280
agtttgtcac tgactggaga actcggtttg tcgtctgttg cgggggcggc agttatggcg    23340
gtgccgttgg gcagtgcacc cgtacctttg ggagcgcgcg ccctcgtcgt gtcgtgacgt    23400
cacccgttct gttggcttat aatgcagggt ggggccacct gccggtaggt gtgcggtagg    23460
cttttctccg tcgcaggacg cagggttcgg gcctagggta ggctctcctg aatcgacagg    23520
cgccggacct ctggtgaggg gagggataag tgaggcgtca gtttctttgg tcggttttat    23580
gtacctatct tcttaagtag ctgaagctcc ggttttgaac tatgcgctcg gggttggcga    23640
gtgtgttttg tgaagttttt taggcacctt ttgaaatgta atcatttggg tcaatatgta    23700
attttcagtg ttagactagt aaattgtccg ctaaattctg gccgttttg gcttttttgt     23760 tagacgtgtt gacaattaat catcggcata gtatatcggc atagtataat acgacaaggt    23820
```

```
gaggaactaa accatgaaaa agcctgaact caccgcgacg tctgtcgaga agtttctgat   23880
cgaaaagttc gacagcgtgt ccgacctgat gcagctctcg gagggcgaag aatctcgtgc   23940
tttcagcttc gatgtaggag ggcgtggata tgtcctgcgg gtaaatagct gcgccgatgg   24000
tttctacaaa gatcgttatg tttatcggca ctttgcatcg gccgcgctcc cgattccgga   24060
agtgcttgac attggggaat tcagcgagag cctgacctat tgcatctccc gccgtgcaca   24120
gggtgtcacg ttgcaagacc tgcctgaaac cgaactgccc gctgttctgc agccggtcgc   24180
ggaggccatg gatgcgattg ctgcggccga tcttagccag acgagcgggt tcggcccatt   24240
cggaccgcaa ggaatcggtc aatacactac atggcgtgat ttcatatgcg cgattgctga   24300
tccccatgtg tatcactggc aaactgtgat ggacgacacc gtcagtgcgt ccgtcgcgca   24360
ggctctcgat gagctgatgc tttgggccga ggactgcccc gaagtccggc acctcgtgca   24420
cgcggatttc ggctccaaca atgtcctgac ggacaatggc cgcataacag cggtcattga   24480
ctggagcgag gcgatgttcg gggattccca atacgaggtc gccaacatct tcttctggag   24540
gccgtggttg gcttgtatgg agcagcagac gcgctacttc gagcggaggc atccggagct   24600
tgcaggatcg ccgcggctcc gggcgtatat gctccgcatt ggtcttgacc aactctatca   24660
gagcttggtt gacggcaatt tcgatgatgc agcttgggcg cagggtcgat gcgacgcaat   24720
cgtccgatcc ggagccggga ctgtcgggcg tacacaaatc gcccgcagaa gcgcggccgt   24780
ctggaccgat ggctgtgtag aagtactcgc cgatagtgga aaccgacgcc ccagcactcg   24840
tccgagggca aaggaatagg gggatccgct gtaagtctgc agaaattgat gatctattaa   24900
acaataaaga tgtccactaa aatggaagtt tttcctgtca tactttgtta agaagggtga   24960
gaacagagta cctacatttt gaatggaagg attggagcta cgggggtggg ggtgggtgg   25020 gattagataa atgcctgctc tttactgaag gctctttact attgctttat gataatgttt   25080
catagttgga tatcataatt taaacaagca aaaccaaatt aagggccagc tcattcctcc   25140
cactcatgat ctatagatct atagatctct cgtgggatca ttgttttttct cttgattccc   25200 actttgtggt tctaagtact gtggtttcca aatgtgtcag tttcatagcc tgaagaacga   25260
gatcagcagc ctctgttcca catacacttc attctcagta ttgttttgcc aagttctaat   25320
tccatcagac ctcgacctgc agcccctagc ccgggataac ttcgtataat gtatgctata   25380
cgaagttatg ctagtaacta taacggtcct aaggtagcga gctagcccac cttgccttga   25440
gaatggtcgt cgccttttgg ttcctttggt tgtgctatga tgcgtcagtc tggtgtgcta   25500
actctatggc ctgcttatct gttcctcctc ctgtgatctg caatctagcg cctggaagag   25560
aaaaggagat tacagcttcc ccagactacc tggagatagc tatttactgc atagggggtct   25620 tcttaatcgc ctgcatggtg gtgacagtca tcttttgccg aatgaagacc acgaccaaga   25680
agccagactt cagcagccag ccagctgtgc acaagctgac caagcgcatc cccctgcgga   25740
gacaggtaac agaaagtaga taaagagttt gaagaaattt actcccctcc cccacccagc   25800
cagctcttgg atcttcttcc ctctgatttt cccctaact tctgtgagct ccagaactgc   25860
aggcaattct aatctgccac tgtgtggagg ttcagtcagc ggttgggact aaagagcatt   25920
aagtcacaat gctgctctgg gcttggtagg ctggctctgg ttttaaagga caagagtgtg   25980
aagactggag ctgcccagtg ggatgggcag aggaggccat gccctctgcg cccctcaagc   26040
tcacggctcc tttgggagaa caagcatttg gtctggctcc attgcttctg tatgaggcca   26100
gatgttcggg ttcaagtttt acccttcata ggaaagagag tttaattttc tttgatttac   26160
```

```
tattttaagt agagatcaga aacagaggat ggaggtatac ctgaactaat gcttgcataa   26220
aagtggtctg tgatgtcttc taaactgggt tttggctgat tttgtctggt ttttaaaacg   26280
ctgtatgcgt atagtttatt gttacaggtt tggctaggga ttcagtgata ggatgattgt   26340
gtgtgtgtgt gtgtgtgtgt gtgtgtgtgt gtgtgtgtgt gtgtgtgtgt gtgtgtttgt   26400
atttaggtta taagtacatg tgtgcaggtg cctgtggaga ccaaaagaga gtgtcaggtc   26460
cactagtgct agagtttatc agcataggtg gtaggaattg aactctggtc ttctagaagt   26520
gcagcaagca ctcttaacc actgagccag ttctccagcc cccagatacg atgattgcta   26580
tgtagaacag ggagaaaatt accttaacc ttgagcttga tctttgatgg ctggctttgg   26640
gggaggtaag gcaatagaac cttccctgtg ccataaaaca aagcccttca aggtggata   26700 aggaaaaaat gcttgacttc tgtacttgct cctggattcc aagagccagg catgtgtggg   26760
tgtaaatctt tatgataaga ttcggaactt gattctgata agattgtcac tatttttttt   26820
aaattagcaa tggaaatgaa caacctggcc tgtgctatgg ggaggtgcat cttagtgttt   26880
gttaaaactg catattcatt agtttcaacc ctagaaaattc ttatttagta cttcttgaat   26940
ggatctgtaa gagtctgcat tttaaacact ttctcgggtg atactgtgta ataccttaag   27000
aatctctggg ttcaacccaa ccctgccttt cctgggccct ttctgtggac aaggtgggaa   27060
ctagcaggtc agtagtggct tggacacagg gccttggctg ttctcaacct agcttcacac   27120
tacaggctga gcaggtcctt gtcaacgtcc ttgaagcctc gtttccaaca ggtgtttctt   27180
gcagagggtt aagatataat ttggagcata tgtcagatgc agcctttggc cagctgttga   27240
atgtggagtc aaaaaggctc agttgggttc cttttaatcc tgagaatgct gtgctacttt   27300
gagtgacacc actgtcattt gtgggaccat agaagctaga tggtgctgaa gttaaagttg   27360
gttgcctgaa tgagttgctg gaagagtcct taataaaact cttacctggc tagatagtgt   27420
taaggcttca ggctgaatgg ccactccttt ggccactcct ttggctactc cttcacagcc   27480
tctcctgatc tcttagccct gggccattct taacatctgg actctggtct agggagttta   27540
agtaaaggga gcaatgtcct gtctcatttg tttttataat agagaaaaga agtaaaatcc   27600
ataagttgag gtagataggc cattgacccct taattatttc atcatttaaa aaactgatgt   27660
gtgtgtgtgt gtgtttatac atgtgtgctg gagctcttgg aaagctggaa gagagcactg   27720
gatccctcag agctggaggg ccggtagttg tgagctctct gatgtggtgc tgggactaga   27780
actcgggtcc tctgcaagag cagcaagcgc tcctaatcac tgagccatct atctctccag   27840
cctgcatcac ttttaaagaa aactcttct atttctccat tttccatttc catttccatc   27900
tttttacatt tatatattac atttatatat ttatgtagct tgggcacgtg tgcgtttgtg   27960
tgggggcatg cacatggcat agcaaggtta gtgaaggtcc ttttgaaatg gtggccaggg   28020
gacaacttac atgggagcca gcacctttct ctaccacgtg attcccagga atcaaacagg   28080
tcaggttcag tcaggtcatc gtatctgatg accgattttg ttgactccat cgcttttaaa   28140 gaaaaaaga attaacacct attacagcgc tcttcctttt gcttcatgtg aaaagacag   28200 aggccctgga gttccaggc acatggattc agcatgtctt cctttctgtt tgtccaactg   28260
agtttcttca tttctgtcc acctaagctg tccattttgt ttgttttat attccctgtg   28320 tgaccggagg gaaagttgt tttttttttt tttcatttac ctcccttttct tcttgtattc   28380 attgttattt actgagtgca cagtttcttt tagtgcatgg gcctaaatca ggactcttgg   28440
gctgggagtg tggctcagtg ctggcatgct cgcctagctt gtccaagcct cagtatcacc   28500
aaagaaaata attaagccag tttcgtgtca gagaaagcct gcccatttgc cactggctgc   28560
```

```
aaggttagtg aaggtccttt tgaaatgttt cttcatgctg acgctggata acaaatgtgt   28620
gaggcccagg ctctctgcat gaggaagcct ctgggagata aatgggttga aaaggtactg   28680
ataatacccc agcatttcct agaagtcatg gggaagtatg gtactaactg cctcttccca   28740
aaggatttcc caaagcttag gccactggga ggaggaggag gaggaaaagg aggagaagga   28800
ggaggggaga tgcttatcat gagtctggat aaagagggtt ttgggctgta gctggaggcc   28860
tgcagatagg ttaatgacag agtgaattcc tcagggatgc caagcatgcc ttacctggcg   28920
acagatgagc ctgtaatcag atgtctggag gacgggtgct cccaggcact aagaggctag   28980
gctttatttt gtgtaggccc aagcttctat atgatgcagc atccatgccc tggcccttgc   29040
ccaggacggc gaggaggcgc atagcctctc tccattcact ccatctttgt ctttgttttta  29100 gaacgagaaa agttggtttg tttattcatg ctgtttttttt ccatgtgcac aagcgcgtgc   29160
tcggaaagtg tgtaggtgtg tacagaaagt gtgctgaggc caaatgataa ccttgggtgt   29220
cattcctcag gtgccgtcca ctccttactc tttgtgtgtg tatgtgtgtg tgtgtgtgtg   29280
tgtgtgtgtg ctaagtttct cacctgcttg cctgaactag ccaagtaagc taggttatct   29340
ggtctgtgag ccccagggtc ccaattgctc ctccttctcc tcctctctgt taggattcca   29400
agtgtcggct cccaagcctg actcttcttt tttttctga cagggttc ctctgtgtag   29460 ccctggctgt cctggaactc actctgtaga ccaggctggc cttgaactca gaaatccgcc   29520
tgcctctgcc tccaagtgct gggattaaag gcatggacca ccaccgcccg ctttttttt   29580 ttttttttt tttttttttt taatatagct cctagggatt gctctcaggt caaggaaggc   29640
aggcgttttg atccttcttt ctccttgagg tttgcttccc tgccctgaac ttgtttaaaa   29700
caggcatttc actttaaaaa ggtagggtct tttttttgt gggtggaggg ggtgggggt   29760 gttttctgta tcaaataaat tctttatagt cttttctagta aacattaatt ttgggagaca   29820
ttgtgcttgg agtaagatac gcaacttttt ggtgggacag cctggtaggt agcctgtggg   29880
atctctaagg aggagtcatc tctctcaccc aaggctagga ctgggcactt tgtaagcgct   29940
tgcgcacttg cctctacttc ttggtaccta gtgttaaatg gcaatagtca gtctagagaa   30000
gggcaccttg tgacccaact ggaccatcag tggtcactgg gcagtggtct ttgtgtactt   30060
ctgagtccaa gtggaaagat ttgccttctg tgatttccac aagtcccttg ttggggaggt   30120
gggccgtatg tgagtgcaga gcggggtgga ggaagccttg ttctgtggag tgcttgtttg   30180
tggaggagct ttcctgggta ggttcagctt cttttctggag ccagaagttt gcttagggca   30240
agatggagat ccatctgtct gtgtccagat gagtgcatag cctacccgat cccccagtct   30300
cacacaggac tgtagtgagt ttgttcccag cctcagccat tgacatgggt agctgagaaa   30360
accagagagc aatttcataa tgcgtttgag acccatggtt attcagggtg ggctgggggg   30420
aacacttaat tccagagctg ttctcagggc aatgtattcg tggtcttaga gtatatgaaa   30480
ctcagtgaaa gtgagtgctg actgcttagc atcccagcac cgtgacctgg aatctccatc   30540
gtacgaggtg tagtcgatcc agagttgcag tgtaccggtt ctgggaaaca tttgggcagc   30600
tggatagttg tggatgaccc gagtggagtc ttcgctttcc tagggatcga tcgctttcct   30660
tgtccccagt ttggcctgtc ttttctctca gcccctgaaa gacatgctgc cttggctgag   30720
atccacccta gacttttgct gatgagctat aagtaggttc agaacacctg agtcaggtac   30780
ttttactgtt gtgacagggc attcaagagt ccagaggagg tagaagctgt ctaagggca   30840 gtgtgagcaa ttacctagat tttgttatgg aaggaaaaac aaaacaaaac aaaacaaaac   30900
```

-continued

```
caaaaaactc cactcccaga aactctctga agcttggtgt ggtgcaggtt tttctgttgt    30960
ccatagaggt gtgtggggct agacttaaga tagaacacac tggccctctg ttctgatgtg    31020
gaaggctcca tctgctgcct gggagtcgga gggtgtctca agtctgctgt agtccaaggg    31080
catgtgtcaa ttctcaggaa taaagacaaa cttgactcac ccttccccgt actgtctttg    31140
cttccgcctg cgctgttgtc tgtgaggtcc cctctgaatg ttcagcttca tccagcataa    31200
agggagacgg ctatgacttg gtggctcttt aaaagaaaa ggggagaaaa cccacttcct     31260
ccgttaatct cccatatgta ccgtggaaat atatgaaaag cacatttagt taaaagcttg    31320
atttatggca cgtggtaaag agatcccggc atgtaaggct gccgaattgg agactgtgaa    31380
gagtgtgcgg cttctaaaaa accgcctgcc aagatttggg gtggggaatg ggggtggggc    31440
ggagcaacag tttactacag tgttagcgtt tattgtttat aagtgaactt ctaacagtgg    31500
gatgttttta agtgcgttga aagggaaact ccaaaatgga agtttctaga ttaaggattg    31560
agaactatct gaggagggaa gttataagta caagagaaag agaagaaagg aagtctgtaa    31620
tacagtggtg tgaggaacct tccaaggtgg gcggtggggc cacaattcag agggaaggag    31680
cccctgaaaa gccaggctcc tccagggacc cctgctgggg attttgccaa gccctccaga    31740
caggttgcct ttctgaggag aggcgagtga agagaaagcc agtcatgctt tatagcccca    31800
gagaggattt taaaagtata gtaaaacgca tggaggtaga attaagatgg acctctgtag    31860
acagggagag cagagtgtat gctcagagac tttgcgtatt ttcttaccct ttcccactct    31920
gggtgttttt tacaaaggta ttttccaggc ttgtacattg aacctgaatc tgcactgtgt    31980
attgaacaaa attcccacac atgaaggcag ttttacattt tgataccaat gtgcagcaac    32040
gactgccaag gttttttttt tttttcttcc gtattagttt agttttttt tttttttttt     32100 tctccccgtt ttccatttg aaaatgttgc ccttaaaacc ttgtggaggt gctctgttgt    32160
ggggtgggta tgcgtatggg aaacttgcac cccaggcctg tgctgtgcat tctgtttggg    32220
tcaaaggtcc tccacagagt agttgatgtc agactggatg gtaaatctct ctgttttgag    32280
gtaaccccta agtcatggtc accagcggga ccttgctgct ctatggtttt cttcttctcc    32340
tctaattcct acattaaaaa tatatatagt cttgcttact ggaactccag gctatcctgg    32400
ctggcagttt agggtcccat tttgtaaatc agactcgcaa ttcaggtgta tgccatctaa    32460
aatcagaaca aactcacctt gtagagcaga ctggtgagct atggctgtcc cagctcagca    32520
ataagcactt gatgctgtct tcattctgtc ctgctaactc tgagaccacc tgagactcac    32580 atagacccc ggaatctgac cttgacttca cggtaccatt gaccaggatg tagcctgcca     32640
gggcatcttg gccctgggtg atcaccaggt cacacattga aggatgcgga aacatcacaa    32700
aacagcctgg ggtgggggg acaaaaaaga agtgccatcg ggcgtcttgc tagtttctaa     32760
actgaagtct gcataattca accctgtgcc ttcttttcct gctgttcata tttattttat    32820
tccaaatgct attttggcta aagaaagaat gtctactaaa acacaaagga aacacaagac    32880
cagggtaata aaatctatat gatgtagaaa gttctagaat aagacctgtt tcctaccttg    32940
ctccctattc ttgatctctc actctctctc cgaaggtgac cactgctaaa tccttagata    33000
tctttccaga aaacatttcc tgctttgctt cccaagtctt gatctctctc cccaaagggg    33060
accatggcta aacccttaga tatccttcca gaaaatgcct gtggtcacaa cccatcctgt    33120
aagcctctat gtgctgagta ctgactccca aggacaggcc acagaagctg cgatgtgcca    33180
ctagcctctg gccattacca tcattcagaa ctgtggtctt ctgagatttc tcagcatccc    33240
ctcctcactg gtcttagcac acagtgggtc ctaacaacta agctaggaac tttagggtcc    33300
```

| | |
|---|---|
| agtgatgcag aggcaagctg atgatggccc tataaagagt atcctggcta cacacagtct | 33360 |
| ctgttggctc tttgctccct ggggtctgtg ttgtctcatt actgggcaga cttttacttg | 33420 |
| tttggctgta gcttcttgcc tctgattatc tggtgtgaat ttttactata tttctactgg | 33480 |
| gagatgattt ttgcctattt gtgtggaaag actgccagaa agatcttaaa aattaaaaaa | 33540 |
| aattacatgc cttttgcaag cataacttgt gagcctgatt cagaatgagt caggtgggtg | 33600 |
| gttccacaga agcactatgg accagctcca ttcagaatc ttctgagtcc cttgtctgta | 33660 |
| gatggagctc acgatgtttt tgtggccagt ggaaaatgga catcttgatg ttgtcaggaa | 33720 |
| acttctggtt tctgatgcag cctgctcacc acagttaggc tggacaccat gcggacagtg | 33780 |
| gaagggctt gggagttatc ttttgtcctg ctgggatgga atgcctattc tggaacaagg | 33840 |
| caagtggggtt ctagaggcac tcgcgtgttc cctgctcacc ttccctgct tgcttctgcg | 33900 |
| tttgccttag agattgggat ccttgaatgt atggctctct attacagaat taccaggttc | 33960 |
| cttcttcttc ttcttctttt tttttaatta aaaaaaagc atcaattttt gttgtggcac | 34020 |
| aaggagtaaa tgtcctgtct gcatagtata atgtatatac agcttcttct tgggtacggg | 34080 |
| tgagatggct caatggacaa aggcacttac gctgatgacc aagcctgacg ctctgtagtc | 34140 |
| aatcttcaga gcctatgtgg taggaaaaga gaactgaccc tcagaagttg tcctctgacc | 34200 |
| tccacactga tatgcacaca aacacatgca cacagataca ttttttttca tttaaaaaga | 34260 |
| aaatcacctt tctccttccc aaaagatact tagaaggttc agaaaagtcc ttatgtgtat | 34320 |
| tttaaataat aagatttcat atcaaaattt gcttactgat tttaacattt ctttgtgggg | 34380 |
| ttttttttct tttgagggg ggaggatagg gtctctggga ttgagctcag tgggtagcca | 34440 |
| aggataacca tcactgactt taatactgca aacactttc ttcaattcta ttaagggtag | 34500 |
| ttgggtttcc aaagagcaga agggcttgcc aatgggacag tcagtcctgg gaacaacata | 34560 |
| ggaccttggg ttcctctgat gagagtctag gatccacatg ggagagttcc tttggcttta | 34620 |
| tctttgccag ctggattgag gagtttgtat actcagcagg ggattgtcac ccatgtggga | 34680 |
| gctggaagcc tggtgtgctt gctgagtggc tcttgtctaa cctcacaccc atgtctccgg | 34740 |
| gaccaaagcc tccgttgtgg tctgagttga aagcagtatc cagcagccca ccatcacacc | 34800 |
| aagattgtgt agtcataccc aggcacaggc tttgtgtggg ctctgggtat attttctttc | 34860 |
| gcagaaatca gccaaggaga gacggtgtgt ttcagagata gacactgggt ctgacacagt | 34920 |
| ctgctataca tcaaggcaaa cttggtgaag ccctgtgtgc tgctgggtga gagaggaccc | 34980 |
| ttcccgtgtg gctctgagtg aaagtatctt ttccttaacc cttggtctcc tgtattcact | 35040 |
| gctctgcttt ctgaagctaa agtgacaaga gtcagcccat tttcactata tggtctgggc | 35100 |
| atcatcaagt ttcagaagga ctggggagag atggagaata gcctccccgt gcctggaact | 35160 |
| ctggatttct tgaataaaag acctttgagt taccagaatg ccctttccct gtgtcttagt | 35220 |
| taggatttta ttgctgcaaa gagacaacac aatgtaactt aaaaaaatta tttatttgtt | 35280 |
| ttatgtatat gagtgcacca tgactctctt cagagacact agaagagggc atcagatccc | 35340 |
| attacagatg gttgtgagcc accatgtggt tgctgggaat tgaactgagg acttctcaaa | 35400 |
| gagcagttgg tgctcttaac tactgagtca tctctccagc ccccagtgca actcttataa | 35460 |
| agaaacacac ttaattgggg cttgcttaca gtttcagagg tttagttcat tattgtcatg | 35520 |
| gtggaaagca tggcagcttc ctggcagaca cagtgctgga gagagaagaa gctgagagtt | 35580 |
| ctacatcttg atccacaggc agcagaaggg gattgtgtgc catactcttt gaggtttgag | 35640 |

```
caaaggaaac ctcaaagccc gcccccacag tgagaaactc cctccaacaa ggccacatgt   35700
tctctagcaa ggccacacct cctaatagcg cctatgggcc aggtattcaa accaccacac   35760
catacatatc ttacagctct ttccttgaga tctttcttta tactttggag gcaatggcag   35820
cacggatgac ctcacttgtt agatgtttgt gaatccctcc ctgctgactt gattttggat   35880 gtgttttttat tttatggtgc tggacattgt acatgagaca agcatcctgt aattgagccc   35940
agcctttgag ttagtgatct ataggctgag caaaaaacta taatgaagtc agtagagtct   36000
gtctgcacat tcttaagtgg ctgtcttaaa acaattaagg taaggggctg gagagatgct   36060
tcctcggcta agagcactgg ctgctcttcc agaggacctg ggttcagttc ccagcaccca   36120
tatggcagct cacaactgtc tatacctcca gttccagtct gacatcctca catagacata   36180
catgcaggca aaacaccaat gtacattaaa aaaacaccct aattttaaa aagttcagat   36240 gaaaagaaga aatactatga ttaaacttct agaaacattt ctatttgtaa acttgacctc   36300
ccaaggtcaa ggatcctgtg acttctcatt tttgccctg tattttgttg ttgttgttgt   36360
ttttgtttgt ttgttttgtg ttttgtttgt tgtttagttt agtttctcgt tgtttgtttt   36420
gtcctttcct ggttccttcc cctttctttg taagcactcc tgctctggct gggtcccagc   36480
tcacttccag cctcctctga tggagccagc attacatctg ctgttttgca ttttgtatac   36540
aggtttcggc cgagtccagc tcctccatga actccaacac cccgctggtg aggataacaa   36600
cgcgtctgtc ctcaacagcg gacacccccga tgctagcagg ggtctccgag tatgagttgc   36660
cagaggatcc aaagtgggaa ttccccagag ataagtaagt actctccctc tgggagggtc   36720
gttgtctgca cctcctggga ctgagcgcag gtcttggttg tgggagtctc cacctgtgtc   36780
ttggtaatca gggacctgtg tcttggtaat cagggacctt cgaactgtaa actgtaaact   36840
gtaaactgca gcaagatggt gcaattaaca gagctgctgg tgcacagggt aggctaccag   36900
cctgtgccct tgaggtggaa gaccaacctt agctctggga agtgaggatc ctggaaggct   36960
ggcagcttcc ttcttgtagg attagcgtct aaacagcttg agagtaacag aaggtggaaa   37020
aatgggctct ttctgcatca aagacacagg aatacgctcc cagcttgctt gaagacaact   37080
cgtctgccta tcttgacatt ttttcagtgt cttcctaaga ttgttagtga tatgtttaac   37140
acacacagcg tgtgtgtgtg tgtgtgtgtg tgtgtgtgtg tgtgtgtgtg tatacagaga   37200
ttcagaaaca caaagacaag cttttcccaag tctgggtatg gccagctcta gttgaaagtt   37260
gaaggaagct taggccccct tggagcttcg tgtcacacta ttccaggtat tttggttccc   37320
aacttagaga tctttacata tatcctaatc cagggccgag gaactgtctg tgtagtcatc   37380
ttatgtcagt ggaaagaatt tccagtttct ttatatactg cagtgaaaag agcattcatt   37440
cattccttca ttcattccgg gaatgtttag tggacatttt tggggtgagg tatgaaagaa   37500
aacacaaaga atggcttctt tacctataga atttgagaa aggaaggtat gtttctcttg   37560
acccttgcca gcctcctagc tgggtgtgat tatagaaata gctgggttcg tgtgcacatt   37620
cctatgtcta caaggctgga ctggggagtt gtgctcatat gctaaaaact tgcagctttc   37680
gggttgagcc tgtgctttgg gccacctgtg acaccacagt caacagtgtg agtctgtgtt   37740
gcccagcagc tcccacccgg gggtacccaa gtgtggaaaa tctgagcgct atgcatttcc   37800
aagcagtgtt tagcacaaat gtaggtggag cacattccca atgaatgaag gctatttaga   37860
aatggtttat taggttggag gcaggagtta cacaaagaga ggtttgttat ggttgtagta   37920
acaggggcaa taggacataa attagccatt ttccaacgaa aatgtttatt ttctgccaag   37980
atgttcaatt taatttagt tcttgactgg aaaggggggcg ccttcagcag agcaagtgct   38040
```

```
ggtatccatt ttcttttcct tttttgagct tttaaaagcg ttgcgtgctt actgcaaatg   38100
ctgtttactg aggacagctc aatacttgcc tgtactgggc ttatggtttt ttggttttg    38160 ttttttttaa aacaaaacaa aacaaaacaa aacaaaacac cccgaaaagc atactcaggc   38220
tggagaggta tctctctggt ctaaagcaga cactgccctg taaaggacca gagttcggtt   38280
cccagcaccc atgatgtgta gctcacaacc tctgtaacta cagatctggg gaatctgtct   38340
gggctcctta ggtgcctgtg ctcacatgcc catacctct ccccagaaac acacatacac    38400
ataatcaaga ataaattgaa aaaaataaa aataaaaaac acactcctaa gtattaattc    38460
caaagacttc cctgttcctt tggcttctgg aacatctaaa ataatgtcag gtcatttgtc   38520
tgttgtgtat aaaacttaca tgcttagaaa tgtaacttgt gctgttttct atttttttt    38580 ttccttgttt actttgggta gtgataagga atcctaaact tatgtcaaaa aggtatcgtg   38640
cctgatttct agaagttttt cttaatgaga cacgataaat tatttgaaac gtgctgaaga   38700
ttcctaccct gcaactgggc aatcgatgta accataaaat ctaccggtat tgaataatag   38760
tgatttgaga gttgccactt tacagggaca gaaaataaga acagactttc acttttttt    38820 tcacctctgc gacatttta attataaata tttaattggc tcaagaccaa aagctccta    38880 tggctggcat gcagggagcc tgaccaccgc gctagcaagg acaccttcca taagaaaaa    38940 gaaaataaat cgagaggaca aatgtgaaat ttaatagtcc ctccaacagt aattgacgtt   39000
ctggaaaaac atcactaaga aaatagcctg cgtgtgtatc ggaggctcat tggttccata   39060
tgcatgcctc tggaagattt ttatatttag ttctggaatt tccctccctg tgcccctcgg   39120
ccagactcgc ggtgtgctaa tcccgtattt acacatttag gctgacgctg gcaaacccc    39180 tgggggaagg ttgcttcggg caagtagtca tggctgaagc agtgggaatc gataaagaca   39240
aacccaagga ggcggtcacc gtggcagtga agatgttgaa aggtgagtgg gcggatgggc   39300
ggtcggggag gagagggtct tatcaggagc gagcgttcct tttgtgacat gtgaactctg   39360
cagggacgtg gggtcagaga gcacatactt gacctggcgg ttgaggggt tttcaggata    39420 aatgagcaaa tgagatggag gatttacctt gagctgtgtg tacttaaaaa gaaaagccag   39480
tttagcagca agttgtagct tgctgggctg aaccggtctc taactcctta gaaagggtc    39540 ccgattctct tcttttctgt gtgttcatgg gtttagaaag tttagggggt ttatttagct   39600
ggttaaattt tggacccaga cttttaacat acaaataagg agaggtaggt gttggagtgg   39660
caactggaga cagaatgtca aaatgtggat tcaaagagtc gcttagaagc caaaaggag    39720 caaacaattg gaactgatgc agaatcccag ggacatgtaa acaataatgc cacgctataa   39780
atgcccgctt tgttctttc ttttcttttc ttttcttttc ttttttttt ttttagggga    39840 gggaggggga ggggtctgg gaatttatcc acaacctttc taacacagct tgatgatgac    39900
gcccaaggag cttaaattgc tttcaactat taacttatcc ttgcatgggt attcttttat   39960
cgaagagata aagggaaagg tcacattata aatcctgttg ttggggaatc tcagaaagga   40020
gaaaggagcc atgttcaatg tttccctggc ttgtgggcag agaagtctgt cccgggcctg   40080
tgggatgtgg catgttctca ggagtccgac ctttctctc tttgatagga cacttaccac    40140
atccctccct gatgcagaca acaaagggcc aggacatggt tcatttttgtc agttttagtt   40200 attgacctga gactcccagt gaaatctggg atgttccttt ctttggagac tgataccagg   40260
aaggagatag caagtatcgg ggcaccaggg cagaggcagc ccttggtacc tactggaagc   40320
tgtgggttgg gaaggatcag gcatcatact gctttccaca gaacctctgg ttttgagatc   40380
```

```
cctggagcta gtgcaaaagg gaggtttagg ggttggccct tccctttaag caagatcacc    40440
caccatcctt ttcatcgtgg tcagaggaca tgccttttca acattctttg tgacagccag    40500
aggatggctg aggtgtaagg aagacaagtg tactgagcca tgtgtctgtc catagtcctc    40560
tcttccctct tctctgtatt ggtcaggata gattttttgga tacctgtgcc tctatttcat    40620
ttttaaccct tttgcttttc ttttagctca gattttttctt ttctaagtat ttctgtattg    40680
aattagctta gtgacagaac acttgcgtgg tgtgcacatg gtactgggtt tgcatcctag    40740
cattacaaga atccaaacga cagcagaact aactgagagg agagcacagt agcggccgca    40800
aattgctttg agaggctcta taaaacctta gaggctattt aaatttaaat ggccggcccg    40860
acggccaggc ggccgccagg cctacccact agtcaattcg ggaggatcga aacggcagat    40920
cgcaaaaaac agtacataca gaaggagaca tgaacatgaa catcaaaaaa attgtaaaac    40980
aagccacagt tctgactttt acgactgcac ttctggcagg aggagcgact caagccttcg    41040
cgaaagaaaa taaccaaaaa gcatacaaag aaacgtacgg cgtctctcat attacacgcc    41100
atgatatgct gcagatccct aaacagcagc aaaacgaaaa ataccaagtg cctcaattcg    41160
atcaatcaac gattaaaaat attgagtctg caaaaggact tgatgtgtgg gacagctggc    41220
cgctgcaaaa cgctgacgga acagtagctg aatacaacgg ctatcacgtt gtgtttgctc    41280
ttgcgggaag cccgaaagac gctgatgaca catcaatcta catgttttat caaaaggtcg    41340
gcgacaactc aatcgacagc tggaaaaacg cgggccgtgt cttaaagac agcgataagt    41400 tcgacgccaa cgatccgatc ctgaaagatc agacgcaaga atggtccggt tctgcaacct    41460
ttacatctga cggaaaaatc cgtttattct acactgacta ttccggtaaa cattacgca    41520 aacaaagcct gacaacagcg caggtaaatg tgtcaaaatc tgatgacaca ctcaaaatca    41580
acggagtgga agatcacaaa acgattttg acggagacgg aaaaacatat cagaacgttc    41640
agcagtttat cgatgaaggc aattatacat ccggcgacaa ccatacgctg agagaccctc    41700
actacgttga agacaaaggc cataaatacc ttgtattcga agccaacacg ggaacagaaa    41760
acggatacca aggcgaagaa tctttatttta acaaagcgta ctacggcggc ggcacgaact    41820
tcttccgtaa agaaagccag aagcttcagc agagcgctaa aaaacgcgat gctgagttag    41880
cgaacggcgc cctcggtatc atagagttaa ataatgatta cacattgaaa aaagtaatga    41940
agccgctgat cacttcaaac acggtaactg atgaaatcga gcgcgcgaat gttttcaaaa    42000
tgaacggcaa atggtacttg ttcactgatt cacgcggttc aaaaatgacg atcgatggta    42060
ttaactcaaa cgatatttac atgcttggtt atgtatcaaa ctctttaacc ggcccttaca    42120
agccgctgaa caaaacaggg cttgtgctgc aaatgggtct tgatccaaac gatgtgacat    42180
tcacttactc tcacttcgca gtgccgcaag ccaaaggcaa caatgtggtt atcacaagct    42240
acatgacaaa cagaggcttc ttcgaggata aaaaggcaac atttgcgcca agcttcttaa    42300
tgaacatcaa aggcaataaa acatccgttg tcaaaacag catcctggag caaggacagc    42360
tgacagtcaa ctaataacag caaaagaaa atgccgatac ttcattggca ttttctttta    42420
tttctcaaca agatggtgaa ttgactagtg ggtagatcca caggacgggt gtggtcgcca    42480
tgatcgcgta gtcgatagtg gctccaagta gcgaagcgag caggactggg cggcggccaa    42540
agcggtcgga cagtgctccg agaacgggtg cgcatagaaa ttgcatcaac gcatatagcg    42600
ctagcagcac gccatagtga ctggcgatgc tgtcggaatg gacgatatcc cgcaagaggc    42660
ccggcagtac cggcataacc aagcctatgc ctacagcatc cagggtgacg gtgccgagga    42720
tgacgatgag cgcattgtta gatttcatac acggtgcctg actgcgttag caatttaact    42780
```

```
gtgataaact accgcattaa agcttatcga tgataagctg tcaaacatga gaattgatcc   42840
ggaacccttaa atataacttc gtataatgta tgctatacga agttattagg tccctcgact   42900
ataggtcac cgtcgacagc gacacacttg catcggatgc agcccggtta acgtgccggc    42960
acggcctggg taaccaggta ttttgtccac ataaccgtgc gcaaaatgtt gtggataagc   43020
aggacacagc agcaatccac agcaggcata caaccgcaca ccgaggttac tccgttctac   43080
aggttacgac gacatgtcaa tacttgccct tgacaggcat tgatggaatc gtagtctcac   43140
gctgatagtc tgatcgacaa tacaagtggg accgtggtcc cagaccgata atcagaccga   43200
caacacgagt gggatcgtgg tcccagacta ataatcagac cgacgatacg agtgggaccg   43260
tggtcccaga ctaataatca gaccgacgat acgagtggga ccgtggttcc agactaataa   43320
tcagaccgac gatacgagtg ggaccgtggt cccagactaa taatcagacc gacgatacga   43380
gtgggaccat ggtcccagac taataatcag accgacgata cgagtgggac cgtggtccca   43440
gtctgattat cagaccgacg atacgagtgg gaccgtggtc ccagactaat aatcagaccg   43500
acgatacgag tgggaccgtg gtcccagact aataatcaga ccgacgatac gagtgggacc   43560
gtggtcccag tctgattatc agaccgacga tacaagtgga acagtgggcc cagagagaat   43620
attcaggcca gttatgcttt ctggcctgta acaaaggaca ttaagtaaag acagataaac   43680
gtagactaaa acgtggtcgc atcagggtgc tggcttttca agttccttaa gaatggcctc   43740
aatttctct atacactcag ttggaacacg agacctgtcc aggttaagca ccattttatc   43800
gcccttatac aatactgtcg ctccaggagc aaactgatgt cgtgagctta aactagttct   43860
tgatgcagat gacgttttaa gcacagaagt taaaagagtg ataacttctt cagcttcaaa   43920
tatcacccca gctttttcct gctcatgaag gttagatgcc tgctgcttaa gtaattcctc   43980
tttatctgta aaggcttttt gaagtgcatc acctgaccgg gcagatagtt caccggggtg   44040
agaaaaaga gcaacaactg atttaggcaa tttggcggtg ttgatacagc gggtaataat   44100
cttacgtgaa atattttccg catcagccag cgcagaaata tttccagcaa attcattctg   44160
caatcggctt gcataacgct gaccacgttc ataagcactt gttgggcgat aatcgttacc   44220
caatctggat aatgcagcca tctgctcatc atccagctcg ccaaccagaa cacgataatc   44280
actttcggta agtgcagcag ctttacgacg gcgactccca tcggcaattt ctatgacacc   44340
agatactctt cgaccgaacg ccggtgtctg ttgaccagtc agtagaaaag aagggatgag   44400
atcatccagt gcgtcctcag taagcagctc ctggtcacgt tcattacctg accatacccg   44460
agaggtcttc tcaacactat caccccggag cacttcaaga gtaaacttca catcccgacc   44520
acatacaggc aaagtaatgg cattaccgcg agccattact cctacgcgcg caattaacga   44580
atccaccatc ggggcagctg gtgtcgataa cgaagtatct tcaacggtt gagtattgag   44640
cgtatgtttt ggaataacag gcgcacgctt cattatctaa tctcccagcg tggtttaatc   44700
agacgatcga aaatttcatt gcagacaggt tcccaaatag aaagagcatt tctccaggca   44760
ccagttgaag agcgttgatc aatggcctgt tcaaaaacag ttctcatccg gatctgacct   44820
ttaccaactt catccgtttc acgtacaaca ttttttagaa ccatgcttcc ccaggcatcc   44880
cgaatttgct cctccatcca cggggactga gagccattac tattgctgta tttggtaagc   44940
aaaatacgta catcaggctc gaacccttta agatcaacgt tcttgagcag atcacgaagc   45000
atatcgaaaa actgcagtgc ggaggtgtag tcaaacaact cagcaggcgt gggaacaatc   45060
agcacatcag cagcacatac gacattaatc gtgccgatac ccaggttagg cgcgctgtca   45120
```

```
ataactatga catcatagtc atgagcaaca gtttcaatgg ccagtcggag catcaggtgt    45180
ggatcggtgg gcagtttacc ttcatcaaat ttgcccatta actcagtttc aatacggtgc    45240
agagccagac aggaaggaat aatgtcaagc cccggccagc aagtgggctt tattgcataa    45300
gtgacatcgt cctttccccc aagatagaaa ggcaggagag tgtcttctgc atgaatatga    45360
agatctggta cccatccgtg atacattgag gctgttccct gggggtcgtt accttccacg    45420
agcaaaacac gtagccccctt cagagccaga tcctgagcaa gatgaacaga aactgaggtt    45480
ttgtaaacgc cacctttatg ggcagcaacc ccgatcaccg gtggaaatac gtcttcagca    45540
cgtcgcaatc gcgtaccaaa cacatcacgc atatgattaa tttgttcaat tgtataacca    45600
acacgttgct caacccgtcc tcgaatttcc atatccgggt gcggtagtcg ccctgctttc    45660
tcggcatctc tgatagcctg agaagaaacc ccaactaaat ccgctgcttc acctattctc    45720
cagcgccggg ttattttcct cgcttccggg ctgtcatcat taaactgtgc aatggcgata    45780
gccttcgtca tttcatgacc agcgtttatg cactggttaa gtgtttccat gagtttcatt    45840
ctgaacatcc tttaatcatt gctttgcgtt ttttattaa atcttgcaat ttactgcaaa    45900
gcaacaacaa aatcgcaaag tcatcaaaaa accgcaaagt tgtttaaaat aagagcaaca    45960
ctacaaaagg agataagaag agcacatacc tcagtcactt attatcacta gcgctcgccg    46020
cagccgtgta accgagcata gcgagcgaac tggcgaggaa gcaaagaaga actgttctgt    46080
cagatagctc ttacgctcag cgcaagaaga aatatccacc gtgggaaaaa ctccaggtag    46140
aggtacacac gcggatagcc aattcagagt aataaactgt gataatcaac cctcatcaat    46200
gatgacgaac taacccccga tatcaggtca catgacgaag ggaaagagaa ggaaatcaac    46260
tgtgacaaac tgccctcaaa tttggcttcc ttaaaaatta cagttcaaaa agtatgagaa    46320
aatccatgca ggctgaagga aacagcaaaa ctgtgacaaa ttaccctcag taggtcagaa    46380
caaatgtgac gaaccacccct caaatctgtg acagataacc ctcagactat cctgtcgtca    46440
tggaagtgat atcgcggaag gaaaatacga tatgagtcgt ctggcggcct ttcttttttct    46500 caatgtatga gaggcgcatt ggagttctgc tgttgatctc attaacacag acctgcagga    46560
agcggcggcg gaagtcaggc atacgctggt aactttgagg cagctggtaa cgctctatga    46620
tccagtcgat tttcagagag acgatgcctg agccatccgg cttacgatac tgacacaggg    46680
attcgtataa acgcatggca tacggattgg tgatttctttt tgtttcacta agccgaaact    46740
gcgtaaaccg gttctgtaac ccgataaaga agggaatgag atatggggttg atatgtacac    46800 tgtaaagccc tctggatgga ctgtgcgcac gtttgataaa ccaaggaaaa gattcatagc    46860 cttttttcatc gccggcatcc tcttcagggc gataaaaaac cacttccttc cccgcgaaac    46920
tcttcaatgc ctgccgtata tccttactgg cttccgcaga ggtcaatccg aatatttcag    46980
catatttagc aacatggatc tcgcagatac cgtcatgttc ctgtagggtg ccatcagatt    47040
ttctgatctg gtcaacgaac agatacagca tacgttttttg atcccgggag agactatatg    47100
ccgcctcagt gaggtcgttt gactggacga ttcgcgggct attttttacgt tcttgtgat    47160 tgataaccgc tgtttccgcc atgacagatc catgtgaagt gtgacaagtt tttagattgt    47220
cacactaaat aaaaaagagt caataagcag ggataacttt gtgaaaaaac agcttcttct    47280
gagggcaatt tgtcacaggg ttaagggcaa tttgtcacag acaggactgt catttgaggg    47340
tgatttgtca cactgaaagg gcaatttgtc acaacacctt ctctagaacc agcatggata    47400
aaggcctaca aggcgctcta aaaaagaaga tctaaaaact ataaaaaaaa taattataaa    47460
aatatccccg tggataagtg gataaccccca agggaagttt tttcaggcat cgtgtgtaag    47520
```

```
cagaatatat aagtgctgtt ccctggtgct tcctcgctca ctcgagggct tcgccctgtc   47580
gctcaactgc ggcgagcact actggctgta aaaggacaga ccacatcatg gttctgtgtt   47640
cattaggttg ttctgtccat tgctgacata atccgctcca cttcaacgta acaccgcacg   47700
aagatttcta ttgttcctga aggcatattc aaatcgtttt cgttaccgct tgcaggcatc   47760
atgacagaac actacttcct ataaacgcta cacaggctcc tgagattaat aatgcggatc   47820
tctacgataa tgggagattt tcccgactgt ttcgttcgct tctcagtgga taacagccag   47880
cttctctgtt taacagacaa aaacagcata tccactcagt tccacatttc catataaagg   47940
ccaaggcatt tattctcagg ataattgttt cagcatcgca accgcatcag actccggcat   48000
cgcaaactgc acccggtgcc gggcagccac atccagcgca aaaaccttcg tgtagacttc   48060
cgttgaactg atggacttat gtcccatcag gctttgcaga actttcagcg gtataccggc   48120
atacagcatg tgcatcgcat aggaatggcg gaacgtatgt ggtgtgaccg gaacagagaa   48180
cgtcacaccg tcagcagcag cggcggcaac cgcctcccca atccaggtcc tgaccgttct   48240
gtccgtcact tcccagatcc gcgctttctc tgtccttcct gtgcgacggt tacgccgctc   48300
catgagctta tcgcgaataa atacctgtga cggaagatca cttcgcagaa taaataaatc   48360
ctggtgtccc tgttgatacc gggaagccct gggccaactt ttggcgaaaa tgagacgttg   48420
atcggcacgt aagaggttcc aactttcacc ataatgaaat aagatcacta ccgggcgtat   48480
tttttgagtt atcgagattt tcaggagcta aggaagctaa aatggagaaa aaaatcactg   48540
gatataccac cgttgatata tcccaatggc atcgtaaaga acattttgag gcatttcagt   48600
cagttgctca atgtacctat aaccagaccg ttcagctgga tattacggcc ttttttaaga   48660
ccgtaaagaa aaataagcac aagttttatc cggcctttat tcacattctt gcccgcctga   48720
tgaatgctca tccggagttc cgtatggcaa tgaaagacgg tgagctggtg atatgggata   48780
gtgttcaccc ttgttacacc gttttccatg agcaaactga acgttttca tcgctctgga   48840
gtgaatacca cgacgatttc cggcagtttc tacacatata ttcgcaagat gtggcgtgtt   48900
acggtgaaaa cctggcctat ttccctaaag ggtttattga gaatatgttt ttcgtctcag   48960
ccaatccctg ggtgagtttc accagttttg atttaaacgt ggccaatatg acaacttct   49020
tcgccccgt tttcaccatg ggcaaatatt atacgcaagg cgacaaggtg ctgatgccgc   49080
tggcgattca ggttcatcat gccgtttgtg atggcttcca tgtcggcaga atgcttaatg   49140
aattacaaca gtactgcgat gagtggcagg gcggggcgta atttttttaa ggcagttatt   49200
ggtgccctta aacgcctggt tgctacgcct gaataagtga taataagcgg atgaatggca   49260
gaaattcgat gataagctgt caaacatgag aattggtcga cggcgcgcca agcttgcat   49320
gcctgcagcc gcgtaacctg gcaaaatcgg ttacggttga gtaataaatg gatgccctgc   49380
gtaagcgggg cacatttcat tacctctttc tccgcacccg acatagataa taacttcgta   49440
tagtatacat tatacgaagt tatctagtag acttaattaa ggatcgatcc ggcgcgccaa   49500
tagtcatgcc ccgcgcccac cggaaggagc tgactgggtt gaaggctctc aagggcatcg   49560
gtcgagcttg acattgtagg actatattgc tctaataaat ttgcggccgc taatacgact   49620
cactataggg a                                                        49631
```

<210> SEQ ID NO 18
<211> LENGTH: 20
<212> TYPE: DNA
<213> ORGANISM: Artificial Sequence
<220> FEATURE:

<223> OTHER INFORMATION: Synthetic

<400> SEQUENCE: 18
ggaaagccac cctgtatgct                                                    20

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
cttggccaac agtggatgg                                                     19

<210> SEQ ID NO 20
<211> LENGTH: 42
<212> TYPE: RNA
<213> ORGANISM: Artificial Sequence
<220> FEATURE:
<223> OTHER INFORMATION: Synthetic

<400> SEQUENCE: 20
cuaaaaugau ucucaucugc guuuuagagc uaugcuguuu ug                           42

<210> SEQ ID NO 21
<211> LENGTH: 42
<212> TYPE: RNA
<213> ORGANISM: Artificial Sequence
<220> FEATURE:
<223> OTHER INFORMATION: Synthetic

<400> SEQUENCE: 21
gcucucaacu ucacccuuuc guuuuagagc uaugcuguuu ug                           42

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
ctaaaatgat tctcatctgc agg                                                23

<210> SEQ ID NO 23
<211> LENGTH: 23
<212> TYPE: DNA
<213> ORGANISM: Artificial Sequence
<220> FEATURE:
<223> OTHER INFORMATION: Synthetic

<400> SEQUENCE: 23
gctctcaact tcacccttc tgg                                                 23

<210> SEQ ID NO 24
<211> LENGTH: 23
<212> TYPE: DNA
<213> ORGANISM: Artificial Sequence
<220> FEATURE:
<223> OTHER INFORMATION: Synthetic- a target locus that is linked to a
      guide RNA (gRNA)
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20, 21
<223> OTHER INFORMATION: n = A,T,C or G

```
<400> SEQUENCE: 24
nnnnnnnnnn nnnnnnnnnn ngg                                              23

<210> SEQ ID NO 25
<211> LENGTH: 25
<212> TYPE: DNA
<213> ORGANISM: Artificial Sequence
<220> FEATURE:
<223> OTHER INFORMATION: Synthetic- a target locus that is linked to a
      guide RNA (gRNA)
<220> FEATURE:
<221> NAME/KEY: misc_feature
<222> LOCATION: 3, 4, 5, 6, 7, 8, 9, 10, 11, 12, 13, 14, 15, 16, 17, 18,
      19, 20, 21, 22, 23
<223> OTHER INFORMATION: n = A,T,C or G

<400> SEQUENCE: 25
ggnnnnnnnn nnnnnnnnnn nnngg                                            25
```

NUCLEASE-MEDIATED DNA ASSEMBLY

CROSS-REFERENCE TO RELATED APPLICATIONS

This application is a continuation of U.S. patent application Ser. No. 15/638,832, filed Jun. 30, 2017, which is a continuation of U.S. patent application Ser. No. 14/747,461, filed Jun. 23, 2015, which claims the benefit of U.S. Provisional Application No. 62/015,809, filed Jun. 23, 2014, U.S. Provisional Application No. 62/016,400, filed Jun. 24, 2014, and U.S. Provisional Application No. 62/036,983, filed Aug. 13, 2014, each of which is herein incorporated by reference in its entirety for all purposes.

REFERENCE TO A SEQUENCE LISTING SUBMITTED AS A TEXT FILE VIA EFS WEB

The official copy of the sequence listing is submitted electronically via EFS-Web as an ASCII formatted sequence listing with a file named 526605SEQLIST.TXT, created on Mar. 6, 2019, and having a size of 65.8 kb, and is filed concurrently with the specification. The sequence listing contained in this ASCII formatted document is part of the specification and is herein incorporated by reference in its entirety.

BACKGROUND

Historically, overlap extension could be used as a means of synthesizing larger double stranded DNA molecules, particularly genes, from overlapping synthetic oligonucleotides. However, these methods could not effectively combine large DNA molecules in a rapid manner. Further, site-specific combination of large nucleic acids using overlapping sequences is often limited by the availability of overlapping sequences at the desired position in the nucleic acids to be combined. Engineered nuclease enzymes designed to target specific DNA sequences have attracted attention as powerful tools for genetic manipulation allowing for targeted gene deletion, replacement, and repair, as well as the insertion of exogenous sequences. However, existing technologies suffer from limited precision, which can lead to unpredictable off-target effects and time consuming multistep reactions.

SUMMARY

Methods are provided herein for assembling nucleic acids having overlapping sequences. Such methods comprise a method for assembling at least two nucleic acids, comprising: (a) contacting a first nucleic acid with a first nuclease agent, wherein the first nuclease agent cleaves the first nucleic acid at a first target site to produce a first digested nucleic acid with overlapping end sequences between the first digested nucleic acid and a second nucleic acid; (b) contacting the first digested nucleic acid and the second nucleic acid with an exonuclease to expose complementary sequences between the first digested nucleic acid and the second nucleic acid; and (c) assembling the two nucleic acid fragments generated from step (b). In some such methods step (c) further comprises: (i) annealing the exposed complementary sequences; (ii) extending 3' ends of the annealed complementary sequences; and (iii) ligating the first and the second nucleic acid.

In some of the methods step (a) further comprises contacting the second nucleic acid with a second nuclease agent, wherein the second nucleic acid does not comprise the overlapping end sequence, and the second nuclease agent cleaves the second nucleic acid at a second target site to produce a second digested nucleic acid with the overlapping end sequences between the first digested nucleic acid and the second digested nucleic acid, and wherein the second nucleic acid of step (b) is the second digested nucleic acid. In some of the methods, the overlapping end sequence ranges from 20 bp to 200 bp long.

In some of the methods, at least one of the first or second nuclease agent comprises a Cas protein and a guide RNA (gRNA) (gRNA-Cas complex) that targets the first or the second target site. For example, the Cas protein can be a Cas9 protein. The Cas9 protein may comprise a RuvC domain and a HNH domain, at least one of which lacks endonuclease activity. In some embodiments, the gRNA comprises a nucleic acid sequence encoding a Clustered Regularly Interspaced Short Palindromic Repeats (CRISPR) RNA (crRNA) and a trans-activating CRISPR RNA (tracrRNA). The first target site and/or second target site can be flanked by a Protospacer Adjacent Motif (PAM) sequence. In some of the methods the nuclease agent comprises a zinc finger nuclease or a Transcription Activator-Like Effector Nuclease (TALEN).

In some of the methods the first, the second, or both nucleic acids are from a bacterial artificial chromosome. The bacterial artificial chromosome can comprise a human DNA, a rodent DNA, a synthetic DNA, or a combination thereof. The bacterial artificial chromosome can comprise a human sequence.

The methods disclosed herein include a method for assembling at least two nucleic acids, comprising: (a) contacting a first nucleic acid with a first nuclease agent and a second nuclease agent to produce a first digested nucleic acid, wherein the first nuclease agent generates a nick on a first strand of the first nucleic acid at a first target site, and the second nuclease agent generates a nick on a second strand of the first nucleic acid at a second target site, to produce a first digested nucleic acid comprising 5' or 3' overhanging sequence at one of its ends; (b) annealing the first digested nucleic acid and a second nucleic acid comprising a complementary sequence to the 5' or 3' overhanging sequence; and (c) ligating the first digested nucleic acid and the second nucleic acid. In some of the methods, step (b) further comprises extending the 3' end of the first strand using the second strand as a template and extending the 3' end of the second strand based using the first strand as a template. In some of the methods, the first target site is separated by at least 4 bp from the second target site.

In some of the methods, at least one of the first or second nuclease agent comprises a Cas9 protein and a guide RNA (gRNA) (gRNA-Cas complex) that targets the first or the second target site. The gRNA can comprise a nucleic acid sequence encoding a Clustered Regularly Interspaced Short Palindromic Repeats (CRISPR) RNA (crRNA) and a trans-activating CRISPR RNA (tracrRNA). In some of the methods, at least one of the first target site and second target site is flanked by a Protospacer Adjacent Motif (PAM) sequence. The Cas9 protein can comprise a RuvC domain and a HNH domain, one of which lacks endonuclease activity.

In some of the methods, the second nucleic acid does not comprise the complementary sequence to the 5' or 3' overhanging sequence of the first digested nucleic acid, and step (a) further comprises contacting the first digested nucleic acid and the second digested nucleic acid with a joiner oligo, wherein the joiner oligo comprises: (i) a first complementary sequence to the 5' or 3' overhanging sequence of the first digested nucleic acid; and (ii) a second complementary sequence to the 5' or 3' overhanging sequence of the second digested nucleic acid. In some methods, the first, the second, or both nucleic acids are derived from a bacterial artificial chromosome. The bacterial artificial chromosome can comprise a human DNA, a rodent DNA, a synthetic DNA, or a combination thereof. The bacterial artificial chromosome can comprise a human polynucleotide sequence. In some methods, the second nucleic acid comprises a bacterial artificial chromosome.

Methods provided also include a method for assembling two or more nucleic acid fragments, comprising: (a) contacting a first nucleic acid with at least one nuclease agent to generate a first digested nucleic acid; (b) contacting the first digested nucleic acid with a second nucleic acid, a joiner oligo, and an exonuclease, wherein the joiner oligo comprises: (i) a first complementary sequence that is complementary to the first digested nucleic acid; (ii) a spacer; and (iii) a second complementary sequence that is complementary to the second nucleic acid; wherein the exonuclease exposes the first and second complementary sequences; and (c) assembling the joiner oligo with the first digested nucleic acid and the second nucleic acid. In some such methods the assembling in step (c) comprises: (i) annealing the first complementary sequence of the joiner oligo to the first digested nucleic acid and the second complementary sequence of the joiner oligo to the second nucleic acid; and (ii) ligating the joiner oligo to the first digested nucleic acid and the second nucleic acid.

In some methods the first complementary sequence and the second complementary sequence of the joiner oligo comprise between 15 and 120 complementary bases. In some methods, the spacer of the joiner oligo comprises non-complementary nucleic acids. In some embodiments, the first digested nucleic acid is seamlessly assembled to the second nucleic acid.

In some methods, the nuclease agent is designed to cleave an at least 20 bp fragment from the end of the first nucleic acid at which the seamless assembly will occur, wherein, the spacer of the joiner oligo comprises a sequence identical to said at least 20 bp fragment, wherein no nucleic acid bases are present between the first complementary sequence and the at least 20 bp fragment, and no nucleic acid bases are present between the second complementary sequence and the at least 20 bp fragment, such that assembly of said first nucleic acid with said joiner oligo and said second nucleic acid reconstitutes the at least 20 bp fragment and seamlessly assembles the first and second nucleic acid. In some methods, the same method is performed with an at least 20 bp fragment from the second nucleic acid as the spacer sequence. In some methods, the spacer comprises from about 20 bp to about 120 bp. In some methods, the second nucleic acid is contacted with a second nuclease agent and an exonuclease, wherein the second nuclease agent cleaves the second nucleic acid to produce a second digested nucleic acid comprising a nucleotide sequence that is complementary to the second complementary sequence of the joiner oligo, wherein the first digested nucleic acid is assembled to the second digested nucleic acid. In some methods, the second nucleic acid is contacted with a restriction enzyme or meganuclease and an exonuclease, wherein the restriction enzyme or meganuclease cleaves the second nucleic acid to produce a second digested nucleic acid comprising a nucleotide sequence that is complementary to the second complementary sequence in the joiner oligo, wherein the first digested nucleic acid is assembled to the second digested nucleic acid. In some methods, the 3' end of the first and/or the second digested nucleic acids is extended in step (b). The joiner oligo can be assembled to said first nucleic acid and said second nucleic acid in the same reaction or sequentially. In some methods, the first, the second, or both nucleic acids are derived from a bacterial artificial chromosome, at least 10 kb, and/or comprise a human DNA, rodent DNA, a synthetic DNA, or a combination thereof.

In some of the methods, the at least one nuclease agent or second nuclease agent comprises a Cas protein and a guide RNA (gRNA) (gRNA-Cas complex) that targets the first or the second target site. For example, the Cas protein can be a Cas9 protein. The Cas9 protein may comprise a RuvC domain and a HNH domain, at least one of which lacks endonuclease activity. In some embodiments, the gRNA comprises a nucleic acid sequence encoding a Clustered Regularly Interspaced Short Palindromic Repeats (CRISPR) RNA (crRNA) and a trans-activating CRISPR RNA (tracrRNA). The first target site and/or second target site can be flanked by a Protospacer Adjacent Motif (PAM) sequence. In some of the methods the at least one nuclease agent and/or the second nuclease agent comprises a zinc finger nuclease or a Transcription Activator-Like Effector Nuclease (TALEN).

In some embodiments, the joiner oligo comprises a gBlock. In some such methods, the gBlock does not comprise a selection cassette.

Methods are further provided for assembling two or more nucleic acids, comprising: (a) contacting a first nucleic acid with at least one nuclease agent to generate a first digested nucleic acid; (b) contacting a second nucleic acid with a second nuclease agent to generate a second digested nucleic acid; (c) contacting the first digested nucleic acid and the second digested nucleic acid with a joiner oligo and an exonuclease, wherein the joiner oligo comprises: (i) a first complementary sequence that is complementary to the first digested nucleic acid; (ii) a spacer; and (iii) a second complementary sequence that is complementary to the second digested nucleic acid; wherein the exonuclease exposes the first and second complementary sequences; and (d) assembling the joiner oligo with the first digested nucleic acid and the second nucleic acid.

Methods are provided herein for assembling nucleic acids having overlapping sequences. Such methods comprise a method for assembling at least two nucleic acid fragments, comprising (a) contacting a first and a second nucleic acid comprising overlapping sequences with at least one gRNA-Cas complex and an exonuclease, thereby generating two digested nucleic acid fragments comprising complementary sequences at one of their ends; (b) assembling the two nucleic acid fragments generated from step (a). In some methods, the at least one gRNA-Cas complex cleaves the first nucleic acid at a first target site to produce a first digested nucleic acid comprising complementary end sequences between the first digested nucleic acid and the second nucleic acid. In certain methods, step (b) further comprises: (i) annealing the exposed complementary sequences; (ii) extending 3' ends of the annealed complementary sequences; and (iii) ligating the first and the second nucleic acid. In some methods, step (a) further comprises contacting the second nucleic acid with a second gRNA-Cas complex, wherein the second nucleic acid does not comprise the overlapping end sequence, and the second gRNA-Cas complex cleaves the second nucleic acid to produce a second digested nucleic acid comprising the overlapping end sequences between the first digested nucleic acid and the second digested nucleic acid. For example, the gRNA-Cas complex comprises a Cas9 protein. The Cas9 protein can comprise a RuvC domain and a HNH domain, at least one of which lacks endonuclease activity. In some methods, the overlapping sequence ranges from 20 bp to 200 bp long. The method of any one of claims 1-7, wherein the first, the second, or both nucleic acids are from a bacterial artificial chromosome. In some methods, the bacterial artificial chromosome comprises a human DNA, a rodent DNA, a synthetic DNA, or a combination thereof. The bacterial artificial chromosome can comprise a human sequence.

Methods provided also include a method for assembling two or more nucleic acid fragments, comprising: (a) exposing a first and a second nucleic acid to at least one gRNA-Cas complex to generate a first and a second digested nucleic acids comprising a 5' or 3' overhanging sequence at one of their ends; (b) assembling the two nucleic acid fragments generated from step (a). In some methods, assembling step (b) comprises: (i) annealing the 5' and 3' overhanging sequences; and (ii) ligating the first digested nucleic acid and the second digested nucleic acid. In some methods, the 5' and/or 3' overhanging sequences comprise at least 4 complementary bases. In some methods, step (b) further comprises extending the 3' end of the first and the second digested nucleic acids. In some methods, the second nucleic acid does not comprise a complementary sequence to the 5' or 3' overhanging sequence of the first digested nucleic acid, and step (a) further comprises contacting the first digested nucleic acid and the second digested nucleic acid with a joiner oligo, wherein the joiner oligo comprises: (i) a first complementary sequence to the 5' or 3' overhanging sequence of the first digested nucleic acid; and (ii) a second complementary sequence to the 5' or 3' overhanging sequence of the second digested nucleic acid. In some methods, the gRNA-Cas protein complex comprises a Cas9 protein comprising a RuvC domain and a HNH domain, one of which lacks endonuclease activity. In some methods the gRNA-Cas complex is provided separately as a crRNA, tracrRNA, and Cas protein. In some methods, the first and the second nucleic acids comprise a Protospacer Adjacent Motif (PAM) sequence. In some methods, the first, the second, or both nucleic acids are derived from a bacterial artificial chromosome. In some methods, the bacterial artificial chromosome comprises a human DNA, a rodent DNA, a synthetic DNA, or a combination thereof. For example, the bacterial artificial chromosome can comprise a human polynucleotide sequence.

Methods are further provided for assembling two or more nucleic acids, comprising: (a) contacting a first nucleic acid with at least one gRNA-Cas complex to generate a first digested nucleic acid; and (b) contacting the first digested nucleic acid with a second nucleic acid, a joiner oligo, and an exonuclease, wherein the joiner oligo comprises: (i) a first complementary sequence that is complementary to the first digested nucleic acid; (ii) a spacer; and (iii) a second complementary sequence that is complementary to the second nucleic acid; wherein the exonuclease exposes the first and second complementary sequences; and (c) assembling the joiner oligo with the first digested nucleic acid and the second nucleic acid. In some methods assembling step (c) comprises (i) annealing the first complementary sequence of the joiner oligo to the first digested nucleic acid and the second complementary sequence of the joiner oligo to the second nucleic acid; and (ii) ligating the joiner oligo to the first digested nucleic acid and the second nucleic acid. In some methods the first complementary sequence and the second complementary sequence of the joiner oligo comprise between 15 and 120 complementary bases. In some methods, the spacer of the joiner oligo comprises non-complementary nucleic acids.

Using the joiner oligo, the first digested nucleic acid can be seamlessly assembled to the second nucleic acid. In some methods, the gRNA-Cas complex is designed to cleave an at least 20 bp fragment from the end of the first nucleic acid at which the seamless assembly will occur, wherein the spacer of the joiner oligo comprises a sequence identical to said at least 20 bp fragment, wherein no nucleic acid bases are present between the first complementary sequence and the at least 20 bp fragment, and no nucleic acid bases are present between the second complementary sequence and the at least 20 bp fragment, such that assembly of said first nucleic acid with said joiner oligo and said second nucleic acid reconstitutes the at least 20 bp fragment and seamlessly assembles the first and second nucleic acid. In some methods, the same method is performed with an at least 20 bp fragment from the second nucleic acid as the spacer sequence. In some methods, the spacer comprises from about 20 bp to about 120 bp. In some methods, the second nucleic acid is contacted with a second gRNA-Cas complex and an exonuclease, wherein the second gRNA-Cas complex cleaves the second nucleic acid to produce a second digested nucleic acid comprising a nucleotide sequence that is complementary to the second complementary sequence of the joiner oligo, wherein the first digested nucleic acid is assembled to the second digested nucleic acid. In some methods, the second nucleic acid is contacted with a restriction enzyme or meganuclease and an exonuclease, wherein the restriction enzyme or meganuclease cleaves the second nucleic acid to produce a second digested nucleic acid comprising a nucleotide sequence that is complementary to the second complementary sequence in the joiner oligo, wherein the first digested nucleic acid is assembled to the second digested nucleic acid. In some methods, the 3' end of the first and/or the second digested nucleic acids is extended in step (b). The joiner oligo can be assembled to said first nucleic acid and said second nucleic acid in the same reaction or sequentially. In some methods, the gRNA-Cas complex comprises a Cas9 protein. In some methods, the first, the second, or both nucleic acids are derived from a bacterial artificial chromosome, at least 10 kb, and/or comprise a human DNA, rodent DNA, a synthetic DNA, or a combination thereof.

BRIEF DESCRIPTION OF THE DRAWINGS

FIG. 4 shows the cloning efficiencies of Cas9/isothermal assembly method and the time required for BAC cloning steps.

FIG. 6 shows the strategy for using linkers (joiner oligos) for seamlessly assembling nucleic acids after Cas9 cleavage.

A gRNA/Cas9 complex is designed to cleave a target site located 5' upstream of an area of interest (arrow) to generate a first Cas9-digested DNA fragment (5' DNA). The deleted portion of the 5' DNA (slashed box) is then used as a spacer between the 5' and 3' overlapping sequences in a joiner oligo. Three components are assembled in the isothermal assembly reaction: (a) a first Cas9-digested DNA fragment (5' DNA); (b) a joiner oligo; and (c) a second DNA fragment (3' DNA). The joiner oligo comprises from 5' to 3': (1) an overlapping sequence with 5' DNA, (2) a spacer containing the deleted portion of the first digested fragment, and (3) an overlapping sequence with 3' DNA. The deleted portion of the 5'DNA is reconstituted during the assembly step.

Figure 7:
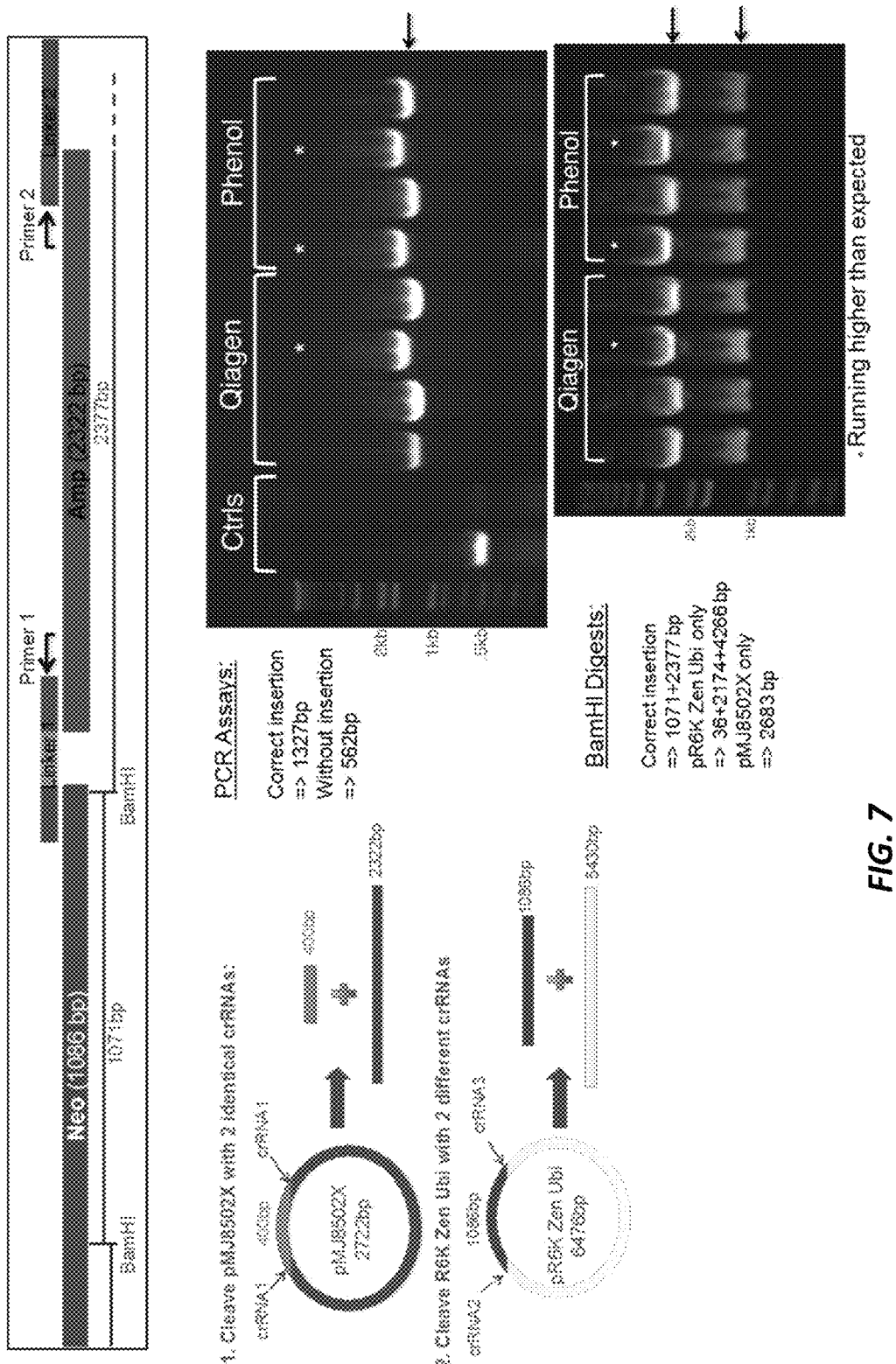

FIG. 7 shows the construction of a DNA vector using CRISPR/Cas9 system and isothermal assembly.

Figure 8:
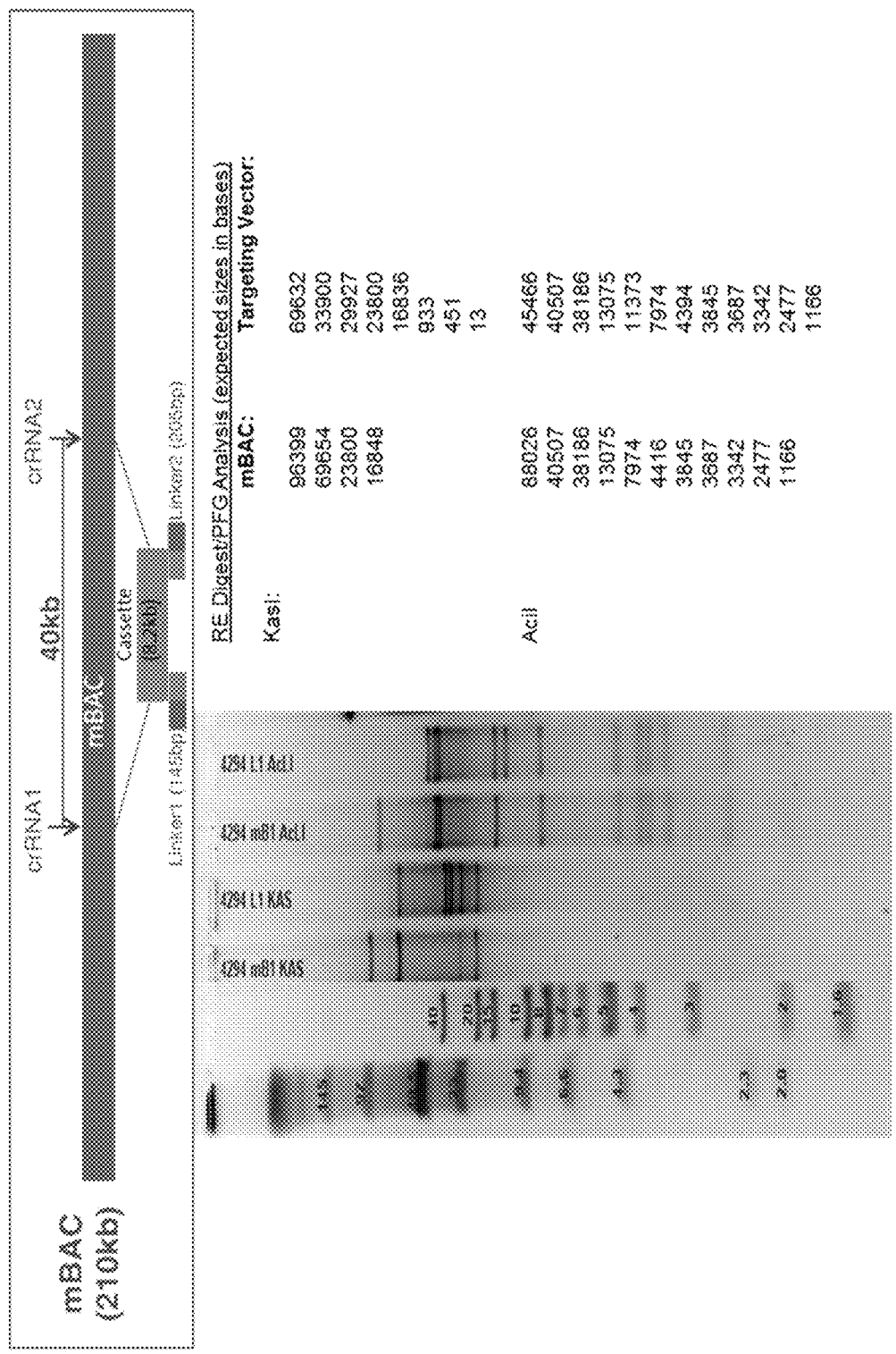

FIG. 8 shows the construction of a large targeting vector using CRISPR/Cas9 system and isothermal assembly.

Figure 9:
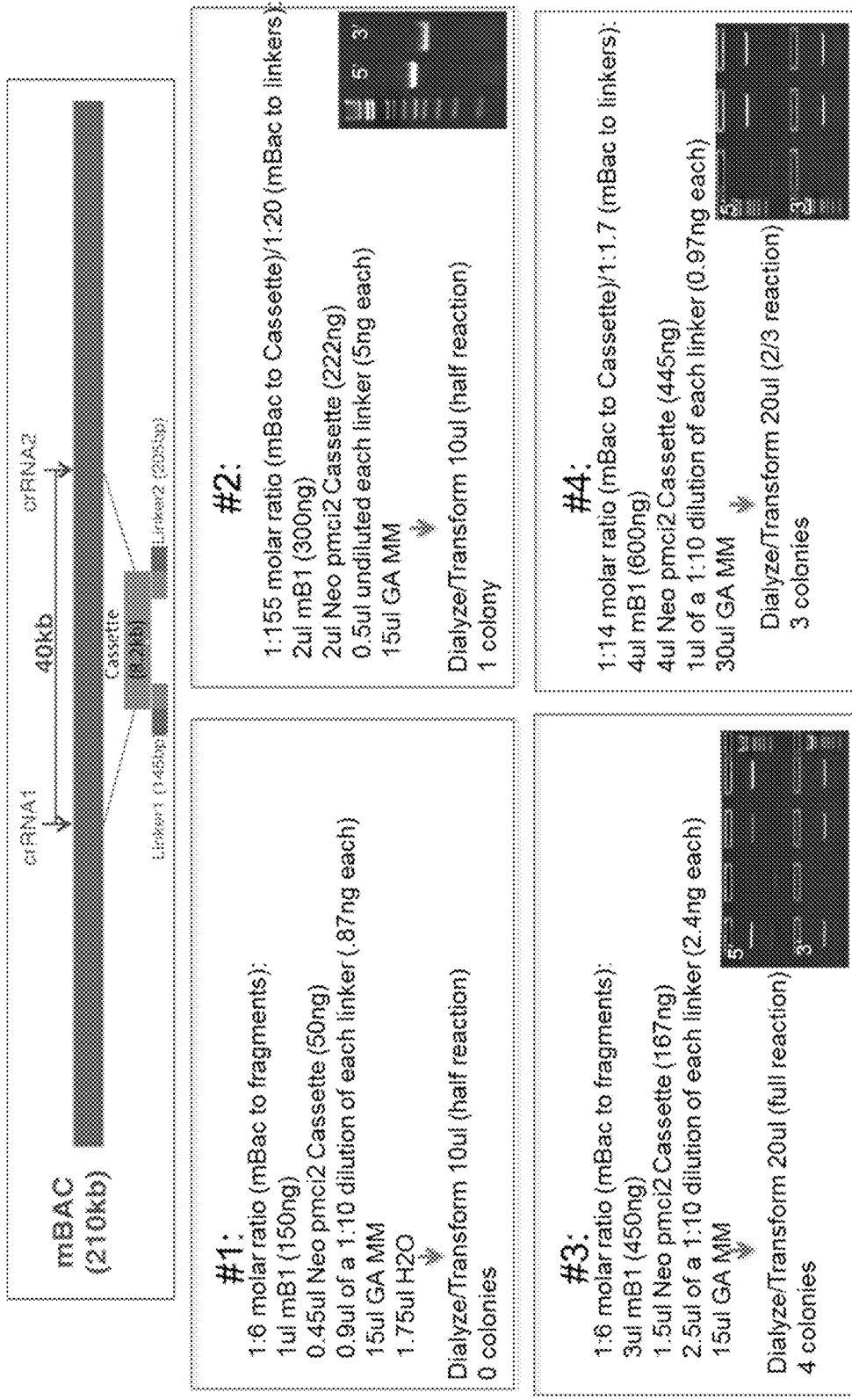

FIG. 9 shows the construction of a targeting vector for replacement of a portion of a BAC vector with a cassette using isothermal assembly and two linkers (joiner oligos). The results of various ratios of mBAC to fragments or linkers are presented in panels #1, #2, #3, and #4.

Figure 10:
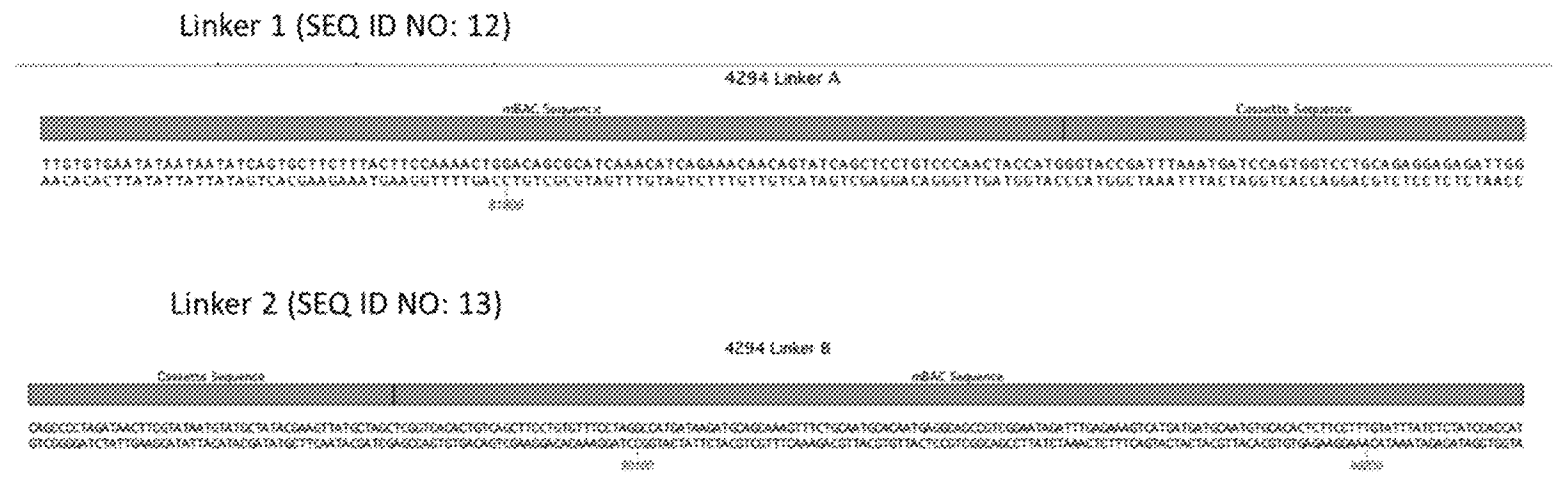

FIG. 10 shows the sequence confirmation of seamless assembly across both junctions of the assembly reaction between an mBAC (BAC ID: RP23-399M19) and a cassette using two linkers.

Figure 11:
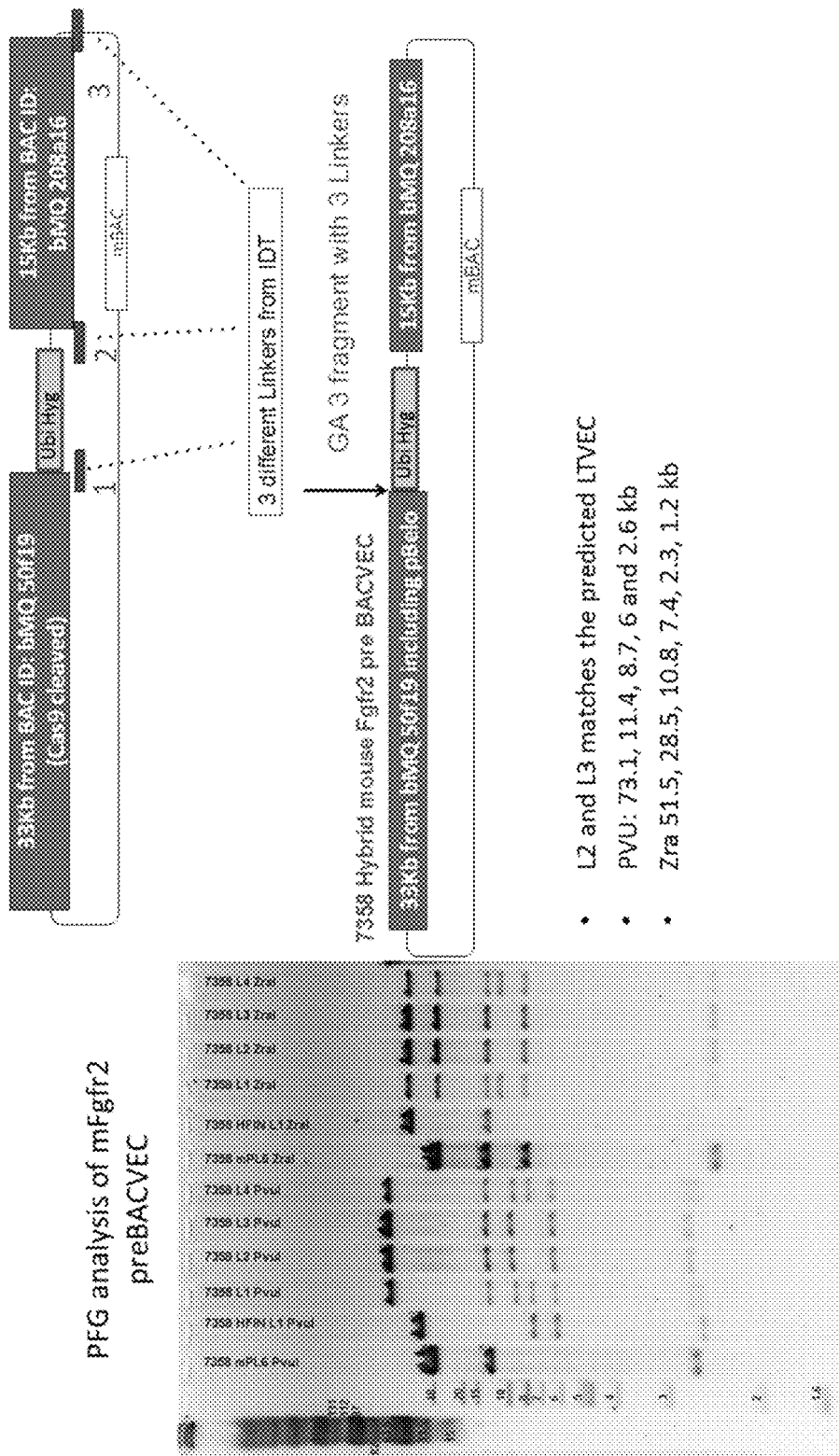

FIG. 11 shows the assembly of two mBACs using Cas9 and isothermal assembly. Assembly between the bMQ50f19 vector and the cassette comprising a hygromycin resistance gene ubiquitin promoter was seamless.

Figure 12:
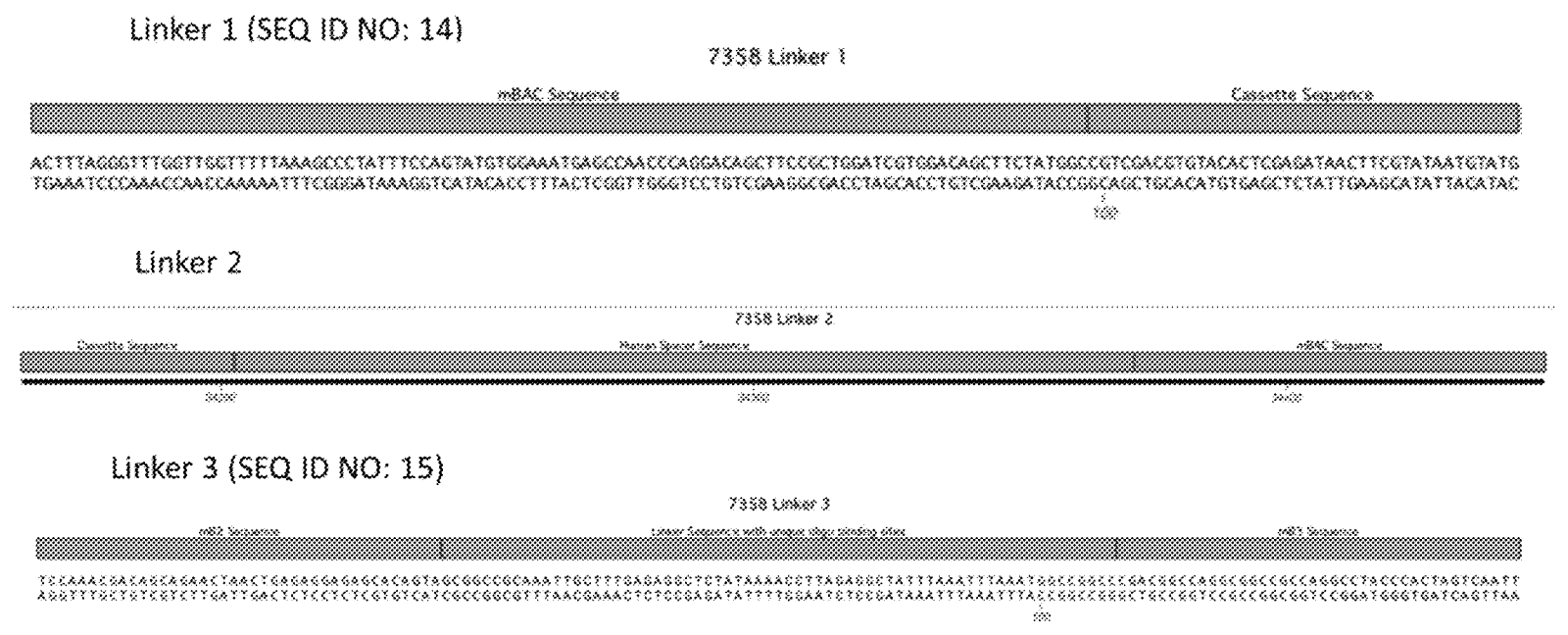

FIG. 12 shows the sequence confirmation of seamless assembly at linker 1, and sequence confirmation of assembly that was intentionally not seamless at linker 2 and linker 3.

Figure 13:
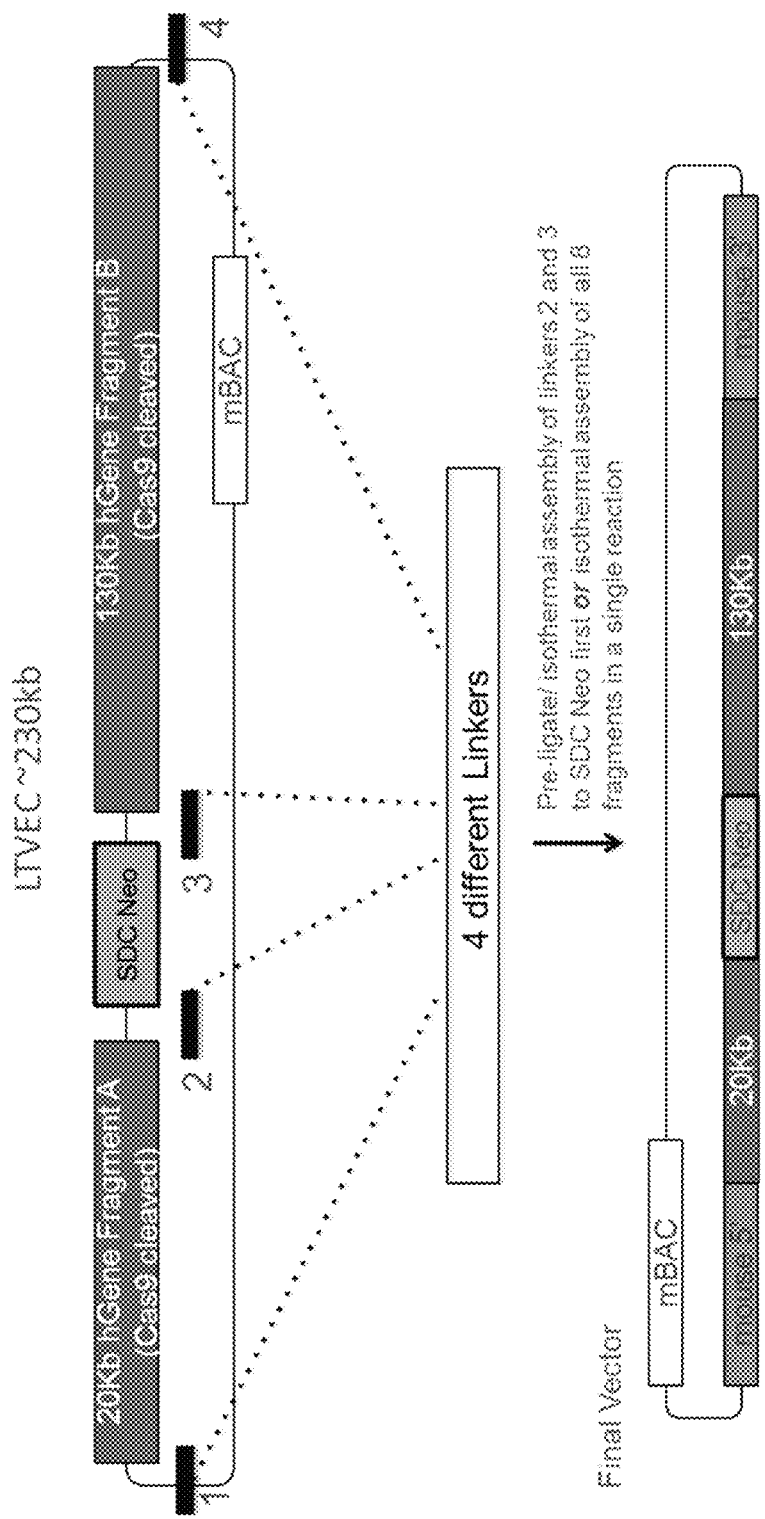

FIG. 13 shows the insertion of large human gene fragments onto a mBAC using four linkers and isothermal assembly. Cas9 cleaved hGene fragment A from hBAC1, hGene Fragment B from hBAC2, and mBAC to remove mGene fragments.

Figure 14:
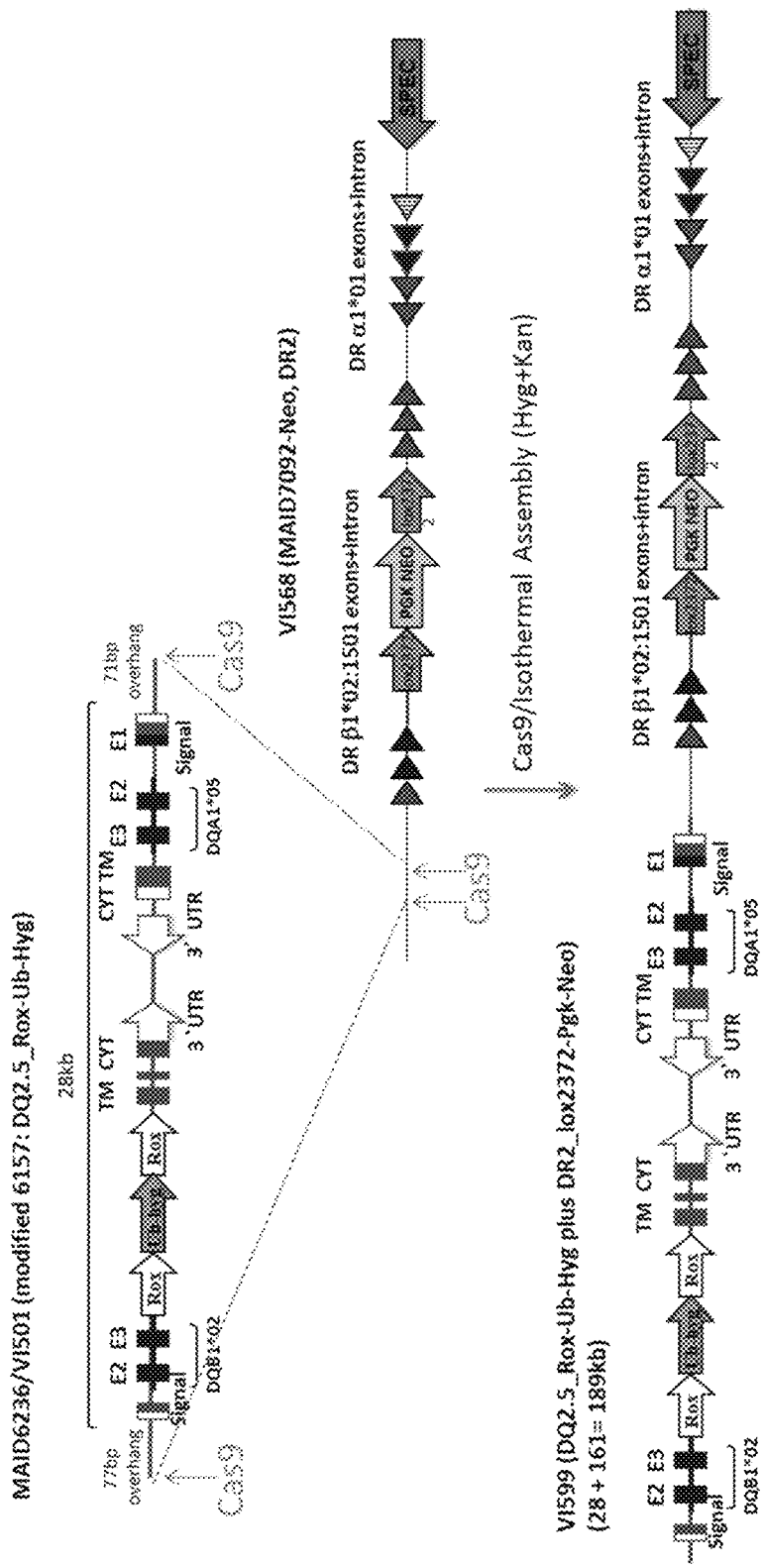

FIG. 14 shows the insertion of human sequence into a BAC vector using Cas9 and Isothermal Assembly.

Figure 15:
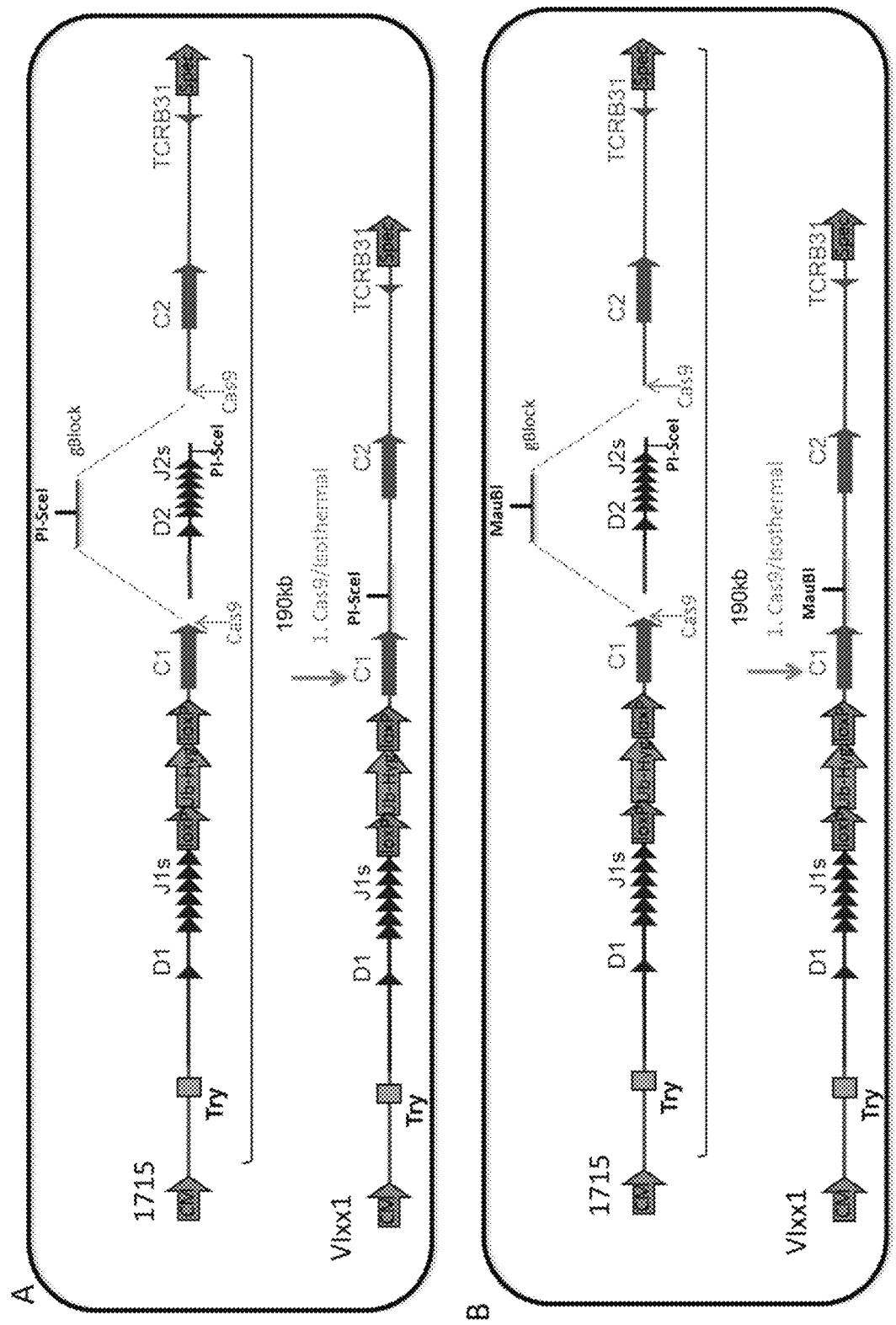

FIG. 15 shows the insertion of a gBlock comprising a meganuclease site using Cas9 and Isothermal Assembly. FIG. 15A shows the insertion of a gBlock comprising a PI-SceI site; and FIG. 15B shows the insertion of a gBlock comprising a MauBI site.

Figure 16:
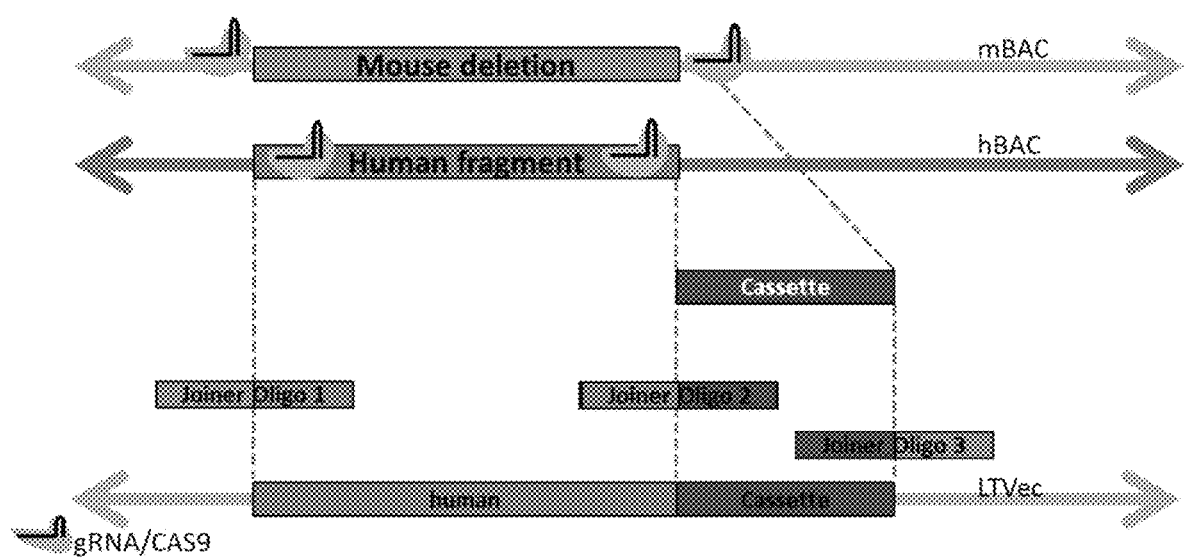

FIG. 16 illustrates an example of direct humanization of a targeting vector using three joiner oligos, Cas9, and isothermal assembly.

Figure 17:
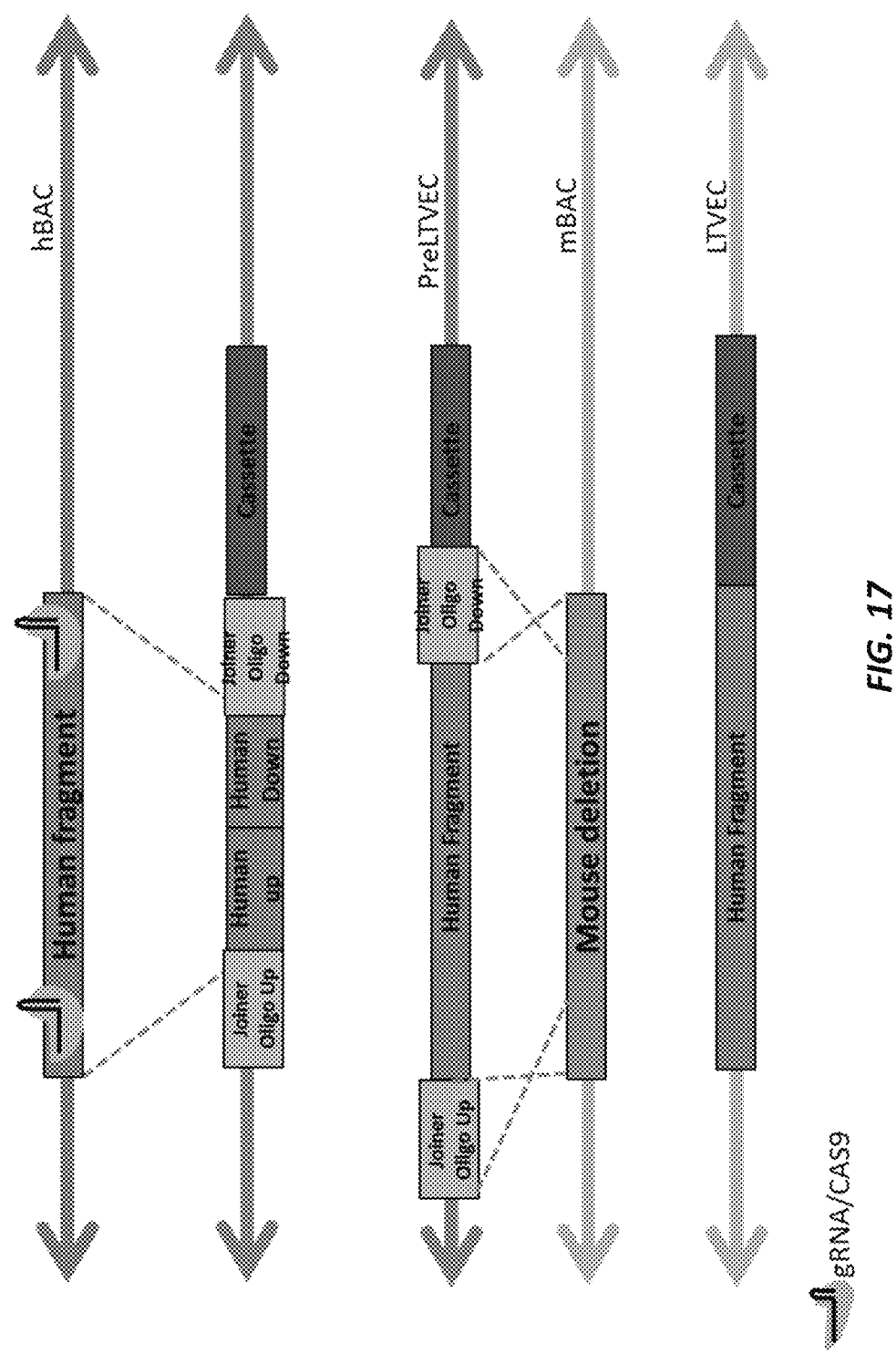

FIG. 17 illustrates an example of indirect humanization of a targeting vector using a donor with up and down joiner oligos, Cas9, and isothermal assembly.

Figure 18:
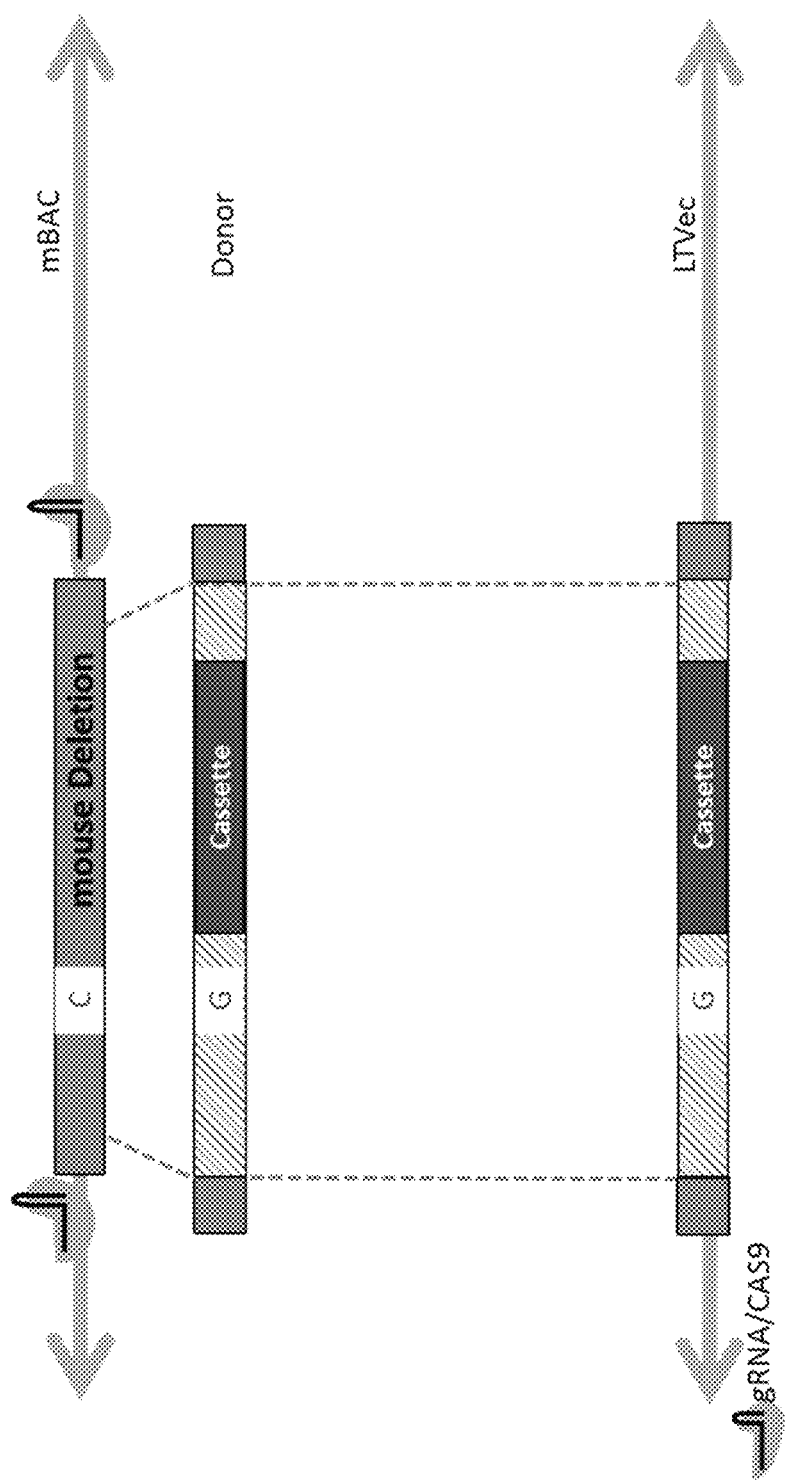

FIG. 18 illustrates an example of introducing a point mutation using Cas9 and Isothermal Assembly.

Figure 19:
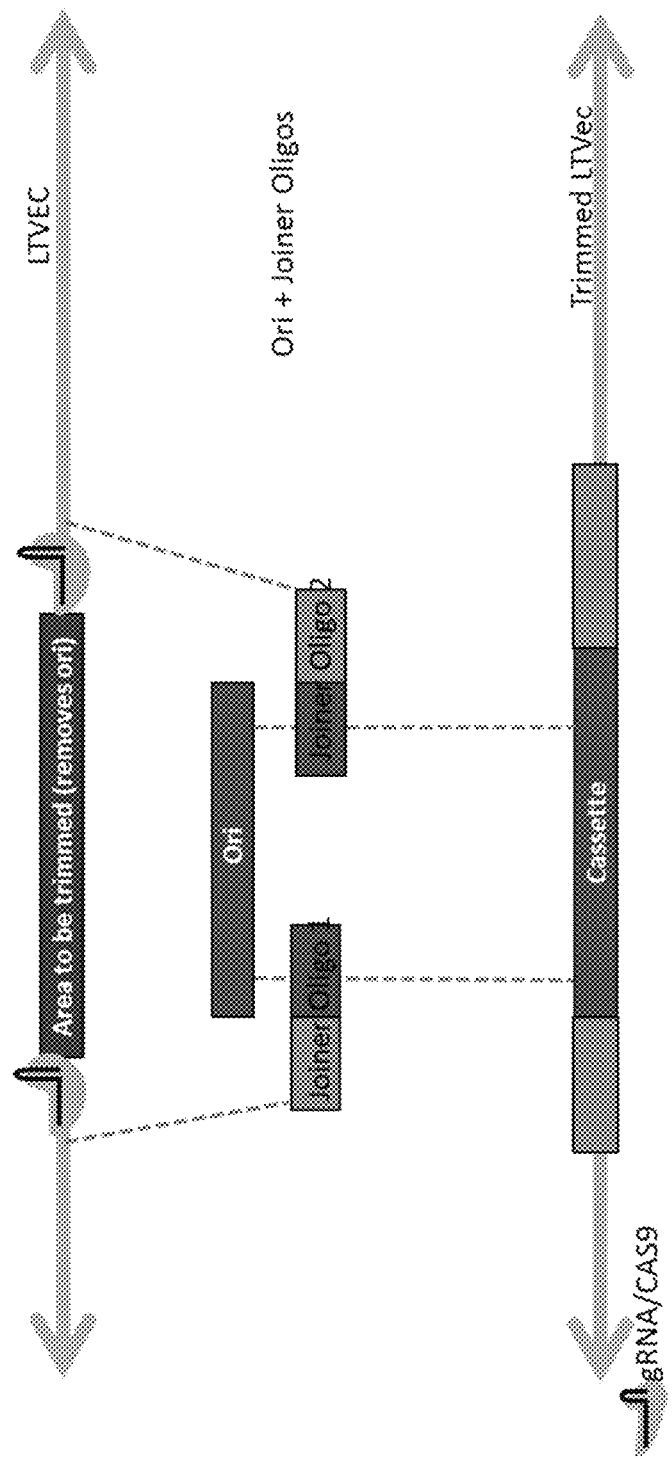

FIG. 19 illustrates an example of BAC trimming by Cas9 and isothermal assembly. In this example, the trimming removes the Ori sequence. The Ori sequence is re-inserted in the vector using two joiner oligos and isothermal assembly.

DETAILED DESCRIPTION

I. Definitions

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

"Codon optimization" generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292. Computer algorithms for codon optimization of a particular sequence for expression in a particular host are also available (see, e.g., Gene Forge).

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors.

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm includes the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989).

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs known in the art (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. It is recognized throughout the description that some components can have active variants and fragments. Such components include, for example, Cas proteins, CRISPR RNAs, tracrRNAs, and guide RNAs. Biological activity for each of these components is described elsewhere herein.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The singular forms of the articles "a," "an," and "the" include plural references unless the context clearly dictates otherwise. For example, the term "a Cas protein" or "at least one Cas protein" can include a plurality of Cas proteins, including mixtures thereof.

II. General

Figure 3:
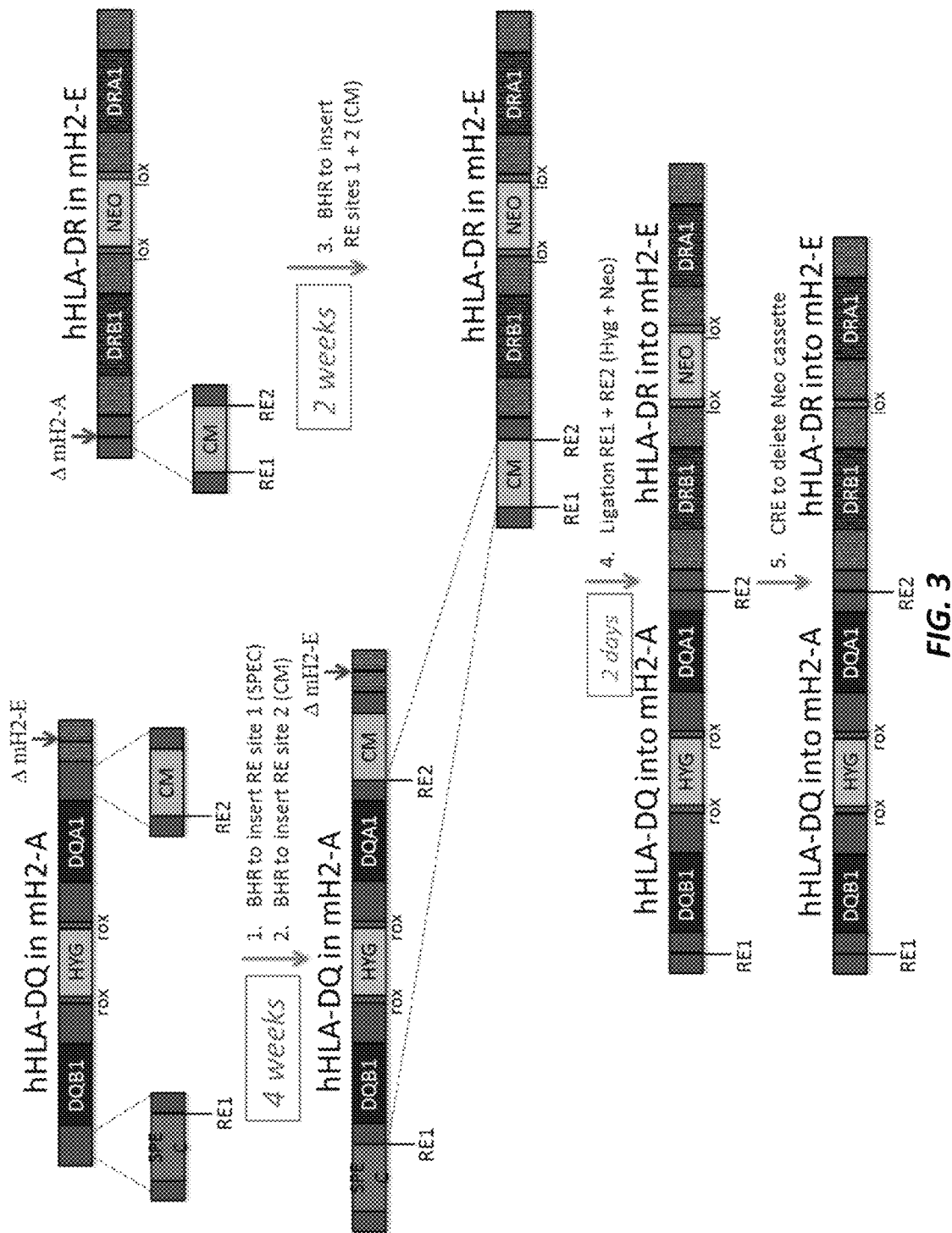
FIG. 3 shows assembly of two BACs with overlapping sequences using traditional methods. The process of assembly using traditional methods took 4 weeks.

Traditional methods of assembling nucleic acids employ time consuming steps of conventional enzymatic digestion with restriction enzymes, cloning of the nucleic acids, and ligating nucleic acids together (see, FIG. 3 and FIG. 4 for an illustration of traditional methods and timeline). These methods are made more difficult when large fragments or vectors are being assembled together. The methods provided herein take advantage of the malleable target specificity of nucleases (e.g., guide RNAs and Cas9 nucleases) to convert nucleic acids into a form suitable for use in rapid assembly reactions.

Provided herein are methods for assembling at least two nucleic acids using nuclease agents directed to specific target sites, such as by guide RNA (gRNA) (e.g., Cas protein directed to specific target sites by guide RNA (gRNA)). Site directed nuclease agents, for example, guide RNA-directed Cas proteins, allow rapid and efficient combination of nucleic acids by selecting and manipulating the end sequences generated by their endonuclease activity. The methods provided herein combine a first polynucleotide with a nuclease agent (e.g., a gRNA-Cas complex) specific for a desired target site and an exonuclease. The target site can be chosen such that when the nuclease cleaves the nucleic acid, the resulting ends created by the cleavage have regions complementary to the ends of the second nucleic acid (e.g., overlapping ends). These complementary ends can then be assembled to yield a single assembled nucleic acid. Because the nuclease agent (e.g., gRNA-Cas complex) is specific for an individual target site, the present method allows for modification of nucleic acids in a precise site-directed manner. The present method further takes advantage of nuclease agent, for example, a gRNA-Cas complex, specificity by utilizing rapid and efficient assembly methods specially designed for combining overlapping nucleic acid ends generated by nuclease cleavage or designed and synthesized for the assembly reaction. For example, by selecting a nuclease agent (e.g., a gRNA-Cas complex) specific for a target site such that, on cleavage, end sequences complementary to those of a second nucleic acid are produced, isothermal assembly can be used to assemble the resulting digested nucleic acid. Thus, by selecting nucleic acids and nuclease agents (e.g., gRNA-Cas complexes) that result in overlapping end sequences, nucleic acids can be assembled by rapid combinatorial methods to produce the final assembled nucleic acid in a fast and efficient manner. Alternatively, nucleic acids not having complementary ends can be assembled with joiner oligos designed to have complementary ends to each nucleic acid. By using the joiner oligos, two or more nucleic acids can be seamlessly assembled, thereby reducing unnecessary sequences in the resulting assembled nucleic acid.

III. Nuclease Agent

The present methods employ a nuclease agent for site-directed cleavage of polynucleotides. Specifically, endonuclease cleavage of polynucleotides at an identified target site produces a digested polynucleotide with ends that can then be joined to a second polynucleotide to assemble two or more polynucleotides in a site-specific manner.

"Nuclease agent" includes molecules which possesses activity for DNA cleavage. Particular examples of nuclease agents for use in the methods disclosed herein include RNA-guided CRISPR-Cas9 system, zinc finger proteins, meganucleases, TAL domains, TALENs, yeast assembly, recombinases, leucine zippers, CRISPR/Cas, endonucleases, and other nuclease agents known to those in the art. Nuclease agents can be selected or designed for specificity in cleaving at a given target site. For example, nuclease agents can be selected for cleavage at a target site that creates overlapping ends between the cleaved polynucleotide and a different polynucleotide. Nuclease agents having both protein and RNA elements as in CRISPR-Cas9 can be supplied with the agents already complexed as a nuclease agent, or can be supplied with the protein and RNA elements separate, in which case they complex to form a nuclease agent in the reaction mixtures described herein.

The term "recognition site for a nuclease agent" includes a DNA sequence at which a nick or double-strand break is induced by a nuclease agent. The recognition site for a nuclease agent can be endogenous (or native) to the cell or the recognition site can be exogenous to the cell. In specific embodiments, the recognition site is exogenous to the cell and thereby is not naturally occurring in the genome of the cell. In still further embodiments, the recognition site is exogenous to the cell and to the polynucleotides of interest that one desires to be positioned at the target locus. In further embodiments, the exogenous or endogenous recognition site is present only once in the genome of the host cell. In specific embodiments, an endogenous or native site that occurs only once within the genome is identified. Such a site can then be used to design nuclease agents that will produce a nick or double-strand break at the endogenous recognition site.

The length of the recognition site can vary, and includes, for example, recognition sites that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

Active variants and fragments of the exemplified recognition sites are also provided. Such active variants can comprise at least 65%, 70%, 75%, 80%, 85%, 90%, 91%, 92%, 93%, 94%, 95%, 96%, 97%, 98%, 99% or more sequence identity to the given recognition site, wherein the active variants retain biological activity and hence are capable of being recognized and cleaved by a nuclease agent in a sequence-specific manner. Assays to measure the double-strand break of a recognition site by a nuclease agent are known in the art (e.g., TaqMan® qPCR assay, Frendewey D. et al., Methods in Enzymology, 2010, 476: 295-307, which is incorporated by reference herein in its entirety).

In specific embodiments, the recognition site is positioned within the polynucleotide encoding the selection marker. Such a position can be located within the coding region of the selection marker or within the regulatory regions, which influence the expression of the selection marker. Thus, a recognition site of the nuclease agent can be located in an intron of the selection marker, a promoter, an enhancer, a regulatory region, or any non-protein-coding region of the polynucleotide encoding the selection marker. In specific embodiments, a nick or double-strand break at the recognition site disrupts the activity of the selection marker. Methods to assay for the presence or absence of a functional selection marker are known.

Any nuclease agent that induces a nick or double-strand break into a desired recognition site can be used in the methods and compositions disclosed herein. A naturally-occurring or native nuclease agent can be employed so long as the nuclease agent induces a nick or double-strand break in a desired recognition site. Alternatively, a modified or engineered nuclease agent can be employed. An "engineered nuclease agent" comprises a nuclease that is engineered (modified or derived) from its native form to specifically recognize and induce a nick or double-strand break in the desired recognition site. Thus, an engineered nuclease agent can be derived from a native, naturally-occurring nuclease agent or it can be artificially created or synthesized. The modification of the nuclease agent can be as little as one amino acid in a protein cleavage agent or one nucleotide in a nucleic acid cleavage agent. In some embodiments, the engineered nuclease induces a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

These breaks can then be repaired by the cell in one of two ways: non-homologous end joining and homology-directed repair (homologous recombination). In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence can be used as a template for repair of the cleaved target DNA sequence, resulting in the transfer of genetic information from the donor polynucleotide to the target DNA. Therefore, new nucleic acid material may be inserted/copied into the site. The modifications of the target DNA due to NHEJ and/or homology-directed repair can be used for gene correction, gene replacement, gene tagging, transgene insertion, nucleotide deletion, gene disruption, gene mutation, etc.

In one embodiment, the nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FoId. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/ pnas.1013133107; Scholze & Boch (2010) *Virulence* 1:428-432; Christian et al. *Genetics* (2010) 186:757-761; Li et al. (2010) *Nuc. Acids Res.* (2010) doi:10.1093/nar/gkq704; and Miller et al. (2011) *Nature Biotechnology* 29:143-148; all of which are herein incorporated by reference.

Examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference). In various embodiments, TAL effector nucleases are engineered that cut in or near a target nucleic acid sequence in, e.g., a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In one embodiment, each monomer of the TALEN comprises 33-35 TAL repeats that recognize a single base pair via two hypervariable residues. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease subunit, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FoId nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, for example, US20060246567; US20080182332; US20020081614; US20030021776; WO/2002/057308A2; US20130123484; US20100291048; WO/2011/017293A2; and Gaj et al. (2013) *Trends in Biotechnology*, 31(7):397-405, each of which is herein incorporated by reference.

In one embodiment of the methods provided herein, the nuclease agent comprises (a) a chimeric protein comprising a zinc finger-based DNA binding domain fused to a FoId endonuclease; or, (b) a chimeric protein comprising a Transcription Activator-Like Effector Nuclease (TALEN) fused to a FokI endonuclease.

In still another embodiment, the nuclease agent is a meganuclease. Meganucleases have been classified into four families based on conserved sequence motifs, the families are the LAGLIDADG (SEQ ID NO: 16), GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. Meganuclease domains, structure and function are known, see for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG (SEQ ID NO: 16) family of homing nuclease. In one embodiment, the LAGLIDADG (SEQ ID NO: 16) family of homing nuclease is selected from I-SceI, I-CreI, and I-DmoI.

Nuclease agents can further comprise restriction endonucleases (restriction enzymes), which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) *Nucleic Acids Res* 31:418-20), Roberts et al., (2003) *Nucleic Acids Res* 31:1805-12, and Belfort et al., (2002) in *Mobile DNA II*, pp. 761-783, Eds. Craigie et al., (ASM Press, Washington, D.C.). In specific embodiments, at least two endonuclease enzymes can be selected as the nuclease agents wherein the enzymes create compatible, or complementary, sticky ends.

The nuclease agent employed in the various methods and compositions can also comprise a CRISPR/Cas system. Such systems can employ a Cas9 nuclease, which in some instances, is codon-optimized for the desired cell type in which it is to be expressed. The system further employs a fused crRNA-tracrRNA construct that functions with the codon-optimized Cas9. This single RNA is often referred to as a guide RNA or gRNA. Within a gRNA, the crRNA portion is identified as the 'target sequence' for the given recognition site and the tracrRNA is often referred to as the 'scaffold'. This system has been shown to function in a variety of eukaryotic and prokaryotic cells. Briefly, a short DNA fragment containing the target sequence is inserted into a guide RNA expression plasmid. The gRNA expression plasmid comprises the target sequence (in some embodiments around 20 nucleotides), a form of the tracrRNA sequence (the scaffold) as well as a suitable promoter that is active in the cell and necessary elements for proper processing in eukaryotic cells. Many of the systems rely on custom, complementary oligos that are annealed to form a double stranded DNA and then cloned into the gRNA expression plasmid. The gRNA expression cassette and the Cas9 expression cassette are then introduced into the cell. See, for example, Mali P et al. (2013) *Science* 2013 Feb. 15; 339 (6121):823-6; Jinek M et al. *Science* 2012 Aug. 17; 337 (6096):816-21; Hwang W Y et al. *Nat Biotechnol* 2013 March; 31(3):227-9; Jiang W et al. *Nat Biotechnol* 2013 March; 31(3):233-9; and, Cong L et al. *Science* 2013 Feb. 15; 339(6121):819-23, each of which is herein incorporated by reference.

The methods and compositions disclosed herein can utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

Some CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

Active variants and fragments of nuclease agents (i.e. an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus, in some embodiments, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

IV. CRISPR/Cas Systems (gRNA-Cas Complex)

The present methods can employ a CRISPR/Cas system (e.g., gRNA-Cas complex) for site-directed cleavage of nucleic acids. Specifically, Cas cleavage of nucleic acids directed by gRNA to an identified target site produces a digested nucleic acid with ends that can then be joined to a second nucleic acid to assemble two or more nucleic acids in a site-specific manner.

A "gRNA-Cas complex" includes a complex of a Cas protein with a gRNA. The gRNA can be designed or selected to direct Cas cleavage to a target site that creates overlapping ends between the cleaved nucleic acid and a different nucleic acid. The gRNA-Cas complex can be supplied with the agents already complexed, or can be supplied with the protein and RNA elements separate, in which case they complex to form a gRNA-Cas complex in the methods and reaction mixtures described herein.

A. Cas RNA-Guided Endonucleases

Cas proteins generally comprise at least one RNA recognition or binding domain. Such domains can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

Any Cas protein that induces a nick or double-strand break into a desired recognition site can be used in the methods and compositions disclosed herein. A naturally-occurring or native Cas protein can be employed so long as the Cas protein induces double-strand break at a desired recognition site. Alternatively, a modified or engineered Cas protein can be employed. An "engineered Cas protein" comprises a Cas protein that is engineered (modified or derived) from its native form to specifically recognize and induce a nick or double-strand break in the desired recognition site. Thus, an engineered Cas protein can be derived from a native, naturally-occurring Cas protein or it can be artificially created or synthesized.

In particular embodiments, the Cas protein is Cas9. Cas9 proteins typically share four key motifs with a conserved architecture. Motifs 1, 2, and 4 are RuvC-like motifs, and motif 3 is an HNH motif. The nuclease activity of Cas9 cleaves target DNA to produce double strand breaks. These breaks can then be repaired by the cell in one of two ways: non-homologous end joining and homology-directed repair (homologous recombination). In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence can be used as a template for repair of the cleaved target DNA sequence, resulting in the transfer of genetic information from the donor polynucleotide to the target DNA. Therefore, new nucleic acid material may be inserted/copied into the site. The modifications of the target DNA due to NHEJ and/or homology-directed repair can be used for gene correction, gene replacement, gene tagging, transgene insertion, nucleotide deletion, gene disruption, gene mutation, etc.

Cas proteins can be from a type II CRISPR/Cas system. For example, the Cas protein can be a Cas9 protein or be derived from a Cas9 protein. Cas9 proteins typically share four key motifs with a conserved architecture. Motifs 1, 2, and 4 are RuvC-like motifs, and motif 3 is an HNH motif. The Cas9 protein can be from, for example, *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.* Additional examples of the Cas9 family members are described in WO 2014/131833, herein incorporated by reference in its entirety. Cas9 protein from *S. pyogenes* or derived therefrom is a preferred enzyme. Cas9 protein from *S. pyogenes* is assigned SwissProt accession number Q99ZW2.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Some Cas proteins comprise at least two nuclease domains, such as DNase domains. For example, a Cas9 protein can comprise a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, hereby incorporated by reference in its entirety.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single-strand break at a CRISPR RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA. An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety. Such mutations can be generated using methods such as site-directed mutagenesis, PCR-mediated mutagenesis, or total gene synthesis. Examples of other mutations creating nickases can be found, for example, in WO/2013/176772A1 and WO/2013/142578A1, each of which is herein incorporated by reference.

Cas proteins can also be fusion proteins. For example, a Cas protein can be fused to a cleavage domain, an epigenetic modification domain, a transcriptional activation domain, or a transcriptional repressor domain. See WO 2014/089290, incorporated herein by reference in its entirety. Cas proteins can also be fused to a heterologous polypeptide providing increased or decreased stability. The fused domain or heterologous polypeptide can be located at the N-terminus, the C-terminus, or internally within the Cas protein.

A Cas protein can be fused to a heterologous polypeptide that provides for subcellular localization. Such heterologous peptides include, for example, a nuclear localization signal (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, for example, WO 2014/089290, herein incorporated by reference in its entirety. The cell-penetrating domain can be located at the N-terminus, the C-terminus, or anywhere within the Cas protein.

Cas proteins can also comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g. eBFP, eBFP2, Azurite, mKalamal, GFPuv, Sapphire, T-sapphire), cyan fluorescent proteins (e.g. eCFP, Cerulean, CyPet, AmCyanl, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

In some embodiments, the Cas protein can be modified such that the resulting nuclease activity is altered. Certain mutations in Cas can reduce the ability of the nuclease to cleave both the complementary and the non-complementary strands of the target DNA. For example, Cas proteins can be mutated in known positions such that nuclease activity is limited to cleavage of either the complementary strand or the non-complementary strand. Specifically, Cas9 having a D10A (aspartate to alanine at amino acid position 10 of Cas9) mutation can cleave the complementary strand of the target DNA but has reduced ability to cleave the non-complementary strand of the target DNA. In some embodiments, Cas9 having a H840A (histidine to alanine at amino acid position 840) mutation can cleave the non-complementary strand of the target DNA but has reduced ability to cleave the complementary strand of the target DNA. The nuclease activity of Cas9 having either a D10A or H840A mutation would result in a single strand break (SSB) instead of a DSB. Other residues can be mutated to achieve the same effect (i.e. inactivate one or the other nuclease portions). As non-limiting examples, residues D10, G12, G17, E762, H840, N854, N863, H982, H983, A984, D986, and/or A987 (i.e., substituted). Further, substitute amino acids other than alanine can be suitable. In some embodiments when a nuclease has reduced activity (e.g., when a Cas9 protein has a D10, G12, G17, E762, H840, N854, N863, H982, H983, A984, D986, and/or a A987 mutation, such as D10A, G12A, G17A, E762A, H840A, N854A, N863A, H982A, H983A, A984A, and/or D986A), the nuclease can still bind to target DNA in a site-specific manner because it is still guided to a target DNA sequence by a gRNA) as long as it retains the ability to interact with the gRNA.

In some embodiments, Cas is altered such that the nuclease does not cleave either the complementary or non-complementary strand of target DNA. For example, Cas9 with both the D10A and the H840A mutations has a reduced ability to cleave both the complementary and the non-complementary strands of the target DNA. Other residues can be mutated to achieve the same effect (i.e., inactivate one or the other nuclease portions). As non-limiting examples, residues D10, G12, G17, E762, H840, N854, N863, H982, H983, A984, D986, and/or can be substituted in order to substantially eliminate nuclease activity. Further, mutations other than alanine substitutions can be suitable.

The terms "target site" or "target sequence" can be used interchangeably and include nucleic acid sequences present in a target DNA to which a DNA-targeting segment of a gRNA will bind, provided sufficient conditions for binding exist. For example, the target site (or target sequence) within a target DNA is targeted by (or is bound by, or hybridizes with, or is complementary to) the Cas protein or gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001)). The strand of the target DNA that is complementary to and hybridizes with the Cas protein or gRNA is referred to as the "complementary strand" and the strand of the target DNA that is complementary to the "complementary strand" (and is therefore not complementary to the Cas protein or gRNA) is referred to as the "noncomplementary strand" or "template strand".

The Cas protein may cleave the nucleic acid at a site within the target sequence or outside of the target sequence. The "cleavage site" includes the position of a nucleic acid wherein a Cas protein produces a single-strand break or a double-strand break. If the Cas protein produces a double-strand break, the cleavage site can be at the same position on both strands of the nucleic acid (producing blunt ends) or can be at different sites on each strand (producing sticky or cohesive ends). Sticky ends can also be produced by using two Cas proteins which produce a single-strand break at cleavage sites on each strand. Site-specific cleavage of target DNA by Cas9 can occur at locations determined by both (i) base-pairing complementarity between the guide RNA and the target DNA; and (ii) a short motif, referred to as the protospacer adjacent motif (PAM), in the target DNA. For example, the cleavage site of Cas9 can be about 1 to about 10 or about 2 to about 5 base pairs (e.g., 3 base pairs) upstream of the PAM sequence. In some embodiments (e.g., when Cas9 from *S. pyogenes*, or a closely related Cas9, is used), the PAM sequence of the non-complementary strand can be 5'-XGG-3', where X is any DNA nucleotide and X is immediately 3' of the target sequence of the non-complementary strand of the target DNA. As such, the PAM sequence of the complementary strand would be 5'-CCY-3', where Y is any DNA nucleotide and Y is immediately 5' of the target sequence of the complementary strand of the target DNA. In some such embodiments, X and Y can be complementary and the X-Y base pair can be any basepair (e.g., X=C and Y=G; X=G and Y=C; X=A and Y=T, X=T and Y=A).

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in the targeting vector comprising the nucleic acid insert and/or a vector comprising the DNA encoding the gRNA, or it can be in a vector or a plasmid that is separate from the targeting vector comprising the nucleic acid insert and/or separate from a vector comprising the DNA encoding the gRNA. Promoters that can be used in an expression construct include, for example, promoters active in a pluripotent rat, eukaryotic, mammalian, non-human mammalian, human, rodent, mouse, or hamster cell. Such promoters can be, for example, conditional promoters, inducible promoters, constitutive promoters, or tissue-specific promoters. Examples of other promoters are described elsewhere herein.

B. Guide RNAs (gRNAs)

A "guide RNA" or "gRNA" includes a RNA molecule that binds to a Cas protein and targets the Cas protein to a specific location within a target DNA. Guide RNAs (gRNA) can comprise two segments, a "DNA-targeting segment" and a "protein-binding segment." "Segment" includes a segment, section, or region of a molecule, such as a contiguous stretch of nucleotides in an RNA. Some gRNAs comprise two separate RNA molecules: an "activator-RNA" and a "targeter-RNA". Other gRNAs are a single RNA molecule (single RNA polynucleotide), which can also be called a "single-molecule gRNA," a "single-guide RNA," or an "sgRNA." See, e.g., WO/2013/176772A1, WO/2014/065596A1, WO/2014/089290A1, WO/2014/093622A2, WO/2014/099750A2, WO/2013142578A1, and WO 2014/131833A1, each of which is herein incorporated by reference. The terms "guide RNA" and "gRNA" include both double-molecule gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNAlike ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA. A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. The crRNA additionally provides the single stranded DNA-targeting segment. Accordingly, a gRNA comprises a sequence that hybridizes to a target sequence, and a tracrRNA.

The crRNA and the corresponding tracrRNA (as a corresponding pair) hybridize to form a gRNA. The crRNA additionally provides the single-stranded DNA-targeting segment that hybridizes to a CRISPR RNA recognition sequence. If used for modification within a cell, the exact sequence of a given crRNA or tracrRNA molecule can be designed to be specific to the species in which the RNA molecules will be used. See, for example, Mali P et al. (2013) Science 2013 Feb. 15; 339(6121):823-6; Jinek M et al. Science 2012 Aug. 17; 337(6096):816-21; Hwang W Y et al. Nat Biotechnol 2013 March; 31(3):227-9; Jiang W et al. Nat Biotechnol 2013 March; 31(3):233-9; and, Cong L et al. Science 2013 Feb. 15; 339(6121):819-23, each of which is herein incorporated by reference.

The DNA-targeting segment (crRNA) of a given gRNA comprises a nucleotide sequence that is complementary to a sequence in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the Cas9 system and organism but often contain a targeting segment of between 21 to 72 nucleotides length, flanked by two direct repeats (DR) of a length of between 21 to 46 nucleotides (see, e.g., WO2014/131833). In the case of S. pyogenes, the DRs are 36 nucleotides long and the targeting segment is 30 nucleotides long. The 3' located DR is complementary to and hybridizes with the corresponding tracrRNA, which in turn binds to the Cas9 protein.

The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. Alternatively, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting segment that is complementary to a nucleotide sequence (CRISPR RNA recognition sequence) of the target DNA can have a length at least about 12 nt. For example, the DNA-targeting sequence (e.g., the sequence within the DNA-targeting segment that is complementary to a CRISPR RNA recognition sequence within the target DNA) can have a length at least about 12 nt, at least about 15 nt, at least about 18 nt, at least about 19 nt, at least about 20 nt, at least about 25 nt, at least about 30 nt, at least about 35 nt, or at least about 40 nt. Alternatively, the DNA-targeting sequence of the DNA-targeting segment that is complementary to a target sequence of the target DNA can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. The nucleotide sequence (the DNA-targeting sequence) of the DNA-targeting segment that is complementary to a nucleotide sequence (target sequence) of the target DNA can have a length at least about 12 nt. In some cases, the DNA-targeting sequence can have a length of at least about 20 nt.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild-type tracrRNA sequence (e.g., about or more than about 20, 26, 32, 45, 48, 54, 63, 67, 85, or more nucleotides of a wild-type tracrRNA sequence). Examples of wild-type tracrRNA sequences from S. pyogenes include 171-nucleotide, 89-nucleotide, 75-nucleotide, and 65-nucleotide versions. See, for example, Deltcheva et al. (2011) Nature 471:602-607; WO 2014/093661, each of which is incorporated herein by reference in their entirety. Examples of tracrRNAs within single-guide RNAs (sgRNAs) include the tracrRNA segments found within +48, +54, +67, and +85 versions of sgRNAs, where "+n" indicates that up to the +n nucleotide of wild-type tracrRNA is included in the sgRNA. See U.S. Pat. No. 8,697,359, incorporated herein by reference in its entirety.

The percent complementarity between the DNA-targeting sequence and the CRISPR RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the CRISPR RNA recognition sequence within the target DNA is 100% over the seven contiguous 5'-most nucleotides of the target sequence of the complementary strand of the target DNA. In certain embodiments, the percent complementarity between the DNA-targeting sequence and the CRISPR RNA recognition sequence within the target DNA can be at least 60% over about 20 contiguous nucleotides. As an example, the percent complementarity between the DNA-targeting sequence and the CRISPR RNA recognition sequence within the target DNA is 100% over the fourteen contiguous nucleotides at the 5'-most end of the CRISPR RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the CRISPR RNA recognition sequence within the target DNA is 100% over the seven contiguous nucleotides at the 5'-most end of the CRISPR RNA recognition sequence within the complementary strand of the target DNA and as low as 0% over the remainder. In such a case, the DNA-targeting sequence can be considered to be 7 nucleotides in length.

Complementarity of nucleic acids means that a nucleotide sequence in one strand of nucleic acid, due to orientation of its nucleobase groups, hydrogen bonds to another sequence on an opposing nucleic acid strand. The complementary bases typically are, in DNA: A with T and C with G, and, in RNA: C with G, and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment (e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989)).

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, an gRNA in which 18 of 20 nucleotides of the gRNA are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The protein-binding segment of a subject gRNA interacts with a Cas protein. The subject gRNA directs the bound polypeptide to a specific nucleotide sequence within target DNA via the DNA-targeting segment. The protein-binding segment of a subject gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with the Cas protein, and the gRNA directs the bound Cas protein to a specific nucleotide sequence within the target DNA via the DNA-targeting segment.

In certain embodiments, a gRNA as described herein comprises two separate RNA molecules. Each of the two RNA molecules of a subject gRNA comprises a stretch of nucleotides that are complementary to one another such that the complementary nucleotides of the two RNA molecules hybridize to form the double stranded RNA duplex (e.g., hairpin) of the protein-binding segment. A subject gRNA can comprise any corresponding crRNA and tracrRNA pair. In the methods described herein, the gRNA can be used as a complex (e.g. gRNA-Cas complex) of crRNA and tracrRNA or the crRNA and corresponding tracrRNA can be delivered separately. For example, if multiple gRNAs are used for cleavage reaction, individual crRNAs specific for each target site can be delivered separately from a standard tracrRNA that can complex with each crRNA. In such a method, the crRNAs can complex with the standard tracrRNA in order to direct a Cas protein to the target site.

Guide RNAs can include modifications or sequences that provides for additional desirable features (e.g., modified or regulated stability; subcellular targeting; tracking, with a fluorescent label; a binding site for a protein or protein complex; and the like). Non-limiting examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the RNA. The DNA encoding the gRNA can encode a single RNA molecule (sgRNA) or separate RNA molecules (e.g., separate crRNA and tracrRNA). In the latter case, the DNA encoding the gRNA can be provided as separate DNA molecules encoding the crRNA and tracrRNA, respectively.

DNAs encoding gRNAs can be stably integrated in the genome of the cell and operably linked to a promoter active in the cell. Alternatively, DNAs encoding gRNAs can be operably linked to a promoter in an expression construct. For example, the DNA encoding the gRNA can be in the targeting vector comprising the nucleic acid insert and/or a vector comprising the nucleic acid encoding the Cas protein, or it can be in a vector or a plasmid that is separate from the targeting vector comprising the nucleic acid insert and/or separate from a vector comprising the nucleic acid encoding the Cas protein. Such promoters can be active, for example, in a pluripotent rat, eukaryotic, mammalian, non-human mammalian, human, rodent, mouse, or hamster cell. Such promoters can be, for example, conditional promoters, inducible promoters, constitutive promoters, or tissue-specific promoters. In some instances, the promoter is an RNA polymerase III promoter, such as a human U6 promoter, a rat U6 polymerase III promoter, or a mouse U6 polymerase III promoter. Examples of other promoters are described elsewhere herein. When a DNA encoding a gRNA is introduced into the cell, the gRNA can be transiently, conditionally, or constitutively expressed in the cell.

Alternatively, gRNAs can be prepared by various other methods. For example, gRNAs can be prepared by in vitro transcription using, for example, T7 RNA polymerase (see, for example, WO 2014/089290 and WO 2014/065596). Guide RNAs can also be a synthetically produced molecule prepared by chemical synthesis.

C. CRISPR RNA Recognition Sequences

The term "CRISPR RNA recognition sequence" includes nucleic acid sequences present in a target DNA to which a DNA-targeting segment of a gRNA will bind, provided sufficient conditions for binding exist. For example, CRISPR RNA recognition sequences include sequences to which a guide RNA is designed to have complementarity, where hybridization between a CRISPR RNA recognition sequence and a DNA targeting sequence promotes the formation of a CRISPR complex. Full complementarity is not necessarily required, provided there is sufficient complementarity to cause hybridization and promote formation of a CRISPR complex. CRISPR RNA recognition sequences also include cleavage sites for Cas proteins, described in more detail below. A CRISPR RNA recognition sequence can comprise any polynucleotide, which can be located, for example, in the nucleus or cytoplasm of a cell or within an organelle of a cell, such as a mitochondrion or chloroplast.

The CRISPR RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., *Molecular Cloning: A Laboratory Manual,* 3rd Ed. (Sambrook et al., Harbor Laboratory Press 2001)). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a CRISPR RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "CRISPR RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends). Staggered ends can be produced, for example, by using two Cas proteins, each of which produces a single-strand break at a different cleavage site on each strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the CRISPR RNA recognition sequence of the nickase on the first strand is separated from the CRISPR RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the CRISPR RNA recognition sequence. Optionally, the CRISPR RNA recognition sequence can be flanked by the PAM. For example, the cleavage site of Cas9 can be about 1 to about 10 or about 2 to about 5 base pairs (e.g., 3 base pairs) upstream or downstream of the PAM sequence. In some cases (e.g., when Cas9 from S. pyogenes or a closely related Cas9 is used), the PAM sequence of the non-complementary strand can be 5'-$N_1$GG-3', where $N_1$ is any DNA nucleotide and is immediately 3' of the CRISPR RNA recognition sequence of the non-complementary strand of the target DNA. As such, the PAM sequence of the complementary strand would be 5'-CC $N_2$-3', where $N_2$ is any DNA nucleotide and is immediately 5' of the CRISPR RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T, $N_1$=T, and $N_2$=A).

Examples of CRISPR RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas protein, such as $GN_{19}$NGG (SEQ ID NO: 8) or $N_{20}$NGG (SEQ ID NO: 24) (see, for example, WO 2014/165825). The guanine at the 5' end can facilitate transcription by RNA polymerase in cells. Other examples of CRISPR RNA recognition sequences can include two guanine nucleotides at the 5' end (e.g., $GGN_{20}$NGG; SEQ ID NO: 25) to facilitate efficient transcription by T7 polymerase in vitro. See, for example, WO 2014/065596. Other CRISPR RNA recognition sequences can have between 4-22 nucleotides in length of SEQ ID NOS: 8, 24, and 25, including the 5' G or GG and the 3' GG or NGG. Yet other CRISPR RNA recognition sequences can have between 14 and 20 nucleotides in length of SEQ ID NOS: 8, 24, and 25.

The CRISPR RNA recognition sequence can be any nucleic acid sequence endogenous or exogenous to a cell. The CRISPR RNA recognition sequence can be a sequence coding a gene product (e.g., a protein) or a non-coding sequence (e.g., a regulatory sequence) or can include both.

In one embodiment, the Cas protein is a type I Cas protein. In one embodiment, the Cas protein is a type II Cas protein. In one embodiment, the type II Cas protein is Cas9. In one embodiment, the first nucleic acid sequence encodes a human codon-optimized Cas protein.

In one embodiment, the gRNA comprises a nucleic acid sequence encoding a crRNA and a tracrRNA. In specific embodiments, the Cas protein is Cas9. In some embodiments, the gRNA comprises (a) the chimeric RNA of the nucleic acid sequence 5'-GUUUUAGAGCUAGAAAUAG-CAAGUUAAAAU AAGGCUAGUCCGUUAUCAAC-UUGAAAAAGUGGCACCGAGUCGGUGCUUUU-3' (SEQ ID NO: 1); or, (b) the chimeric RNA of the nucleic acid sequence 5'-GUUUUAGAGCUAGAAAUAG-CAAGUUAAAAUAAGGCUAGUCCG-3' (SEQ ID NO: 2). In another embodiment, the crRNA comprises 5'-GUUUUAGAGCUAGAAAUAGCAAGUUAAAAU-3' (SEQ ID NO: 3); 5'-GUUUUAGAGCUAGAAAUAG-CAAGUUAAAAUAAG (SEQ ID NO: 4); or 5'-GAGUC-CGAGCAGAAGAAGAAGUUUUA-3' (SEQ ID NO: 5). In yet other embodiments, the tracrRNA comprises, 5'-AAGGCUAGUCCG-3' (SEQ ID NO: 6) or 5'-AAGGC-UAGUCCGU UAUCAACUUGAAAAAGUGGCACCGA-GUCGGUGCUUUU-3' (SEQ ID NO: 7).

V. Assembly of Polynucleotides

The methods disclosed herein can assemble at least two nucleic acids under conditions effective to join the DNA molecules to form a substantially intact or seamless double-stranded DNA molecule. Any nucleic acids of interest having overlapping sequences can be assembled according to the methods disclosed herein. For example, any DNA molecules of interest having overlapping sequences can be assembled, including DNAs which are naturally occurring, cloned DNA molecules, synthetically generated DNAs, etc. The joined DNA molecules may, if desired, be cloned (e.g., inserted) into a vector using a method of the invention. Assembling two nucleic acids includes any method of joining strands of two nucleic acids. For example, assembly includes joining digested nucleic acids such that strands from each nucleic acid anneal to the other and extension, in which each strand serves as a template for extension of the other.

In some embodiments, nucleic acids are assembled with a joiner oligo such that each nucleic acid is assembled to the joiner oligo instead of being assembled directly together. Assembly with a joiner oligo can position nucleic acid bases between the nucleic acids that are being assembled that are not part of the nucleic acids to be assembled, but are part of the joiner oligo. Thus, nucleic acids can be successfully assembled even if extra bases remain between the nucleic acids. Alternatively, a joiner oligo can be used for seamless assembly, wherein no extra bases remain between the nucleic acids to be assembled.

In some embodiments, the nucleic acids can be prepared for assembly by cleavage with a Cas protein, a restriction enzyme (restriction endonuclease) (e.g., any of the various restriction endonucleases provided elsewhere herein), a meganuclease (e.g., any of the various meganucleases provided elsewhere herein), or any combination thereof. For example, one of the nucleic acids to be assembled can be cleaved with a Cas protein and another nucleic acid to be assembled can be cleaved with a Cas protein, a restriction enzyme, a meganuclease, or any combination thereof. Following cleavage with a nuclease, the digested nucleic acid can be assembled directly to another digested nucleic acid having overlapping end sequences or assembled to a nucleic acid that has not been digested but has overlapping end sequences. The digested nucleic acid can also be assembled to another nucleic acid by using a joiner oligo.

In embodiments employing a nuclease agent (e.g., a Cas protein) to produce overlapping end sequences between two nucleic acid molecules, rapid combinatorial methods can be used to assemble the digested nucleic acids. For example, a first and a second nucleic acid having overlapping ends can be combined with a ligase, exonuclease, DNA polymerase, and nucleotides and incubated at a constant temperature, such as at 50° C. Specifically, a T5 exonuclease could be used to remove nucleotides from the 5' ends of dsDNA producing complementary overhangs. The complementary single-stranded DNA overhangs can then be annealed, DNA polymerase used for gap filling, and Taq DNA ligase used to seal the resulting nicks at 50° C. Thus, two nucleic acids sharing overlapping end sequences can be joined into a covalently sealed molecule in a one-step isothermal reaction. See, for example, Gibson, et al. (2009) *Nature Methods* 6(5): 343-345, herein incorporated by reference in the entirety. In some embodiments, proteinase K or phenol/chloroform/isoamylalcohol (PCI) purification is used to remove the nuclease agent (e.g., Cas protein) from the reaction mixture. In some embodiments, the nuclease agent (e.g., Cas protein) can be removed from the reaction mixture by silica gel-based column purification.

In certain embodiments the methods disclosed herein assemble a vector with a linear polynucleotide. In other embodiments, the methods disclosed herein assemble at least two vectors, such as two BAC vectors. The term "BAC vector" includes any bacterial artificial chromosome. In specific embodiments, the BAC is modified to contain a region with a nucleotide sequence that overlaps with the nucleotide sequence of region of a linear nucleic acid or another vector, for example, another BAC.

First and second single stranded nucleic acids have overlapping ends when the respective ends are complementary to one another. First and second double stranded nucleic acids have overlapping ends when a 5' end of a strand of the first nucleic acid is complementary to the 3' end of a strand of the second nucleic acid and vice versa. For example, for double stranded overlapping end sequences, the strands of one nucleic acid can have at least 80%, at least 85%, at least 90%, at least 95%, at least 96%, at least 97%, at least 98%, at least 99%, or 100% identity to a corresponding strand of the other nucleic acid. In methods disclosed herein, the 5' end of a strand of a dsDNA molecule to be assembled, shares overlapping end sequences with the 3' end of a strand of the other dsDNA molecule. The term "overlapping end sequences" includes both strands of a dsDNA molecule. Thus, one strand from the overlapping region can hybridize specifically to its complementary strand when the complementary regions of the overlapping sequences are presented in single-stranded overhangs from the 5' and 3' ends of the two polynucleotides to be assembled. In some embodiments, an exonuclease is used to remove nucleotides from the 5' or 3' end to create overhanging end sequences. In some embodiments, the overlapping region of the first and/or second nucleic acid does not exist on 5' or 3' end until after digestion with a Cas protein. That is, the overlapping region can be an internal region that is subsequently converted to an overlapping end sequence following digestion of the nucleic acid(s) containing the internal overlapping region with a Cas protein. The Cas protein can cleave at a target site (e.g., cleavage site) within the overlapping region or outside of the overlapping region.

The length of the overlapping region is preferably of sufficient length such that the region occurs only once within any of the nucleic acids being assembled. In this manner, other polynucleotides are prevented from annealing with the end sequences and the assembly can be specific for the target nucleic acids. The length of the overlapping region can vary from a minimum of about 10 base pairs (bp) to about 300 bp or more. In general, it is preferable that the length of the overlap is less than or equal to about the size of the polynucleotide to be combined, but not less than about 10 bp and not more that about 1000 bp. For the joining of 2 or 3 polynucleotides, about 20-30 bp overlap may be sufficient. For more than 10 fragments, a preferred overlap is about 80 bp to about 300 bp. In one embodiment, the overlapping region is of a length that allows it to be generated readily by synthetic methods, e.g., about 40 bp. In specific embodiments, the length of the overlapping region can be about 20-200 bp. The overlaps can be about 10, 20, 30, 40, 50, 60, 70, 80, 90, 100, 150, 200, 250, 300, 350, 400, 450, 500, 550, 600, 650, 700, 750, 800, 850, 900, 950 or 1,000 bp in length. In some embodiments, the length of the overlapping region is from 20-200 bp. In specific embodiments of the methods disclosed herein at least two polynucleotides can be assembled wherein an overlapping region on at least one of the polynucleotides is generated by contact with a nuclease agent (e.g., a gRNA-Cas complex). For example, endonuclease digestion of a first polynucleotide can create sequences that overlap with the end sequences of a second polynucleotide, wherein the overlapping end sequences are then assembled.

In the methods disclosed herein, the overlapping sequences can be contacted with an exonuclease to expose complementary sequences (e.g., complementary single strand sequences) between the overlapping sequences. The exonuclease digestion is carried out under conditions that are effective to remove ("chew back") a sufficient number of nucleotides to allow for specific annealing of the exposed single-stranded regions of complementarity. In general, a portion of the region of overlap or the entire region of overlap is chewed back, leaving overhangs which comprise a portion of the region of overlap or the entire region of overlap. In some methods, the exonuclease digestion may be carried out by a polymerase in the absence of dNTPs (e.g., T5 DNA polymerase) whereas in other methods, the exonuclease digestion may be carried out by an exonuclease in the presence of dNTPs that lacks polymerase activity (e.g., exonuclease III).

Any of a variety of 5' to 3', double-strand specific exodeoxyribonucleases may be used to chew-back the ends of nucleic acids in the methods disclosed herein. The term "5' exonuclease" is sometimes used herein to refer to a 5' to 3' exodeoxyribonuclease. A "non-processive" exonuclease, as used herein, is an exonuclease that degrades a limited number of (e.g., only a few) nucleotides during each DNA binding event. Digestion with a 5' exonuclease produces 3' single-stranded overhangs in the DNA molecules. Among other properties which are desirable for a 5' exonuclease are that it lacks 3' exonuclease activity, it generates 5' phosphate ends, and it initiates degradation from both 5'-phosphorylated and unphosphorylated ends. It also desirable that the enzyme can initiate digestion from the 5' end of a molecule, whether it is a blunt end, or it has a small 5' or 3' recessed end. Suitable exonucleases will be evident to the skilled worker. These include, e.g., phage T5 exonuclease (phage T5 gene D15 product), phage lambda exonuclease, RecE of Rac prophage, exonuclease VIII from *E. coli*, phage T7 exonuclease (phage T7 gene 6 product), or any of a variety of 5' exonuclease that are involved in homologous recombination reactions. In one embodiment of the invention, the exonuclease is T5 exonuclease or lambda exonuclease. In another embodiment, the exonuclease is T5 exonuclease. In another embodiment, the exonuclease is not phage T7 exonuclease. Methods for preparing and using exonucleases and other enzymes employed in methods of the invention are conventional; and many are available from commercial sources, such as USB Corporation, 26111 Miles Road, Cleveland, Ohio 44128, or New England Biolabs, Inc. (NEB), 240 County Road, Ipswich, Mass. 01938-2723.

Particularly, in embodiments where the region of overlap is very long, it may only be necessary to chew-back a portion of the region (e.g., more than half of the region of overlap), provided that the single-stranded overhangs thus generated are of sufficient length and base content to anneal specifically under the conditions of the reaction. The term "annealing specifically" includes situations wherein a particular pair of single-stranded overhangs will anneal preferentially (or exclusively) to one another, rather than to other single-stranded overhangs (e.g., non-complementary overhangs) which are present in the reaction mixture. By "preferentially" is meant that at least about 95% of the overhangs will anneal to the complementary overhang. A skilled worker can readily determine the optimal length for achieving specific annealing of a sequence of interest under a given set of reaction conditions. Generally, the homologous regions of overlap (the single-stranded overhangs or their complements) contain identical sequences. However, partially identical sequences may be used, provided that the single-stranded overhangs can anneal specifically under the conditions of the reactions.

In certain embodiments, the nuclease agent (e.g., a Cas protein) can create single strand breaks (i.e., "nicks") at the target site without cutting both strands of dsDNA. A "nickase" includes a nuclease agent (e.g., a Cas protein) that create nicks in dsDNA. In this manner, two separate nuclease agents (e.g., Cas proteins) (e.g., nickases) specific for a target site on each strand of dsDNA can create overhanging sequences complementary to overhanging sequences on another nucleic acid, or a separate region on the same nucleic acid. The overhanging ends created by contacting a nucleic acid with two nickases specific for target sites on both strands of dsDNA can be either 5' or 3' overhanging ends. For example, a first nickase can create a single strand break on the first strand of dsDNA, while a second nickase can create a single strand break on the second strand of dsDNA such that overhanging sequences are created. The target sites of each nickase creating the single strand break can be selected such that the overhanging end sequences created are complementary to overhanging end sequences on a second nucleic acid. Accordingly, the complementary overhanging ends of the first and second nucleic acid can be annealed by the methods disclosed herein. In some embodiments, the target site of the nickase on the first strand is different from the target site of the nickase on the second strand. Different target sites on separate strands of dsDNA result in single strand breaks separated by at least 2, 3, 4, 5, 6, 7, 8, 9, 10, 15, 20, 25, 30, 40, 50, 75, 100, 250, 500, or 1,000 base pairs.

In certain embodiments, the second nucleic acid is also contacted with a first nickase that creates a nick at a first target site on the second nucleic acid and a nickase that creates a nick at a second target site on the second nucleic acid molecule. The overhanging end sequences created by the nicks at two different sites on the second nucleic acid can be complementary to the overhanging end sequences created by nicks at two different sites on the first nucleic acid so that the complementary overhanging end sequences anneal.

In some embodiments, the nucleic acid sequence of a gene of interest spans across two or more BACs. In such cases, using the methods provided herein, specifically designed nuclease agents can cut the two or more BACs at the desired locations and the resulting nucleic acid fragments joined together to form the sequence of the gene of interest.

In some embodiments, the overhanging ends created by nicks at different target sites on both strands of a first nucleic acid are not complementary to the overhanging ends created by nicks at different target sites on both strands of a second nucleic acid. In other embodiments, the nucleic acids to be assembled do not have complementary ends such that a separate nucleic acid is necessary to assemble the non-complementary ends. A joiner oligo can be used to join non-complementary ends of two nucleic acids. A "joiner oligo" includes complementary arms including a polynucleotide or nucleic acid having a complementary sequence to the ends of a different polynucleotide or nucleic acid. In some embodiments, a joiner oligo has an arm complementary to a first nucleic acid on the 5' end, a central portion (spacer), and an arm complementary to a second nucleic acid on the 3' end. Thus, nucleic acids having non-complementary end sequences to each other can be assembled by annealing each nucleic acid to the same joiner oligo following an exonuclease treatment. In specific embodiments, the joiner oligo has a first arm complementary to the 5' or 3' end sequence of a first digested nucleic acid and a second arm complementary to the 5' or 3' sequence of a second digested nucleic acid. The joiner oligo can join non-complimentary end sequences that are blunt or have 5' or 3' overhanging sequence.

The length of the complementary arm sequences of the joiner oligo should be sufficient to anneal to the nucleic acids to be assembled following exonuclease treatment. For example, the length of the complementary arm sequences of the joiner oligo can be at least about 10, 20, 30, 35, 40, 45, 50, 55, 60, 65, 70, 75, 80, 90, 100, 110, 120, 130, 140, 150 bp or more. In specific embodiments, the complementary arm is 15-120 bp, 20-100 bp, 30-90 bp, 30-60 bp, or 20-80 bp. In one specific embodiment, the length of the complementary arm sequences of the joiner oligo is 40 bp. Each complementary arm of a joiner oligo can be of different lengths. The spacer of the joiner oligo, between the end sequences complementary to the nucleic acids to be assembled, can be at least about 20 bp, 30 bp, 35 bp, 40 bp, 45 bp, 50 bp, 55 bp, 60 bp, 65 bp, 70 bp, 75 bp, 80 bp, 90 bp, 100 bp, 250 bp, 500 bp, 750 bp, 1000 bp, 2000 bp, 3000 bp, 4000 bp, 5000 bp, 8000 bp, 10 kb, 15 kb, 20 kb, or more. For example, the spacer of a joiner oligo can include a BAC vector or LTVEC. In some embodiments, the spacer of the joiner oligo can be designed to have sequences specific for detection or sequences suitable for PCR in order to confirm successful assembly. In some embodiments, the spacer of the joiner oligo can be designed to introduce one or more restriction enzyme sites. In some embodiments, the space of the joiner oligo can be designed to introduce a drug resistance gene or a reporter gene. In other embodiments, the spacer can contain at least 20 bp from an end portion of a nucleic acid to be assembled in order to seamlessly assemble the nucleic acids. For example, for seamless assembly the spacer can be about 45 bp.

In some embodiments, the molar ratio of the nucleic acid to joiner oligo(s) can be from about 1:1 to about 1:200. In some embodiments, the molar ratio of the nucleic acid to joiner oligo(s) is about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, 1:100, 1:120, 1:140, 1:160, 1:180, or 1:200. In specific embodiments, the molar ratio of the nucleic acid to joiner oligo(s) can be from about 1:6 to about 1:20. In one embodiment, the molar ratio is about 1:6. In another embodiment, the molar ratio is about 1:20.

In specific embodiments, a joiner oligo is used to seamlessly assemble at least two nucleic acids. "Seamless" assembly refers to assembly of two nucleic acids wherein no intervening nucleic acid bases are present between the adjacent ends of the nucleic acids to be assembled. For example, seamlessly assembled nucleic acids have no nucleic acid bases present that are not a part of the nucleic acids to be assembled. In order to seamlessly assemble two nucleic acids, the spacer of a joiner oligo should include nucleic acid sequence identical to an end portion of either the first or second nucleic acid to be assembled. This end portion should be removed from the nucleic acid prior to assembling with the joiner oligo. For example, the end portion can be cleaved by a nuclease agent (e.g., a gRNA-Cas complex) at least 20 bp from the end of the nucleic acid, such at least 40 bp or at least 45 bp from the end of the nucleic acid. Alternatively, the end portion can be cleaved by a nuclease agent (e.g., a gRNA-Cas complex) at least 2, at least 4, at least 6, at least 8, at least 10, at least 12, at least 15, at least 20, at least 25, at least 30, at least 35, at least 37, at least 40, at least 42, at least 45, at least 48, at least 50, at least 55, at least 60, at least 65, at least 70, at least 80, at least 100, at least 110, at least 120, at least 130, at least 140, at least 150 bp from the end of the nucleic acid to be assembled.

Figure 5:
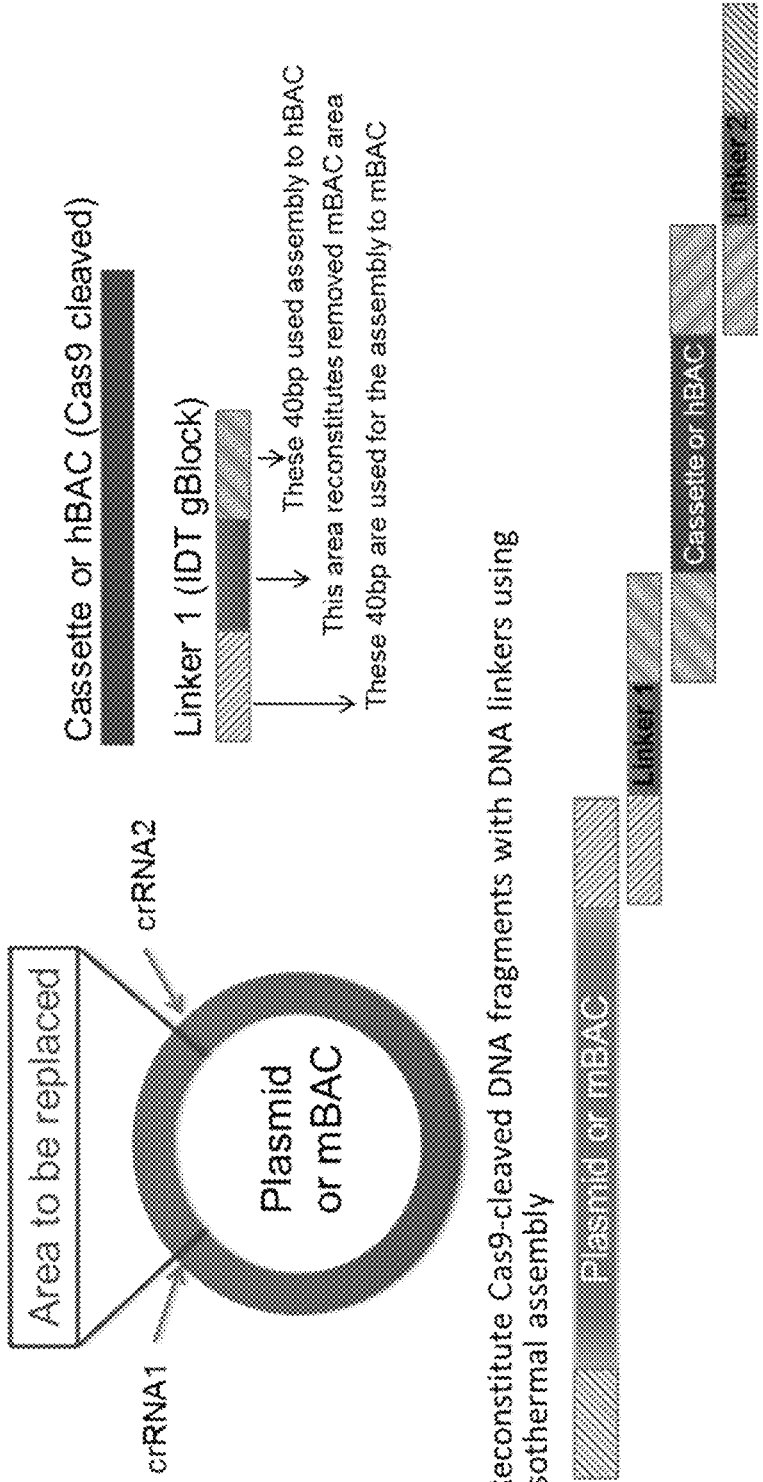
FIG. 5 shows the construction of a large targeting vector (LTVEC) using CRISPR/Cas9 system and isothermal assembly. DNA fragments cleaved with CRISPR/Cas9 were seamlessly assembled using one or more joiner oligos and isothermal assembly.

In one embodiment, the joiner oligo can comprise from the 5' end to the 3' end: about a 15-120 bp overlap to the 5' nucleic acid, about 20-50 bp of a 3' end region of the 5' nucleic acid, and about a 15-120 bp overlap to the 3' nucleic acid. In one embodiment, the joiner oligo can comprise from the 5' end to the 3' end: about a 15-120 bp overlap to the 5' nucleic acid, about 20-50 bp of a 5' end region of the 3' nucleic acid, and about a 15-120 bp overlap to the 3' nucleic acid. Thus, when the joiner oligo is assembled to the first and second nucleic acid, the spacer from the joiner oligo reconstitutes the section removed from the nucleic acid prior to assembly. See, FIG. 5 and FIG. 6. The term "reconstitutes" includes replacement of the end portion of the nucleic acid that was cleaved in order to provide a complete assembled nucleic acid when assembled to the joiner oligo. For example, reconstituting the cleaved nucleic acid replaces the cleaved portion of the nucleic acid with a nucleic acid included in the spacer of the joiner oligo having the identical sequence to that of the cleaved portion.

The joiner oligo can be assembled to a first and second nucleic acid molecule simultaneously or sequentially. When assembled simultaneously, the joiner oligo can be contacted with a first and second nucleic acid in the same reaction mixture such that the resulting assembled nucleic acid comprises the first nucleic acid, joiner oligo, and second nucleic acid. When assembled sequentially, the joiner oligo is contacted with the first nucleic acid in an assembly reaction that produces an assembled nucleic acid comprising the first nucleic acid assembled to the joiner oligo, but not the second nucleic acid. Such an assembled nucleic acid can then be contacted with the second nucleic acid in a separate assembly reaction that produces an assembled nucleic acid comprising the first nucleic acid, joiner oligo, and second nucleic acid. In other embodiments, the joiner oligo is contacted with the second nucleic acid in an assembly reaction that produces an assembled nucleic acid comprising the second nucleic acid assembled to the joiner oligo, but not the first nucleic acid. Such an assembled nucleic acid can then be contacted with the first nucleic acid in separate assembly reaction that produces an assembled nucleic acid comprising the first nucleic acid, joiner oligo, and second nucleic acid.

Any number of joiner oligos can be used in the methods herein to assemble nucleic acid molecules. For example, 1 joiner oligo can be used to assemble 2 nucleic acid molecules, 2 joiner oligos can be used to assemble 3 nucleic acid molecules, 3 joiner oligos can be used to assemble 4 nucleic acid molecules, 4 joiner oligos can be used to assemble 5 nucleic acid molecules, or 5 joiner oligos can be used to assemble 6 nucleic acid molecules. The number of joiner oligos can be 1, 2, 3, 4, 5, 6, 7, 8, 9, 10 or more depending on the number of nucleic acid molecules to be assembled.

In some embodiments, the joiner oligo comprises a gBlock DNA. A "gBlock" is a linear double stranded DNA fragment. The gBlock can be from about 50 bp to about 2000 bp. The gBlock can be from about 50 bp to about 100 bp, from about 100 bp to about 200 bp, from about 200 bp to about 300 bp, from about 300 bp to about 400 bp, from about 400 bp to about 500 bp, from about 500 bp to about 600 bp, from about 600 bp to about 800 bp, from about 800 bp to about 1000 bp, from about 1000 bp to about 1250 bp, from about 1250 bp to about 1500 bp, from about 1500 bp to about 1750 bp, or from about 1750 bp to about 2000 bp.

Assembly of two or more nucleic acids with a gBlock can be screened, for example, by PCR assays described elsewhere herein (e.g., Example 10). In some cases, the gBlock does not comprise a selection cassette. Such a method allows for rapid joining of two or more nucleic acid molecules that can be screened by a simple PCR assay. The gBlock can comprise any nucleic acid sequence of interest. In some cases, the gBlock can comprise a target site for a nuclease agent or a target site for any of the various meganucleases or restriction enzymes provided herein. In other embodiments, a gBlock can comprise a selection cassette. In some embodiments, the gBlock comprises a DNA sequence of interest. In one embodiment, the gBlock comprises a human DNA sequence.

The nucleic acids to be assembled or any of the various joiner oligos can also comprise a selection cassette or a reporter gene. The selection cassette can comprise a nucleic acid sequence encoding a selection marker, wherein the nucleic acid sequence is operably linked to a promoter. The promoter can be active in a prokaryotic cell of interest and/or active in a eukaryotic cell of interest. Such promoters can be an inducible promoter, a promoter that is endogenous to the reporter gene or the cell, a promoter that is heterologous to the reporter gene or to the cell, a cell-specific promoter, a tissue-specific promoter or a developmental stage-specific promoter. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof. The selection marker of the targeting vector can be flanked by the upstream and downstream homology arms or found either 5' or 3' to the homology arms.

In one embodiment, the nucleic acids to be assembled or any of the various joiner oligos comprise a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. Such reporter genes can be operably linked to a promoter active in the cell. Such promoters can be an inducible promoter, a promoter that is endogenous to the report gene or the cell, a promoter that is heterologous to the reporter gene or to the cell, a cell-specific promoter, a tissue-specific promoter manner or a developmental stage-specific promoter.

Following the annealing of single stranded DNA (e.g., overhangs produced by the action of exonuclease when the DNA molecules to be joined are dsDNA or overhangs produced by creating nicks at different target sites on each strand), the single-stranded gaps left by the exonuclease are filled in with a suitable, non-strand-displacing, DNA polymerase and the nicks thus formed a sealed with a ligase. A "non-strand-displacing DNA polymerase," as used herein, is a DNA polymerase that terminates synthesis of DNA when it encounters DNA strands which lie in its path as it proceeds to copy a dsDNA molecule, or that degrades the encountered DNA strands as it proceeds while concurrently filling in the gap thus created, thereby generating a "moving nick" (nick translation).

In some embodiments, overlapping end sequences have sufficient complementarity between the overlapping regions to anneal the single-stranded complementary ends of each polynucleotide. Following annealing of a single strand of a first polynucleotide to the complementary strand of a second polynucleotide, the 3' end of the first polynucleotide can be extended based on the template of the second polynucleotide strand and the 3' end of the second polynucleotide strand can be extended based on the template of the first polynucleotide strand. By extending the complementary 3' end of each polynucleotide, the polynucleotides can be assembled. Following assembly, nicks between the extended 3' end of a strand from one fragment and adjacent 5' end of a strand from the other fragment can be sealed by ligation. More specifically, the hydroxyl group of the extended 3' end of the first polynucleotide to the phosphate group of the 5' end of the second polynucleotide and ligating the hydroxyl group of the extended 3' end of the second polynucleotide to the phosphate group of the 5' end of the first polynucleotide.

The ligation reaction can be performed by any of a variety of suitable thermostable DNA ligases. Among the suitable ligases are, for example, Taq ligase, Ampligase Thermostable DNA ligase (Epicentre Biotechnologies), the Thermostable ligases disclosed in U.S. Pat. No. 6,576,453, Thermostable Tfi DNA ligase from Bioneer, Inc., A suitable amount of a crowding agent, such as PEG, in the reaction mixture allows for, enhances, or facilitates molecular crowding. Without wishing to be bound by any particular mechanism, it is suggested that a crowding agent, which allows for molecular crowding and binds to and ties up water in a solution, allowing components of the solution to come into closer contact with one another. For example, DNA molecules to be recombined can come into closer proximity; which facilitates the annealing of the single-stranded overhangs. Also, it is suggested that enzymes can come into closer contact with their DNA substrates and can be stabilized by the removal of water molecules. A variety of suitable crowding agents will be evident to the skilled worker. These include a variety of well-known macromolecules, such as polymers, e.g., polyethylene glycol (PEG); Ficoll, such as Ficoll 70; dextran, such as dextran 70; or the like. Much of the discussion in this application is directed to PEG. However, the discussion is meant also to apply to other suitable crowding agents. A skilled worker will recognize how to implement routine changes in the method in order to accommodate the use of other crowding agents.

A suitable amount of a crowding agent, such as PEG, in the reaction mixture allows for, enhances, or facilitates molecular crowding. For example, crowding agents can help DNA molecules to be recombined can come into closer proximity; this thus facilitates the annealing of the single-stranded overhangs. Also, it is suggested that enzymes can come into closer contact with their DNA substrates and can be stabilized by the removal of water molecules. A variety of suitable crowding agents will be evident to the skilled worker. These include a variety of well-known macromolecules, such as polymers, e.g., polyethylene glycol (PEG); Ficoll, such as Ficoll 70; dextran, such as dextran 70; or the like. In general, when PEG is used, a concentration of about 5% (weight/volume) is optimal. However, the amount of PEG can range, e.g., from about 3 to about 7%. Any suitable size of PEG can be used, e.g., ranging from about PEG-200 (e.g., PEG-4000, PEG-6000, or PEG-8000) to about PEG-20,000, or even higher. In the Examples herein, PEG-8000 was used. The crowding agent can, in addition to enhancing the annealing reaction, enhance ligation.

Reaction components (such as salts, buffers, a suitable energy source (such as ATP or NAD), pH of the reaction mixture, etc.) that are present in an assembly reaction mixture may not be optimal for the individual enzymes (exonuclease, polymerase, and ligase); rather, they serve as a compromise that is effective for the entire set of reactions. For example, one suitable buffer system identified by the inventors, sometimes referred to herein as ISO (ISOthermal) Buffer typically comprises 0.1 M Tris-Cl pH 7.5; 10 mM MgCl$_2$, 0.2 mM each of dGTP, dATP, dTTP and dCTP, 10 mM DTT, 5% PEG-8000, and 1 mM NAD.

In the methods disclosed herein, at least two nucleic acids are contacted with a Cas protein and other enzymes under conditions effective to assemble the nucleic acids to form an assembled double-stranded DNA molecule in which a single copy of the overlapping region is retained. The described methods can be used to join any DNA molecules of interest, including DNAs which are naturally occurring, cloned DNA molecules, synthetically generated DNAs, etc. The joined DNA molecules may, if desired, be cloned into a vector (e.g., using a method of the invention). In some embodiments, the nucleic acids to be assembled are codon optimized for introduction and expression in a cell of interest (e.g., a rodent cell, mouse cell, rat cell, human cell, mammalian cell, microbial cell, yeast cell, etc. . . . ).

DNA molecules of any length can be joined by methods disclosed herein. For example, nucleic acids having about 100 bp to about 750 or 1,000, or more, can be joined. The number of nucleic acids that may be assembled, in one or several assembly stages according to the methods described therein, may be at least about 2, 3, 4, 6, 8, 10, 15, 20, 25, 50, 100, 200, 500, 1,000, 5,000, or 10,000 DNA molecules, for example in the range of about 2 to about 30 nucleic acids. The number of assembly stages may be about 2, 4, 6, 8, 10, or more. The number of molecules assembled in a single stage may be in the range of about 2 to about 10 molecules. The methods of the invention may be used to join together DNA molecules or cassettes each of which has a starting size of at least or no greater than about 40 bp, 60 bp, 80 bp, 100 bp, 500 bp, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger. The assembled end products may be at least about 500 bp, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of 30 kb to 1 Mb.

In some embodiments, the assembled nucleic acids form a circle and/or become ligated into a vector to form a circle. The lower size limit for a dsDNA to circularize is about 200 base pairs. Therefore, the total length of the joined fragments (including, in some cases, the length of the vector) is at least about 200 bp in length. There is no practical upper size limit, and joined DNAs of a few hundred kilobase pairs, or larger, can be generated by the methods disclosed herein. The joined nucleic acids can take the form of either a circle or a linear molecule.

The methods described herein can be used to assemble a linear fragment with another linear fragment, a linear fragment with a circular nucleic acid molecule, a circular nucleic acid molecule with another circular nucleic acid molecule, or any combination of linear and circular nucleic acids. A "vector" includes any circular nucleic acid molecule. In certain embodiments, the vector assembled by the methods disclosed herein is a bacterial artificial chromosome (BAC). The vector (e.g., the BAC) can include a human DNA, a rodent DNA, a synthetic DNA, or any combination thereof. For example, the BAC can comprise a human polynucleotide sequence. When joining a mixture of DNA molecules, it is preferable that the DNAs be present in approximately equimolar amounts.

The nucleic acid used for assembly by the methods disclosed herein can be a large targeting vector. The term "large targeting vector" or "LTVEC" includes vectors that comprise homology arms that correspond to and are derived from nucleic acid sequences used for homologous targeting in cells and/or comprise insert nucleic acids comprising nucleic acid sequences intended to perform homologous recombination targeting in cells. For example, the LTVEC make possible the modification of large loci that cannot be accommodated by traditional plasmid-based targeting vectors because of their size limitations. In specific embodiments, the homology arms and/or the insert nucleic acid of the LTVEC comprises genomic sequence of a eukaryotic cell. The size of the LTVEC is too large to enable screening of targeting events by conventional assays, e.g., southern blotting and long-range (e.g., 1 kb-5 kb) PCR. Examples of the LTVEC, include, but are not limited to, vectors derived from a bacterial artificial chromosome (BAC), a human artificial chromosome or a yeast artificial chromosome (YAC). Non-limiting examples of LTVECs and methods for making them are described, e.g., in U.S. Pat. Nos. 6,586,251, 6,596,541, 7,105,348, and WO 2002/036789 (PCT/US01/45375), and US 2013/0137101, each of which is herein incorporated by reference.

In some embodiments, cassettes can be inserted into vectors that can later be removed. Various forms of cassettes can be constructed to allow for deletion in specific cell or tissue types, at specific developmental stages, or upon induction. Such cassettes can employ a recombinase system in which the cassette is flanked on both sides by recombinase recognition sites and can be removed using a recombinase expressed in the desired cell type, expressed at the desired developmental stage, or expressed or activated upon induction. Such cassettes can further be constructed to include an array of pairs of different recombinase recognition sites that are placed such that null, conditional, or combination conditional/null alleles can be generated, as described in US 2011/0104799, which is incorporated by reference in its entirety. Regulation of recombinase genes can be controlled in various ways, such as by operably linking a recombinase gene to a cell-specific, tissue-specific, or developmentally regulated promoter (or other regulatory element), or by operably linking a recombinase gene to a 3'-UTR that comprises a recognition site for an miRNA that is transcribed only in particular cell types, tissue types, or developmental stages. A recombinase can also be regulated, for example, by employing a fusion protein placing the recombinase under the control of an effector or metabolite (e.g., CreER$^{T2}$, whose activity is positively controlled by tamoxifen), or by placing the recombinase gene under the control of an inducible promoter (e.g., one whose activity is controlled by doxycycline and TetR or TetR variants). Examples of various forms of cassettes and means of regulating recombinase genes are provided, for example, in U.S. Pat. Nos. 8,518,392; 8,354,389; and 8,697,851, each of which is incorporated by reference in its entirety.

The vectors used for assembling as disclosed herein (e.g., LTVEC) can be of any length, including, but not limited to, from about 20 kb to about 400 kb, from about 20 kb to about 30 kb, from about 30 kb to 40 kb, from about 40 kb to about 50 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb, from about 200 kb to about 300 kb, from about 300 kb to about 350 kb, from about 350 kb to about 400 kb, from about 350 kb to about 550 kb. In one embodiment, the LTVEC is about 100 kb.

The methods provided herein for assembling nucleic acids can be designed so as to allow for a deletion from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In other instances, the methods provided herein are designed so as to allow for an insertion of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb. In one embodiment, the insert polynucleotide is about 130 kb or about 155 kb.

Linear nucleic acids can be assembled with each other or to vectors by the methods disclosed herein. The linear molecule can be a vector that has been digested by an endonuclease (e.g., Cas protein) or any synthetic, artificial, or naturally occurring linear nucleic acid. In certain embodiments, the linear nucleic acid is created such that the end sequences overlap with a region of another nucleic acid. The overlapping end sequences of a linear nucleic acid can be introduced by any method known in the art for generating customized nucleic acid sequences. For example, the end sequences can be a portion of a synthetically produced molecule, can be introduced by PCR, or can be introduced by traditional cloning techniques.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average

Example 1: BAC Digest with CAS9 Followed by Assembly with a Selection Cassette An artificial crRNA and an artificial tracrRNA were designed to target specific sequences in the MAID 6177 (116 kb LTVEC) for assembly with a 3 kb PCR product (UB-HYG). The PCR product contained 50 bp overlaps with the vector. First dissolve crRNAs and tracrRNA to 100 uM in Duplex Buffer (30 mM HEPES, pH 7.5, 100 mM Potassium Acetate). In order to anneal the RNAs, add 10 ul of 100 uM crRNA and 10 ul of 100 uM tracrRNA to 80 ul of annealing buffer. Heat RNAs in a 90° C. temp block then remove block from heater and cool on bench. Final concentration of RNA is about 10 uM.

In order to digest the BAC, clean maxiprep BAC DNA is used and the BAC digested according to the following mixture.

| | 1X |
|---|---|
| BAC DNA (500 ng) | X ul |
| BSA (100x) | 0.5 ul |
| RNA | 2 ul (1 ul of each tracr:crRNA hybrid) |
| Cas9 (4.5 mg/ml) | 1 ul |
| 10x Buffer | 1.5 ul |
| H$_2$O | to 15 ul |

Digest for 1 hour at 37° then de-salt for 30 min. The final reaction buffer contains: 20 mM Tris 7.5; 100-150 mM NaCl; 10 mM MgCl2; 1 mM DTT; 0.1 mM EDTA; 100 ug/ml BSA; for a final volume of 15 ul.

In order to assemble the BAC and insert, digest a plasmid or perform PCR to create an insert. For PCR reactions, run a small aliquot on a gel and look for a single product, if the product has a single band then do PCR cleanup instead of gel extraction. A 1:1-1:6 molar ratio for the BAC:Insert is desired. Usually, 50 ng of the purified insert will work. The following reaction mix can be used:

| BAC Digest | 4 ul |
|---|---|
| Insert | 1 ul |
| Assembly Mix | 15 ul |

Add the DNA and Mix on ice or directly in a PCR machine at 50° C. Incubate at 50° C. for 1 hour. Add 0.5 uL of Proteinase K (20 mg/ml) and incubate at 50° C. for 1 hour. Desalt for 30 min and electroporate 8 ul of the reaction into DH10B cells. 10 ul of the BAC Digest can be run on a pulse-field gel to check digestion efficiency. Use RNase-free water and buffers.

The assembly reaction is carried out as follows: Iso-Thermal Buffer: 3 mL 1M Tris-HCL (pH 7.5); 150 ul 2M MgCl$_2$; 60 ul 100 mM each: dGTP, dATP, dTTP, dCTP; 300 ul 1M DTT; 1.5 g PEG 8000; 300 ul 100 mM NAD. The iso-thermal Buffer is stored in 320 ul aliquots at −20° C. The Master Mix is prepared as follows: 320 ul iso-thermal Buffer; 0.64 ul T5 exonuclease (stock conc=10 U/ul); 20 ul Phusion DNA polymerase (stock conc=2 U/ul); 160 ul Taq DNA Ligase (stock conc=40 U/ul); 699.36 ul H$_2$O; mix together, and aliquot at 15 ul or 30 ul and store −20° C. Use 15 ul master mix (MM) in a total volume of 20 ul reaction.

The tracr RNA sequence used in the example is: CAAAACAGCAUAGCAAGUUAAAAUAAGGCUAGU-CCGUUAUC (SEQ ID NO: 9). This CRISPR RNA (crRNA) contains: (1) about 20 nucleotides of RNA complementary to a target sequence and (2) a tail sequence (GUUUUAGAGCUAUGCUGUUUUG (SEQ ID NO: 10)) that will anneal to the tracrRNA.

Figure 1:
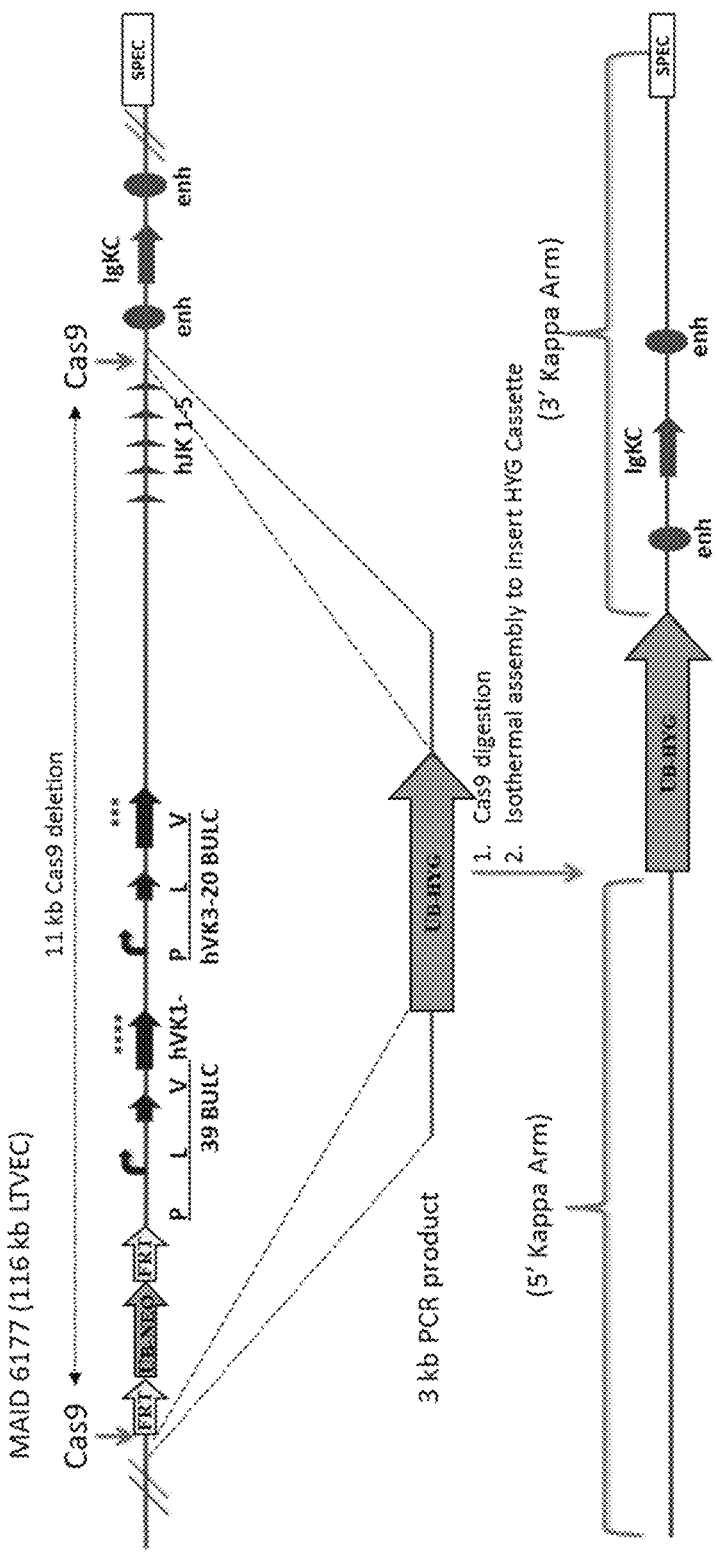
FIG. 1 shows assembly of a BAC to a PCR product having overlaps designed to be specific for the BAC. 50 bp overlaps were added to the HYG cassette by PCR.

These steps are outlined in FIG. 1.

Example 2: Sewing Together Two Overlapping BACs: Humanized HLA-DQ+Humanized HLA-DR in Mouse MHC II Locus (H2-A/H2-E)

An artificial crRNA and an artificial tracrRNA were designed to target specific sequences in the humanized HLA-DQ BAC for assembly with a humanized HLA-DR BAC. The vectors contained ~70 bp overlaps with each other created by Cas9 cleavage at two sites on each vector (See, FIG. 2). Dissolve crRNAs and tracrRNA to 100 uM in Hybe Buffer. To anneal the RNAs, add 10 ul of 100 uM crRNA and 10 ul of 100 uM tracrRNA to 80 ul of Annealing buffer. Place RNAs in a 90° C. heat block then remove block from heater and cool on bench. Final concentration of RNA is about 10 uM.

In order to digest the BAC, clean maxiprep BAC DNA can be used. Each BAC can be digested individually according to the following mixture:

| BAC DNA 2.5 ug | X ul |
|---|---|
| BSA (100x) | 0.5 ul |
| RNA | 4 ul (2 ul of each tracr:crRNA hybrid) |
| Cas9 (4.5 mg/ml) | 1 ul |
| 10x Buffer | 5 ul |
| H$_2$O | to 50 ul |

The BAC vectors should be digested at 37° C. for 1 hour and then heat inactivated for 20 min at 65° C. Desalt for 30 min. The digested DNA was purified via phenol/chloroform/isoamylalcohol (PCI) extraction and then resuspended in 35 ul TE buffer.

In order to assemble the vectors, use 2.5 uL of the BACs for the assembly reaction as follows:

| Digested BACs | 5 ul (total) |
|---|---|
| Assembly MIX | 15 ul |

Add the DNA and Mix on ice or directly in a PCR machine at 50° C. Incubate at 50° C. for 1 hour. Desalt for 30 min and electroporate 8 ul of the assembled DNA into DH10B cells. Use RNase-free water and buffers.

The tracr RNA sequence used in the example is: CAAAACAGCAUAGCAAGUUAAAAUAAGGCUAGU-CCGUUAUC (SEQ ID NO: 9). This CRISPR RNA (crRNA) contains: (1) about 20 nucleotides of RNA complementary to a target sequence and (2) a tail sequence (GUUUUAGAGCUAUGCUGUUUUG (SEQ ID NO: 10)) that will anneal to the tracrRNA.

Figure 2:
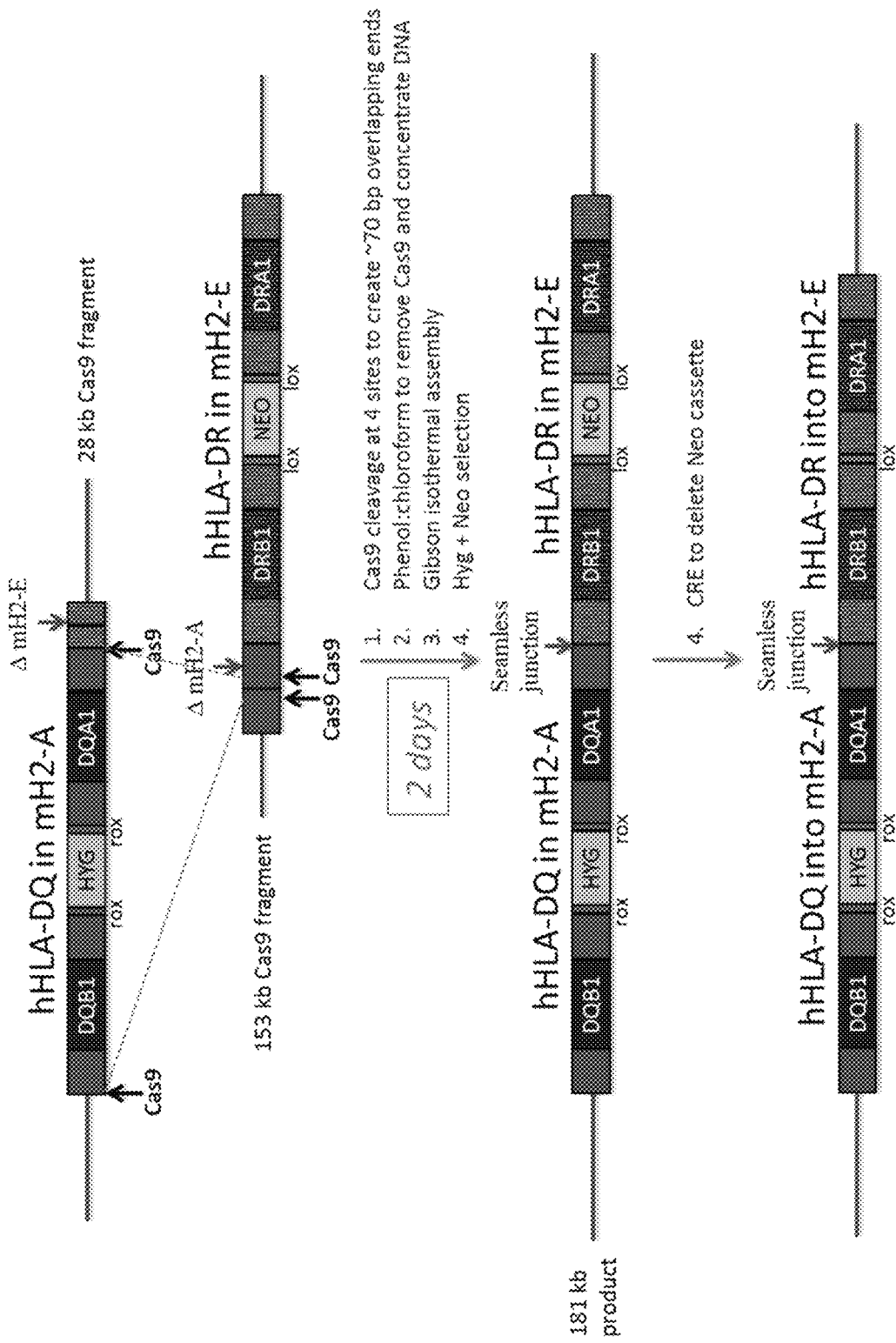
FIG. 2 shows assembly of two BACs having overlapping sequences using two Cas9 target sites on each BAC. The process of assembly using the method disclosed herein took 2 days.

These steps are outlined in FIG. 2.

Example 3: Assembling of 2 Cas9-Cleaved Fragments from 2 Different Plasmids Using Linkers In order to construct a targeting vector, pMJ8502x was cleaved with 2 identical crRNAs to drop out 400 bp fragment and 2283 bp Amp backbone. (FIG. 7). Qiagen columns were used to purify the entire reaction. R6KZenUbiNeo was then cleaved with 2 different crRNAs to separate into Neo resistance (1086 bp) and backbone (5390 bp). Qiagen columns were used purify the entire reaction. (FIG. 7). Cleavage Reaction: 1170 ng DNA, 30 ul Buffer, 4 ul annealed RNA (@100 uM), 1.7 ul Cas9 (@0.89 ng/ul), H$_2$O to 60 ul. The mixture was incubated at 37° C. for 1 hour and purified on a Qiagen column before eluting in 30 ul elution buffer.

The cleaved fragments were then assembled with two linkers to result in a seamless assembly according to the following reaction mixture: 0.5 ul linker1 (5 ng), 0.5 ul linker2 (5 ng), 2 ul Neo cleavage (~60 ng), 2 ul Amp cleavage (~60 ng), 15 ul Assembly Master Mix. The mixture was incubated at 50° C. for 1 hour, and the reaction was dialyzed against H$_2$O. 10 ul of the reaction was electroporated into electrocompetent Pir cells before plating on Carb/Kan plates. PCR across junction showed 6/8 selected colonies were correct and was confirmed by sequencing.

Example 4: Replacement of a Portion of a BAC with a Cassette Using Linkers

In order to construct a knock out mouse targeting vector, 40 kb of a BAC targeting vector was replaced with a selection cassette flanked by recombination recognition sites. (FIG. 8) 2 linkers were designed to delete a region of interest from mBAC and to insert the selection cassette, one for 5' and one for 3'. The linkers had 40 bp overlap to mBAC and 40 bp overlap to a selection cassette. First, 39.5 kb of the 206 kb targeting vector (mBAC) was cleaved according to the following reaction: 500 ul reaction (bring up with H$_2$O): add 1 ul Cas9 (@0.89 ug/ul), 2 ul each RNA duplex (@50 uM), 250 ul buffer, 220 ul (12.5 ng) BAC maxi prep, and incubated at 37° C. for 1 hour. The digested DNA was purified via phenol/chloroform/isoamylalcohol (PCI) extraction and then resuspended in 55 ul TE buffer. After PCI cleanup of the mBAC cleavage, assembly was done at 50° C. for 1 hr, and 10 ul of the reaction was electroporated into DH10B cells. (FIG. 9). Sequencing across junctions confirmed correct assembly. (FIG. 10). Linker 1 (joiner oligo 1) is seamless from mBAC sequence to Cassette sequence (SEQ ID NO: 12). Linker 2 (joiner oligo 2) is seamless from Cassette sequence to mBAC sequence (SEQ ID NO: 13).

Example 5: Assembling Two BAC Vectors Using Linkers (Joiner Oligos)

Stitching of 2 mBACs by Cas9/isothermal assembly was utilized to make a targeting vector that contains homology arms to a mouse genomic region and restriction sites for inserting a human gene by BAC ligation. This targeting vector was used in a BAC ligation to make a humanized targeting vector. The mBAC was cleaved according to the following reaction: 12.5 ug DNA, 2 ul each annealed RNA (@50 uM), 10 ul Cas9 (@0.89 ug/ul), 250 ul buffer, H$_2$O to 500 ul. The mixture was incubated at 37° C. for one hour; cleaned up by phenol/chloroform/isoamylalcohol (PCI) extraction; and resuspended in 20 ul TE. The two mouse BACs were then assembled together with linkers (FIG. 11) according to the following reaction: 6 ul (2 ug) bMQ-208A16 cleavage, 5.6 ul (2 ug) bMQ-50F19 cleavage, 0.25 ul each linker (@50 uM), 4.3 ul (100 ng) selection cassette (Ubi-Hyg) cassette, 12 ul high concentration assembly master mix, 11.35 ul H$_2$O. The reaction mixture was incubated at 50° C. for 1 hour and dialyzed against H$_2$O at 30° C. 10 ul or 30 ul of the dialyzed reaction was used to transform DH10B cells. Sanger sequencing confirmed all junctions. Illumina Sequencing reconfirmed all junctions (FIG. 12 and SEQ ID NO: 17). Linker 1 is seamless from mBAC to Cassette (SEQ ID NO: 14). Linker 2 is not seamless from cassette to mBAC. It incorporates a human spacer sequence as per the project design. Linker 3 is not seamless from mB2 to mB3. It incorporates a unique sequence that was used for PCR verification. This area was removed when linearized for ES electroporation (SEQ ID NO: 15).

FIG. 13 illustrates an example of using 4 joiner oligos (linkers) to insert large human gene fragments onto an mBAC using four linkers and isothermal assembly.

Example 6: Reagents and Reactions Mixtures for Cleavage and Assembly

Crispr RNA (crRNA) (ordered as ssRNA) contains: (1) 20 nucleotides of RNA that is complementary to a target area to cleave; (2) and a tail that will anneal to the tracr RNA: <20 nt crisprRNA>GUUUUAGAGCUAUGCUGUUUUG (SEQ ID NO: 10).

Tracr RNA (ordered as ssRNA): GUUGGAACCAUUCAAAACAGCAUAGCAAGUUAAAAUAAGGCUAGUCCGUUAUCA ACUUGAAAAAGUGGCACCGAGUCGGUGCUUUUUUU (SEQ ID NO: 11).

All RNA is resuspended to 100 uM in H$_2$O. 2.5 ul of each crRNA and tracrRNA is combined with 5 ul of annealing buffer (final concentrations: 10 mM Tris pH 7.5-8.0, 50 mM NaCl, 1 mM EDTA). The mixture is then incubated at 95° C. for 5 minutes and slowly cooled to room temperature over 1 hour. Cas9 2x cleavage buffer contains 40 mM HEPES pH7.5 (Final=20 mM); 300 mM KCl (Final=150 mM); 1 mM DTT (Final=0.5 mM); 0.2 mM EDTA (Final=0.1 mM); 20 mM MgCl2 (Final=10 mM).

Large Scale Cas9 Cleavage Reaction: Add in order at room temperature: H$_2$O to 500 ul, 250 ul 2x cleavage buffer, 12.5 ug DNA, 2 ul of each RNA (50 uM concentration), 10 ul Cas9 (0.89 mg/ml concentration), and incubate at 37° C. for 1 hour.

This reaction can be scaled as needed, for example: H$_2$O to 50 ul, 25 ul Buffer, 125 ng DNA, 2 ul each RNA (5 uM concentration), 1 ul Cas9 (0.89 mg/ml concentration), and incubate at 37° C. for 1 hour.

The assembly reaction is carried out as follows: Iso-Thermal Buffer: 3 mL 1M Tris-HCL (pH 7.5); 150 ul 2M MgCl$_2$; 60 ul 100 mM each: dGTP, dATP, dTTP, dCTP; 300 ul 1M DTT; 1.5 g PEG 8000; 300 ul 100 mM NAD. The iso-thermal Buffer is stored in 320 ul aliquots at −20° C. The Master Mix is prepared as follows: 320 ul iso-thermal Buffer; 0.64 ul T5 exonuclease (stock conc=10 U/ul); 20 ul Phusion DNA polymerase (stock conc=2 U/ul); 160 ul Taq DNA Ligase (stock conc=40 U/ul); 699.36 ul H$_2$O; mix together, and aliquot at 15 ul or 30 ul and store −20° C. Use 15 ul master mix (MM) in a total volume of 20 ul reaction.

Alternatively, a high concentration master mix (GA MM HC) can be made as follows: 320 ul iso-thermal buffer; 0.64 ul T5 exonuclease (stock conc=10 U/ul); 20 ul Phusion DNA polymerase (stock conc=2 U/ul); 160 ul Taq DNA Ligase (stock conc=40 U/ul); mix together and aliquot at 6 ul or 12 ul and store −20° C. Use 6 ul of the master mix in a total volume of 20 ul reaction.

For all assembly reactions, the concentration of DNA should be determined (e.g., by Nano Drop) and a 1:6 molar ratio (vector to insert(s)) is used. For standard concentration, 15 ul of the assembly master mix is used. DNA and water are added to a final volume of 20 ul in a 200 ul PCR tube. Reaction is carried out in a thermocycler at 50° C. for 1 hour. The reaction can then be stored at −20° C. For high concentration, 6 ul of the high concentration assembly master mix is used. DNA and water are added to a final volume of 20 ul in a 200 ul PCR tube. The reaction is carried out in a thermocycler at 50° C. for 1 hour. The reaction can then be stored at −20° C. Upon completion of the reaction, 10 ul is dialyzed against water for 30 min and electroporated into appropriate electro-competent cells (e.g., DH10B or Pir+ cells).

Cas9/Isothermal Assembly Reaction: For the Cas9 digest 2.5 ug of each DNA (e.g., BAC DNA), 4 ul of 10 uM guide/tracr RNAs each, and 5 ul of Cas9 protein (0.89 mg/ml) are digested for 2 hours at 37° C. The reaction is heat inactivated at 65° C. for 20 min, phenol chloroform extracted (e.g., to remove Cas9 protein), washed once with 70% ethanol, and DNA resuspended in 35 ul water. The Isothermal Assembly is performed with 5 ul of the DNA mixed together with 15 ul of the master mix (MM) as described elsewhere herein and incubated at 50° C. for 1 hour. The reaction is desalted for 30 min and 8 ul of the reaction can be electroporated into cells.

Example 7: Cas9/Isothermal Assembly to Insert Human Sequence into a BAC Vector In order to construct a humanized targeting vector, MAID 6236 was cleaved with a gRNA-Cas complex to generate a cleaved fragment with overlapping sequences. VI568 was also cleaved with a gRNA-Cas complex to generate sequences overlapping with the fragment of MAID6236. Cas9/Isothermal assembly was performed as described above resulting in insertion of the humanized locus into the vector (VI599). This process is outlined in FIG. 14.

Example 8: Cas9/Isothermal Assembly Using a gBlock without Selection

Cas9 digest and assembly can also be performed without selection, for example, by utilizing gBlock DNA fragments. In order to test the possibility of adding double stranded DNA into a locus without a selection cassette, gBlock DNA fragments were synthesized and inserted into the construct. As outlined in FIGS. 15 A and B, a Cas9/gRNA was designed to target two sites within the TCR beta locus to delete a 4.4 kb fragment. A gBlock was designed to introduce a meganuclease recognition site into the construct. The gBlock was able to insert into the construct without using a selection marker. FIG. 15 A shows the insertion of a PISceI gBlock and FIG. 15B demonstrates the insertion of a MauBI gBlock.

The final constructs were confirmed for successful insertion of each of the gBlocks by PCR junction screens using the primers indicated in Table 1. The protocol for the junction screens is as follows: The PCR reaction contained: 1 μL DNA, 0.5 μL Primer 1, 0.5 μL Primer 2, 1 μL DMSO, 4 μL dNTPs, 10× buffer, 0.5 μL Ex-Taq, and 15 μL Water. The Reaction was carried out in a thermocycler at 95° C. for 3 minutes, 95° C. for 30 sec, 55° C. for 30 sec for 25 cycles, followed by 72° C. for 30 sec, and 72° C. 5 min. The junction sequences were confirmed by sequencing.

TABLE 1

Primers for junction screening of MAID1715 with either PI-SceI gBlock or MauBI gBlock

| MAID1715 + PISceI Gblock | | |
|---|---|---|
| Primer name | Sequence | Junction size |
| (m380)5' 302p18 detect | GGAAAGCCACCCTGTATGCT (SEQ ID NO: 18) | 796 bp |
| 3'down detect 302p18(m41) | CTTGGCCAACAGTGGATGG (SEQ ID NO: 19) | |
| Cas9 Primer name | Sequence | DNA Target sequence |
| 1715 target-5' | CUAAAAUGAUUCUCAUCUGC GUUUUAGAGCUAUGCUGUUUUG (SEQ ID NO: 20) | CTAAAATGATTCTCATCTGC(AGG) (SEQ ID NO: 22) |
| 1715 target-3' | GCUCUCAACUUCACCCUUUC GUUUUAGAGCUAUGCUGUUUUG (SEQ ID NO: 21) | GCTCTCAACTTCACCCTTTC(TGG) (SEQ ID NO: 23) |
| MAID1715 + MauBI Gblock | | |
| Primer name | Sequence | Junction size |
| (m380)5' 302p18 detect | GGAAAGCCACCCTGTATGCT (SEQ ID NO: 18) | 759 bp |
| 3'down detect 302p18(m41) | CTTGGCCAACAGTGGATGG (SEQ ID NO: 19) | |
| Cas9 Primer name | Sequence | DNA Target sequence |
| 1715 target-5' | CUAAAAUGAUUCUCAUCUGC GUUUUAGAGCUAUGCUGUUUUG (SEQ ID NO: 20) | CTAAAATGATTCTCATCTGC(AGG) (SEQ ID NO: 22) |
| 1715 target-3' | GCUCUCAACUUCACCCUUUC GUUUUAGAGCUAUGCUGUUUUG (SEQ ID NO: 21) | GCTCTCAACTTCACCCTTTC(TGG) (SEQ ID NO: 23) |

Example 9: Cas9/Isothermal Assembly to Insert Human Sequence into a BAC Vector Using Joiner Oligos FIG. 16 provides an example of direct humanization using Cas9/isothermal assembly and joiner olios. The human fragment and the mouse deletion are dropped out by Cas9 (each BAC uses 2 crispr RNAs). The human fragment and mouse backbone are linked together in a Gibson Assembly reaction with 3 linkers (joiner oligos) and a selection cassette.

FIG. 17 provides an example of indirect humanization using Cas9/isothermal assembly and joiner oliogs for assembly into a large targeting vector (LTVEC). The human fragment on the hBAC is cleaved out by Cas9 using 2 crispr RNAs. The donor comprises up and down joiner oligos and a selection cassette. After hBAC cleavage by Cas9, the fragment is "captured" by Gisbon Assembly using a synthetic donor with incorporated complimentary overhangs. Targeting vector construction is completed by Gibson Assembly or BHR.

Example 10: Introducing a Point Mutation by Cas9/Isothermal Assembly

FIG. 18 provides an example of utilizing Cas9/Isothermal Assembly to introduce a point mutation. A donor is made by traditional cloning. A selection cassette is inserted into a synthetic DNA fragment that contains linker overlaps and the point mutation. The mBAC is cleaved with Cas9, the sequence is removed from the mBAC and the mBAC is Gibson Assembled to the donor resulting in a construct (LTVEC) comprising the point mutation and the selection cassette.

Example 11: BAC Trimming by Cas9/Isothermal Assembly

FIG. 19 provides an example of BAC trimming using the Cas9/isothermal assembly method. The area needed to be removed from the LTVEC is trimmed using Cas9. In this example, the BAC trimming removes the Ori sequence. The Ori is replaced in a Gibson Assembly reaction using 2 linkers (joiner oligos).

Example 12: Other Methods for BAC Digest with CAS9 Followed by Assembly

Other methods can be used in the methods provided herein including the following: Synthetic or in vitro-transcribed tracrRNA and crRNA were pre-annealed prior to the reaction by heating to 95° C. and slowly cooling down to room temperature. Native or linearized plasmid DNA (300 ng (about 8 nM)) was incubated for 60 min at 37° C. with a purified Cas9 protein (50-500 nM) and a tracrRNA:crRNA duplex (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions were stopped with 5×DNA loading buffer containing 250 mM EDTA, resolved by 0.8 or 1% agarose gel electrophoresis and visualized by ethidium bromide staining. For the Cas9 mutant cleavage assays, the reactions were stopped with 5×SDS loading buffer (30% glycerol, 1.2% SDS, 250 mM EDTA) prior to loading on the agarose gel.

An artificial crRNA and an artificial tracrRNA were designed to target specific sequences in the MAID 6177 (116 kb LTVEC) for assembly with a 3 kb PCR product (UB-HYG). The PCR product contained 50 bp overlaps with the vector. An isothermal one-step assembly was used based on the use of an isolated non-thermostable 5' to 3' exonuclease that lacks 3' exonuclease activity as follows. A reaction was set up containing the following: 100 fmol each dsDNA substrate, 16 µl 5×ISO buffer, 16 µl T5 exonuclease (0.2 U/µl, Epicentre), 8.0 µl Taq DNA ligase (40 U/µl, NEB), 1.0 µl Phusion™ DNA polymerase (2 U/µl, NEB), and water to 804 The 5×ISO (ISOthermal) buffer was 25% PEG-8000, 500 mM Tris-Cl, 50 mM MgCl2, 50 mM DTT, 5 mM NAD, and 1000 µM each dNTP (pH 7.5).

This gave a final concentration of 1.25 fmol/µl each dsDNA (or 45 fmol/µl each ssDNA) that was to be assembled, 5% PEG-8000, 100 mM Tris-Cl pH 7.5, 10 mM $MgCl_2$, 10 mM DTT, 200 MM each dNTP, 1 mM NAD, 0.02 U/µl T5 exonuclease, 4 U/µl Taq DNA ligase, and 0.03 U/µl PHUSION DNA polymerase.

Methods used 1.64 µl (0.2 U/µl) of T5 exonuclease for substrates that overlap by 20-80 bp, and for substrates that have larger overlaps (e.g., 200 bp), 1.6 µl (1 U/µl) of T5 exonuclease was used. T5 exonuclease was used as a 1:50 dilution (in T5 exonuclease storage buffer) from the 10 U/µl T5 exonuclease (Epicentre) concentrated enzyme stock. The reaction was then incubated at 50° C. for 15 minutes.

Example 13: Other Methods for Sewing Together Two Overlapping BACs

Other methods can be used in the methods provided herein including the following: Synthetic or in vitro-transcribed tracrRNA and crRNA were pre-annealed prior to the reaction by heating to 95° C. and slowly cooling down to room temperature. Native or linearized plasmid DNA (300 ng (about 8 nM)) was incubated for 60 min at 37° C. with a purified Cas9 protein (50-500 nM) and a tracrRNA:crRNA duplex (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions were stopped with 5×DNA loading buffer containing 250 mM EDTA, resolved by 0.8 or 1% agarose gel electrophoresis and visualized by ethidium bromide staining. For the Cas9 mutant cleavage assays, the reactions were stopped with 5×SDS loading buffer (30% glycerol, 1.2% SDS, 250 mM EDTA) prior to loading on the agarose gel.

An artificial crRNA and an artificial tracrRNA were designed to target specific sequences in the humanized HLA-DQ BAC for assembly with a humanized HLA-DR BAC. The vectors contained ~70 bp overlaps with each other created by Cas9 cleavage at two sites on each vector (See, FIG. 2). An isothermal one-step assembly was used based on the use of an isolated non-thermostable 5' to 3' exonuclease that lacks 3' exonuclease activity as follows. A reaction was set up containing approximately the following: 100 fmol each dsDNA substrate, 16 µl 5× ISO buffer, 16 µt T5 exonuclease (0.2 U/µl, Epicentre), 8.0 µl Taq DNA ligase (40 U/µl, NEB), 1.0 µl Phusion™ DNA polymerase (2 U/µl, NEB), and water to 80 µl. The 5×ISO (ISOthermal) buffer was 25% PEG-8000, 500 mM Tris-Cl, 50 mM MgCl2, 50 mM DTT, 5 mM NAD, and 1000 µM each dNTP (pH 7.5).

This gave a final concentration of about 1.25 fmol/µl each dsDNA (or 45 fmol/µl each ssDNA) that was to be assembled, 5% PEG-8000, 100 mM Tris-Cl pH 7.5, 10 mM $MgCl_2$, 10 mM DTT, 200 MM each dNTP, 1 mM NAD, 0.02 U/µl T5 exonuclease, 4 U/µl Taq DNA ligase, and 0.03 U/µl PHUSION DNA polymerase.

Methods used 1.64 µl 0.2 U/µl T5 exonuclease for substrates that overlap by 20-80 bp, and for substrates that have larger overlaps (e.g., 200 bp), 1.6 μl 1 U/μl T5 exonuclease was used. T5 exonuclease was used as a 1:50 dilution (in T5 exonuclease storage buffer) from the 10 U/μl T5 exonuclease (Epicentre) concentrated enzyme stock. The reaction was then incubated at 50° C. for 15 minutes.

Example 14: Other Methods for Assembling an Insert with a BAC Vector

Other methods can be used in the methods provided herein including the following: Dissolve crRNAs and tracrRNA to 100 uM in Hybe Buffer (10× buffer: 20 mM Tris 7.5, 100-150 mM NaCl, 10 mM $MgCl_2$, 1 mM DTT, 0.1 mM EDTA, 100 ug/ml BSA). In order to anneal the RNAs, add 10 ul of 100 uM crRNA and 10 ul of 100 uM tracrRNA to 80 ul of annealing buffer. Heat RNAs in a 90° C. temp block then remove block from heater and cool on bench. Final concentration of RNA is about 10 uM.

In order to digest the BAC, clean maxiprep BAC DNA is used and the BAC digested according to the following mixture.

|  | 1X |
| --- | --- |
| BAC DNA 500 ng | X ul |
| BSA | 0.5 ul |
| RNA | 2 ul (1 ul of each tracr:crRNA hybrid) |
| Cas9 (4.5 mg/ml) | 1 ul |
| 10x Buffer | 1.5 ul |
| $H_2O$ | to 15 ul |

Digest for 1 hour at 37° then de-salt for 30 min.

In order to assemble the BAC and insert, digest a plasmid or perform PCR to create an insert. For PCR reactions, run a small aliquot on a gel and look for a clean product, if the product is not clean then do PCR cleanup instead of gel extraction. A 1:1-1:6 molar ratio for the BAC:Insert is desired. Usually, 50 ng of the purified insert will work. The following reaction mix can be used:

| BAC Digest | 4 ul |
| --- | --- |
| Insert | 1 ul |
| Assembly Mix | 15 ul |

Add the DNA and Mix on ice or directly in a PCR machine at 50° C. Incubate at 50° C. for 1 hour. Add 0.5 uL of Proteinase K (20 mg/ml) and incubate at 50° C. for 1 hour. Desalt for 30 min and electroporate 8 ul of the reaction into DH10B cells. 10 ul of the BAC Digest can be run on a pulse-field gel to check digestion efficiency. Use RNase-free water and buffers. The final reaction buffer contains: 20 mM Tris 7.5; 100-150 mM NaCl; 10 mM MgCl2; 1 mM DTT; 0.1 mM EDTA; 100 ug/ml BSA; for a final volume of 15 ul.

The tracr RNA sequence used in the example is: CAAAACAGCAUAGCAAGUUAAAAUAAGGCUAGUCCGUUAUC (SEQ ID NO: 9). This CRISPR RNA (crRNA) contains: (1) about 20 nucleotides of RNA complementary to a target sequence and (2) a tail sequence (GUUUUAGAGCUAUGCUGUUUUG (SEQ ID NO: 10)) that will anneal to the tracrRNA.

---

We claim:

1. An in vitro method for assembling at least two nucleic acids, comprising:
   (a) contacting a first nucleic acid with a first nuclease agent, wherein the first nuclease agent comprises a Cas9 protein and a guide RNA (gRNA) (gRNA-Cas9 complex), a zinc finger nuclease, or a Transcription Activator-Like Effector Nuclease (TALEN), wherein the first nuclease agent cleaves the first nucleic acid at a first target site to produce a first digested nucleic acid with an overlapping end sequence shared by a second nucleic acid;
   (b) contacting the first digested nucleic acid and the second nucleic acid with an exonuclease to expose complementary sequences between the first digested nucleic acid and the second nucleic acid; and
   (c) assembling the two nucleic acid fragments generated from step (b).

2. The method of claim 1, wherein step (c) comprises:
   (i) annealing the exposed complementary sequences;
   (ii) extending the 3' ends of the annealed complementary sequences; and
   (iii) ligating the first and the second nucleic acids.

3. The method of claim 1, wherein the at least two nucleic acids are double stranded.

4. The method of claim 1, wherein the overlapping end sequence ranges from 20 bp to 200 bp long.

5. The method of claim 1, wherein step (a) further comprises contacting the second nucleic acid with a second nuclease agent, wherein the second nuclease agent cleaves the second nucleic acid at a second target site to produce a second digested nucleic acid with the overlapping end sequence, and
   wherein the second nucleic acid of step (b) is the second digested nucleic acid.

6. The method of claim 1, wherein the first nuclease agent comprises the Cas9 protein and the gRNA, wherein the gRNA comprises a nucleic acid sequence encoding a Clustered Regularly Interspaced Short Palindromic Repeats (CRISPR) RNA (crRNA) and a trans-activating CRISPR RNA (tracrRNA), and the first target site is immediately flanked by a Protospacer Adjacent Motif (PAM) sequence.

7. The method of claim 6, wherein the Cas9 protein comprises a RuvC domain and an HNH domain, at least one of which lacks endonuclease activity.

8. The method of claim 1, wherein the first nucleic acid, the second nucleic acid, or both nucleic acids comprise a bacterial artificial chromosome.

9. The method of claim 1, wherein the first nucleic acid, the second nucleic acid, or both nucleic acids comprise a human DNA, a rodent DNA, a synthetic DNA, or a combination thereof.

10. The method of claim 1, wherein the first nucleic acid, the second nucleic acid, or both nucleic acids are vectors from about 20 kb to about 400 kb in length.

11. The method of claim 1, wherein the assembled nucleic acid is from 30 kb to 1 Mb in length.

12. The method of claim 1, wherein the first nucleic acid comprises a first bacterial artificial chromosome, the second nucleic acid comprises a second bacterial artificial chromosome, a gene of interest spans the first and second bacterial artificial chromosomes, and the assembly forms the sequence of the gene of interest.

13. The method of claim 1, wherein the first nucleic acid is a circular nucleic acid.

14. The method of claim 1, wherein the first nucleic acid is a linear nucleic acid.

15. The method of claim 1, wherein the assembled nucleic acid is a circular nucleic acid.

16. The method of claim 1, wherein the assembled nucleic acid is a linear nucleic acid.

17. The method of claim 1, wherein at least three nucleic acids are assembled.

18. An in vitro method for assembling two or more nucleic acids, comprising:
   (a) contacting a first nucleic acid with at least one nuclease agent, wherein the at least one nuclease agent comprises a Cas9 protein and a guide RNA (gRNA) (gRNA-Cas9 complex), a zinc finger nuclease, or a Transcription Activator-Like Effector Nuclease (TALEN), wherein the at least one nuclease agent cleaves the first nucleic acid at a first target site to generate a first digested nucleic acid;
   (b) contacting the first digested nucleic acid with a second nucleic acid, a joiner oligo, and an exonuclease, wherein the joiner oligo comprises:
      (i) a first complementary sequence that is complementary to the first digested nucleic acid;

(ii) a spacer; and
(iii) a second complementary sequence that is complementary to the second nucleic acid;
wherein the exonuclease exposes the first and second complementary sequences; and
(c) assembling the joiner oligo with the first digested nucleic acid and the second nucleic acid.

19. The method of claim 18, wherein assembling in step (c) comprises:
(i) annealing the first complementary sequence of the joiner oligo to the first digested nucleic acid and the second complementary sequence of the joiner oligo to the second nucleic acid; and
(ii) ligating the joiner oligo to the first digested nucleic acid and the second nucleic acid.

20. The method of claim 19, wherein step (i) further comprises extending the 3' end of the first digested nucleic acid and/or the second nucleic acid.

21. The method of claim 18, wherein the first complementary sequence of the joiner oligo is between 15 and 120 complementary bases, and the second complementary sequence of the joiner oligo is between 15 and 120 complementary bases.

22. The method of claim 18, wherein the spacer of the joiner oligo comprises non-complementary nucleic acids.

23. The method of claim 22, wherein the spacer of the joiner oligo comprises a drug resistance gene, a reporter gene, sequences for detection, or one or more restriction enzyme sites to confirm successful assembly.

24. The method of claim 18, wherein the two or more nucleic acids are double-stranded.

25. The method of claim 18, wherein the joiner oligo comprises a linear double-stranded DNA fragment.

26. The method of claim 25, wherein the linear double-stranded DNA fragment does not comprise a selection cassette.

27. The method of claim 25, wherein the joiner oligo is from about 50 bp to about 400 bp.

28. The method of claim 27, wherein the joiner oligo is from about 100 bp to about 300 bp.

29. The method of claim 18, wherein the joiner oligo is a single-stranded DNA.

30. The method of claim 18, wherein the first digested nucleic acid is seamlessly assembled to the second nucleic acid.

31. The method of claim 30, wherein the at least one nuclease agent is designed to cleave an at least 20 bp fragment from the end of the first nucleic acid at which the seamless assembly will occur,
wherein the spacer of the joiner oligo comprises a sequence identical to the at least 20 bp fragment, wherein no nucleic acid bases are present between the first complementary sequence and the at least 20 bp fragment, and no nucleic acid bases are present between the second complementary sequence and the at least 20 bp fragment,
such that assembly of the first digested nucleic acid with the joiner oligo and the second nucleic acid reconstitutes the at least 20 bp fragment and seamlessly assembles the first nucleic acid and the second nucleic acid.

32. The method of claim 31, wherein the at least 20 bp fragment is double-stranded.

33. The method of claim 30, wherein the joiner oligo comprises a linear double stranded DNA fragment.

34. The method of claim 33, wherein the linear double stranded DNA fragment does not comprise a selection cassette.

35. The method of claim 30, wherein the joiner oligo is from about 50 bp to about 400 bp.

36. The method of claim 35, wherein the joiner oligo is from about 100 bp to about 300 bp.

37. The method of claim 18, wherein the spacer is between about 20 bp to about 120 bp.

38. The method of claim 18, wherein the joiner oligo is assembled to the first nucleic acid and the second nucleic acid in the same reaction.

39. The method of claim 18, wherein the joiner oligo is assembled to the first nucleic acid and the second nucleic acid sequentially.

40. The method of claim 18, wherein step (a) further comprises:
(i) contacting the second nucleic acid with a second nuclease agent, wherein the second nuclease agent cleaves the second nucleic acid at a second target site to produce a second digested nucleic acid comprising a nucleotide sequence that is complementary to the second complementary sequence of the joiner oligo, wherein the first digested nucleic acid is assembled to the second digested nucleic acid; or
(ii) contacting the second nucleic acid with a restriction enzyme or meganuclease, wherein the restriction enzyme or meganuclease cleaves the second nucleic acid to produce a second digested nucleic acid comprising a nucleotide sequence that is complementary to the second complementary sequence in the joiner oligo, wherein the first digested nucleic acid is assembled to the second digested nucleic acid.

41. The method of claim 18, wherein the at least one nuclease agent comprises the Cas9 protein and the gRNA, wherein the gRNA comprises a nucleic acid sequence encoding a Clustered Regularly Interspaced Short Palindromic Repeats (CRISPR) RNA (crRNA) and a trans-activating CRISPR RNA (tracrRNA), and wherein the first target site is immediately flanked by a Protospacer Adjacent Motif (PAM) sequence.

42. The method of claim 41, wherein the Cas9 protein comprises a RuvC domain and an HNH domain, at least one of which lacks endonuclease activity.

43. The method of claim 18, wherein the first nucleic acid, the second nucleic acid, or both nucleic acids comprise a bacterial artificial chromosome.

44. The method of claim 18, wherein the first nucleic acid, the second nucleic acid, or both nucleic acids comprise a human DNA, a rodent DNA, a synthetic DNA, or a combination thereof.

45. The method of claim 18, wherein the first nucleic acid, the second nucleic acid, or both nucleic acids are vectors from about 20 kb to about 400 kb in length.

46. The method of claim 18, wherein the assembled nucleic acid is from 30 kb to 1 Mb in length.

47. The method of claim 18, wherein the first nucleic acid comprises a first bacterial artificial chromosome, the second nucleic acid comprises a second bacterial artificial chromosome, a gene of interest spans the first and second bacterial artificial chromosomes, and the assembly forms the sequence of the gene of interest.

48. The method of claim 18, wherein the first nucleic acid is a circular nucleic acid.

49. The method of claim 18, wherein the first nucleic acid is a linear nucleic acid.

50. The method of claim 18, wherein the assembled nucleic acid is a circular nucleic acid.

51. The method of claim 18, wherein the assembled nucleic acid is a linear nucleic acid.

52. The method of claim 18, wherein at least three nucleic acids are assembled.

* * * * *